(12) United States Patent
Winter et al.

(10) Patent No.: US 6,696,245 B2
(45) Date of Patent: Feb. 24, 2004

(54) METHODS FOR SELECTING FUNCTIONAL POLYPEPTIDES

(75) Inventors: Greg Winter, Cambridge (GB); Ian Tomlinson, Cambridge (GB)

(73) Assignee: Domantis Limited (GB)

( * ) Notice: Subject to any disclaimer, the term of this patent is extended or adjusted under 35 U.S.C. 154(b) by 0 days.

(21) Appl. No.: 09/192,854

(22) Filed: Nov. 17, 1998

(65) Prior Publication Data

US 2002/0068276 A1 Jun. 6, 2002

Related U.S. Application Data

(60) Provisional application No. 60/065,428, filed on Nov. 13, 1997, and provisional application No. 60/066,729, filed on Nov. 21, 1997.

(30) Foreign Application Priority Data

Oct. 20, 1997 (GB) .............................................. 9722131

(51) Int. Cl.$^7$ ............................. C12Q 1/70; C12Q 1/68; C12N 15/00; C12P 21/08

(52) U.S. Cl. ................................ 435/6; 435/5; 435/7.1; 435/69.1; 435/320.1; 435/DIG. 3; 435/DIG. 4; 435/DIG. 23; 435/DIG. 24; 530/388.1; 536/25.3

(58) Field of Search ............................. 435/71.5, 320.1, 435/6, 69.1, DIG. 3, DIG. 4, DIG. 23, DIG. 24; 530/300, 350, 388.1; 436/518, 501; 536/18.5, 25.3

(56) References Cited

U.S. PATENT DOCUMENTS

| | | | |
|---|---|---|---|
| 31,006 A | 1/1861 | Briggs | |
| 2,019,408 A | 10/1935 | Grill | |
| 4,631,211 A | 12/1986 | Houghten | ..................... 428/35 |
| 5,143,854 A | 9/1992 | Pirrung et al. | ............... 436/518 |
| 5,169,936 A | 12/1992 | Staples et al. | ............... 530/350 |
| 6,057,098 A | * 5/2000 | Buechler et al. | ................ 435/6 |

FOREIGN PATENT DOCUMENTS

| | | | |
|---|---|---|---|
| WO | 84/03564 | 9/1984 | .......... G01N/33/54 |
| WO | 88/08453 | 11/1988 | ............ C12P/21/00 |
| WO | 90/05785 | 5/1990 | ............ C12P/19/34 |
| WO | 90/07003 | 6/1990 | ............ C12P/21/00 |
| WO | 90/15070 | 12/1990 | ............. C07K/1/04 |
| WO | 91/02076 | 2/1991 | ............ C12P/21/00 |
| WO | 91/05058 | 4/1991 | ............ C12P/21/00 |
| WO | 92/00091 | 1/1992 | ............ A61K/37/02 |
| WO | 92/02536 | 2/1992 | ............. C07K/3/00 |
| WO | 92/05258 | 4/1992 | ............ C12N/15/56 |
| WO | 92/10092 | 6/1992 | ............. A01N/1/02 |
| WO | 92/14843 | 9/1992 | ............. C12Q/1/68 |
| WO | 93/06121 | 4/1993 | ............ C07H/21/00 |
| WO | 95/11922 | 5/1995 | ............ C07K/16/00 |
| WO | 95/22625 | 8/1995 | ............. C12Q/1/68 |
| WO | 96/06213 A1 | 2/1996 | .......... D03D/41/00 |
| WO | 9708320 | 3/1997 | ............ C12N/15/13 |

OTHER PUBLICATIONS

Kang, et al., "Linkage of recognition and replication functions by assembling combinatorial antibody Fab libraries along phage surfaces", *Proc. Natl. Acad. Sci. USA*, 1991, 88:4363.

Kawasaki, et al., "One–Megabase Sequence Analysis of the Human Immunoglobulin λ Gene Locus", *Genome Res.*, 1997, 7:250–261.

Knight, et al., "Three Genes For Lupus Nephritis In NZB +NZW Mice", *J. Exp. Med.*, 1978, 147:1653–1660.

Lefkovits and Pernis, *Immunological Methods*, vol. I and II, Academic Press, NY, 1979 and 1981.

Lerner, et al., "Antibodies Without Immunization", *Science*, 1992, 258:1313–1314.

Li, et al., "Design, synthesis, and application of a Protein A mimetic", *Nature Biotechnology*, 1998, 16:190–195.

Lindstrom, et al., "Myasthenia Gravis", *Adv. Immunol.*, 1988, 42:233–284.

Low, et al., "Mimicking Somatic Hypermutation: Affinity Maturation of Antibodies Displayed on Bacteriophage Using a Bacterial Mutator Strain", *J. Mol. Biol.*, 1996, 260:359–368.

Lowman, et al., "Selecting High–Affinity Binding Proteins by Monovalent Phage Display", *Biochemistry*, 1991, 30:10832–10838.

Marks, et al., "By–passing Immunization Human Antibodies from V–gene Libraries Displayed on Phage", *J. Mol. Biol.*, 1991, 222:581–597.

Marks, et al., "Molecular Evolution of Proteins of Filamentous Phage", *J. Biol. Chem.*, 1992, 267:16007–16010.

Maron, et al., "H–2K Mutation Controls Immune Response Phenotype of Autoimmune Thyroiditis", *J. Exp. Med.*, 1980, 152:1115–1120.

(List continued on next page.)

*Primary Examiner*—Padmashri Ponnaluri
(74) *Attorney, Agent, or Firm*—Kathleen M. Williams; Mark J. FitzGerald; Palmer & Dodge, LLP

(57) ABSTRACT

The invention provides a method for selecting, from a repertoire of polypeptides, a population of functional polypeptides which bind a target ligand in a first binding site and a generic ligand in a second binding site, which generic ligand is capable of binding functional members of the repertoire regardless of target ligand specificity, comprising the steps of: a) contacting the repertoire with the generic ligand and selecting functional polypeptides bound thereto; and b) contacting the selected functional polypeptides with the target ligand and selecting a population of polypeptides which bind to the target ligand. The invention accordingly provides a method by which a polypeptide repertoire is preselected, according to functionality as determined by the ability to bind the generic ligand, and the subset of polypeptides obtained as a result of such preselection is then employed for further selection according to the ability to bind the target ligand.

21 Claims, 9 Drawing Sheets

OTHER PUBLICATIONS

Martin, et al., "Structural Families in Loops of Homologous Proteins: Automatic Classification, Modelling and Application to Antibodies", *J. Mol. Biol.*, 1996, 263:800–815.

Matteucci and Caruthers, "Synthesis of Deoxyoligonucleotides on a Polymer Support", *J. Am. Chem., Soc.*, 1981, 103:3185–3191.

McFarlin, et al., "Experimental Allergic Encephalomyelitis in the Rat: Response to Encephalitogenic Proteins and Peptides", *Science*, 1973, 179:478–480.

Mullinax, et al., "Identification of human antibody fragment clones specific for tetanus toxoid in a bacteriophage λ immunoexpression library", *Proc. Natl. Acad. Sci. USA*, 1990, 87:8095–8099.

Mullis and Faloona, "Specific Synthesis of DNA in Vitro via a Polymerase–Catalyzed Chain Reaction", *Methods Enzymol*, 1987, 155:335–350.

Nissim, et al., "Antibody fragments from a 'single pot'phage display library as immunochemical reagents", *EMBO J.* 1994, 13:692–698.

Paterson, *Textbook of Immunopathology*, Mischer, et al., eds., Grune and Stratton, NY, 1987, pp. 179–213 Experimental Autoimmune (Allergic) Encephalomyelitis induction, Pathogenesis.

Persson, et al., "Generation of diverse high–affinity human monoclonal antibodies by repertoire cloning", *Proc. Natl. Acad. Sci, USA*, 1991, 88:2432–2436.

Ravetch, et al., "Structure of the Human Immunoglobulin μLocus: Characterization of Embryonic and Rearranged J and D Genes", *Cell*, 1981, 27:583–591.

Reinersten, et al., "B–Lymphocyte Alloantigens Associated with Systemic Lupus Erythematosus", *New Eng. J. Med.*, 1978, 299:515–518.

Reis, et al., "Streptococcal Fc Receptors", *J. Immunol.*, 1984, 132:3091–3097.

Sambrook, et al., *Molecular Cloning: A Laboratory Manual*, Cold Spring Harbor, USA, 1989, (cover pages only).

Satoh, et al., "Experimental Allergic Encephalomyelitis Mediated by Murine Encephalitogenic T Cell Lines Specific for Myelin Proteolipid Apoprotein", *J. Immunol.*, 1987, 138:179–184.

Schäble and Zachau, "The Variable Genes of the Human Immunoglobulin +Locus", *Biol. Chem. Hoppe–Seyler*, 1993, 374:1001–1022.

Scott and Smith, "Searching for Peptide Ligands with an Epitope Library", *Science*, 1990, 239:386–390.

Shirai, et al., "Structural classification of CDR–H3 in antibodies", *FEBS Letters*, 1996, 399:1–8.

Smith, "Filamentous Fusion Phage: Novel Expression Vectors That Display Cloned Antigens on the Virion Surface", *Science*, 1985, 228:1315–1317.

Thiesen and Bach, "Target Detection Assay (TDA): a versatile procedure to determine DNA binding sites as demonstrated on SP1 protein", *Nucleic Acids Res.*, 1990, 18:3203–3209.

Tomlinson, et al., "The Imprint of Somatic Hypermutation on the Repertoire of Human Germline V Genes", *J. Mol. Biol.*, 1996, 256:813–817.

Tomlinson, et al., "The structural repertoire of the human $V_x$ domain", *EMBO J.*, 1995, 14:4628–4638.

Tuerk and Gold, "Systemic Evolution of Ligands by Exponential Enrichment: RNA ligands to Bacteriophage T4 DNA Polymerase", *Science*, 1990, 249;505–510.

van Eden, et al., "Cloning of the mycobacterial epitope recognized by T lymphocytes in adjuvant arthritis", *Nature*, 1988, 331:171–173.

Vasicek and Leder, "Structure and Expression of the Human Immunoglobulin μGenes", *J. Exp. Med.*, 1990, 172:609–620.

Vaughan, et al., "Human Antibodies with Sub–nanomolar Affinities Isolated from a Large Non–immunized Phage Display Library", *Nature Biotech*, 1996, 14:309–314.

Voller, et al., "Enzyme immunoassays with special reference to ELISA techniques", *J. Clin. Pathol.*, 1978, 31:507–520.

Williams, et al., "Sequence and Evolution of the Human Germline Vμ Repertoire", *J. Mol. Biol.*, 1996, 264:220–232.

Arnheiter, et al., "Physicochemical and antigenic properties of synthetic fragments of human leukocyte interferon", *Nature*, 1981, 294:278–280.

Barbas, et al., "Semisynthetic combinatorial antibody libraries: A chemical solution to the diversity problem", *Proc. Natl. Acad. Sci. USA*, 1992, 89:4457–4461.

Beaucage and Carruthers, "Deoxynucleoside Phosphoramidites—A new class of Key Intermediates for Deoxypolynucleotide Synthesis", *Tetrahedron Lett.*, 1981, 22:1859–1862.

Beaudry and Joyce, "Directed Evolution of an RNA Enzyme", *Science*, 1992 257:635–641.

Reinherz, et al., *Leukocyte Typing*, Springer Verlag, NY (1984).

Björck and Kronvall, "Purification and some Properties of Streptococcal Protein G, A Novel IgG–Binding Reagent", *J. Immunol.*, 1984, 133:969–974.

Fishwild, *J. Immunol.*, "Activation of HLA–Restricted EBV–Specific Cytotoxic T Cells Does Not Require CD4+ (HELPER) T Cells or Exogenous Cytokines", 1988, 140:1994–1998.

Boersma and Van Leeuwen, "Technical aspects of opioid receptor localization: detection of opioid receptor proteins by immunocytochemistry or with a biotinylated dynorphin analog", *J. Neurosci. Methods*, 1994, 51:217–227.

Breitling, et al., "A surface expression vector for antibody screening", *Gene*, 1991, 104:147–153.

Burton, et al., "A large array of human monoclonal antibodies to type 1 human immunodeficiency virus from combinatorial libraries of asymptomatic seropositive individuals", *Proc. Natl. Acad. Sci. USA*, 1991, 88:10134–10137.

Butler, "The Amplified ELISA: Principles of and Applications for the Comparative quantitation of Class and Subclass Antibodies and the Distribution of Antibodies and Antigens in Biochemical Separates", *Methods Enzymol.*, 1981, 73:482–523.

Caton and Koprowski, "Influenza virus hemagglutinin–specific antibodies isolated from a combinatorial expression library are closely related to the immune response of the donor", *Proc. Natl. Acad. Sci, USA*, 1990, 87; 6450–6454.

Chang, et al., "Expression of Antibody Fab Domains on Bacteriophage Surfaces Potential Use for Antibody Selection", *J. Immunol*, 1991, 147:3610–3614.

Chaudhary, et al., "A rapid method of cloning functional variable–region antibody genes in *Escherichia coli* as single–chain immunotoxins", *Proc. Natl. Acad. Sci. USA*, 1990, 87:1066–1070.

Chiswell and McCafferty, "Phage antibodies: will new 'coliclonal' antibodies replace monoclonal antibodies?", *Trends Biotech*, 1992, 10:80–84.

Chothia, et al., "Structural Repertoire of the Human $V_H$ Segments", *J. Mol. Biol.*, 1992, 227:799–817.

Chothia, et al., "Conformations of immunoglobulin hypervariable regions", *Nature*, 1989, 342:877–883.

Chothia and Lesk, "Canonical Structures for the Hypervariable Regions of Immunoglobulins" *J. Mol. Biol.*, 1987, 196:901–917.

Clarkson, et al., "Making antibody fragments using phage display libraries", *Nature*, 1991, 352:624–628.

Cook and Tomlinson, "The human immunoglobulin $V_H$ repertoire", *Immunol. Today*, 1995, 16:237–242.

Cox, et al., "A directory of human germ–line $V_x$ segments reveals a strong bias in their usage", *Eur. J. Immunol.*, 1994, 24:827–836.

Crameri, et al., "Construction and evolution of antibody–phage libraries by DNA shuffling", *Nature Med., 1996, 2:100*–102.

de Kruif, et al., "Selection and Application of Human Single Chain Fv Antibody Fragments from a Semi–synthetic Phage Antibody Display Library with Designed CDR3 Regions", *J. Mol. Biol.*, 1995, 248:97–105.

Deng, et al., "Selection of Antibody Single–chain Variable Fragments with Improved Carbohydrate Binding by Phage Display", *J. Biol. Chem.*, 1994, 269:9533–9538.

Dower and Fodor, "The Search for Molecular Diversity: Recombinant and Synthetic Randomized Peptide Libraries", *Ann. Rep. Med. Chem.*, 1991, 26:271–280.

Dymecki, et al., "Structure and Developmental Regulation of the B–lymphoid Tyrosine Kinase Gene blk", *J. Biol. Chem*, 1992, 267:4815–4823.

Ellington and Szostak, "In vitro selection of RNA molecules that bind specific ligands", *Nature*, 1990, 346:818–822.

Fodor, et al., "Light–Directed, Spatially Addressable Parallel Chemical Synthesis", *Science*, 1991, 251:767–777.

Norman, et al., "Preparation and Evaluation of Antigens for use in the Serologic Diagnosis of Human Hydatid Disease", *J. Immunol.*, 1966, 97:822–828.

Green, et al., "Immunogenic Structure of the Influenza Virus Hemagglutinin", *Cell*, 1982, 28:477–487.

Griffiths, et al., "Isolation of high affinity human antibodies directly form large synthetic repertoires", *EMBO J.*, 1994, 13:3245–3260.

Hawkins, et al., "Selection of Phage Antibodies by Binding Affinity Mimicking Affinity Maturation", *J. Mol. Biol.*, 1992, 226:889–896.

Hieter, et al., "Evolution of Human Immunoglobulin k J Region Genes", *J. Biol. Chem.*, 1982, 257:1516–1522.

Hoogenbloom and Winter, "By–passing Immunisation, Human Antibodies from Synthetic Repertoires of Germline $V_H$ Gene Segments Rearranged in Vitro", *J. Mol. Biol.*, 1992, 227:381–388.

Hoggenbloom, et al., "Multi–subunit proteins on the surface of filamentous phage: methodologies for displaying antibody (Fab) heavy and light chains", *Nucleic Acids Res.*, 1991, 19–4133–4137.

Hubert and Porath, "Metal Chelate Affinity Chromatography", *J. Chromatography*, 1980, 98:247–255.

Huse, et al., "Generation of a Large Cominatorial Library of the Immunoglobulin Repertoire in Phage Lambda", *Science*, 1989, 246:1275–1281.

Huston, et al., "Protein engineering of antibody binding sites: Recovery of specific activity in an anti–digoxin single–chain Fv analogue produced in *Escherichia coli*", *Proc. Natl. Acad. Sci. USA*, 1988, 85:5879–5883.

Kanazawa, et al., "Non–obese–diabetic mice: immune mechanisms of pancreatic β–cell destruction", *Diabetologia*, 1984, 27:113–115.

Kanehisa, "Use of statistical criteria for screening potential homologies in nucleic acid sequences", *Nucleic Acids Res.*, 1984, 12:203–213.

* cited by examiner

FIG. 2

| FIG. 2A |
|---------|
| FIG. 2B |

FIG. 2A

```
H1                                                      H10                                                      H20                                                     H30
E   V   Q   L   L   E   S   G   G   G   L   V   Q   P   G   G   S   L   R   L   S   C   A   A   S   G   F   T   F   S
GAG GTG CAG CTG TTG GAG TCT GGG GGA GGC TTG GTA CAG CCT GGG GGG TCC CTG AGA CTC TCC TGT GCA GCC TCT GGA TTC ACC TTT AGC

H40                                         H50   H52 a
S   Y   A   M   S   W   V   R   Q   A   P   G   K   G   L   E   W   V   S   A   I   S   G   S   G   G   S   T   Y   Y
AGC TAT GCC ATG AGC TGG GTC CGC CAG GCT CCA GGG AAG GGG CTG GAG TGG GTC TCA GCT ATT AGT GGT AGT GGT AGT ACA TAC TAC
        HCDR1                                                                   HCDR2

H60                                         H70                                                     H80    H82 a   b   c
A   D   S   V   K   G   R   F   T   I   S   R   D   N   S   K   N   T   L   Y   L   Q   M   N   S   L   R   A   E   D
GCA GAC TCC GTG AAG GGC CGG TTC ACC ATC TCC AGA GAC AAT TCC AAG AAC ACG CTG TAT CTG CAA ATG AAC AGC CTG AGA GCC GAG GAC

H90                                 H98 H100                                                                H110         H113
T   A   V   Y   Y   C   A   K   S   Y   G   A   F   D   Y   W   G   Q   G   T   L   V   T   V   S   S   G   G   G   G
ACG GCC GTA TAT TAC TGT GCG AAA AGT TAT GGT GCT TTT GAC TAC TGG GGC CAG GGA ACC CTG GTC ACC GTC TCG AGC GGT GGA GGC GGT
                                            HCDR3                                                                                    XhoI
```

```
                                                                                                      L10
 S   G   G   G   G   S   G   G   G   G   S   T   D   I   Q   M   T   Q   S   P   S   S   L   S   A   S   V   G   D   R
TCA GGC GGA GGT GGC AGC GGC GGT GGC TCG ACG GAC ATC CAG ATG ACC CAG TCT CCA TCC TCC CTG TCT GCA TCT GTA GGA GAC AGA
                                         Sal I
         L20                                     L30                                             L40
 V   T   I   T   C   R   A   S   Q   S   I   S   S   Y   L   N   W   Y   Q   Q   K   P   G   K   A   P   K   L   L   I
GTC ACC ATC ACT TGC CGG GCA AGT CAG AGC ATT AGC AGC TAT TTA AAT TGG TAT CAG CAG AAA CCA GGG AAA GCC CCT AAG CTC CTG ATC
                                        LCDR1
         L50                                     L60                                             L70
 Y   A   A   S   S   L   Q   S   G   V   P   S   R   F   S   G   S   G   S   G   T   D   F   T   L   T   I   S   S   L
TAT GCT GCA TCC AGT TTG CAA AGT GGG GTC CCA TCA AGG TTC AGT GGC AGT GGA TCT GGG ACA GAT TTC ACT CTC ACC ATC AGC AGT CTG
         LCDR2
         L80                                     L90                                             L100                    L107
 Q   P   E   D   F   A   T   Y   Y   C   Q   Q   S   Y   S   T   P   N   T   F   G   Q   G   T   K   V   E   I   K   R
CAA CCT GAA GAT TTT GCA ACT TAC TAC TGT CAA CAG AGT TAC AGT ACC CCT AAT ACG TTC GGC CAA GGG ACC AAG GTG GAA ATC AAA CGG
                                                LCDR3
```

☐ Diversified in "Primary" library only

☐ Diversified in "Somatic" library only

☐ Diversified in "Primary" and "Somatic" libraries

FIG. 2B

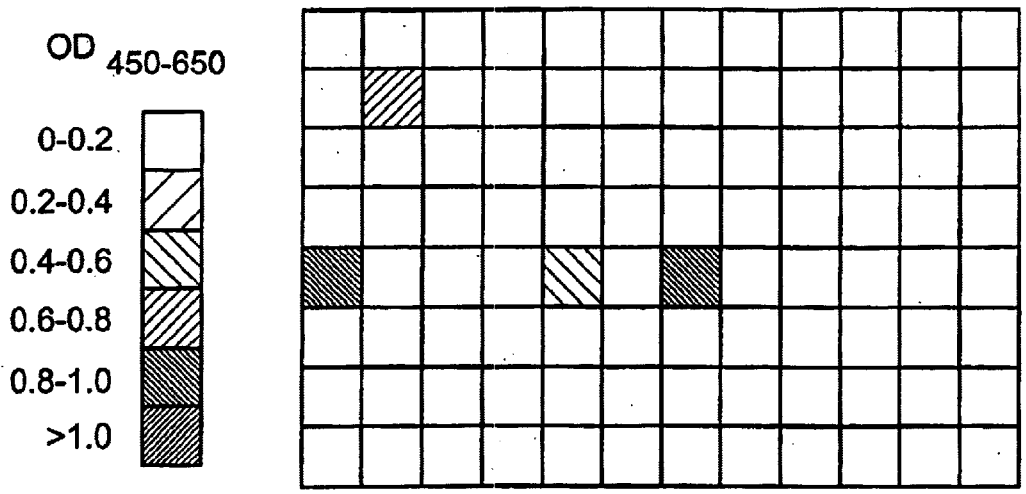
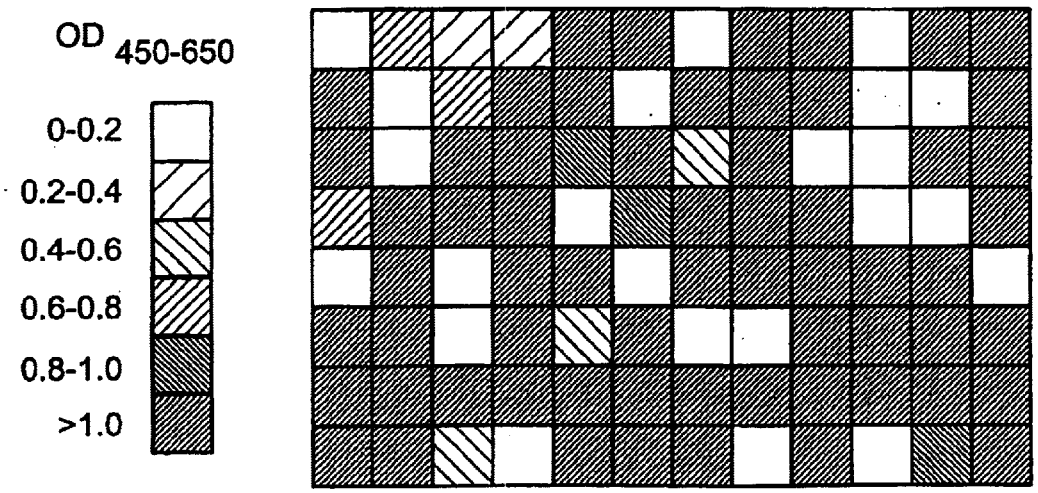
FIG. 3
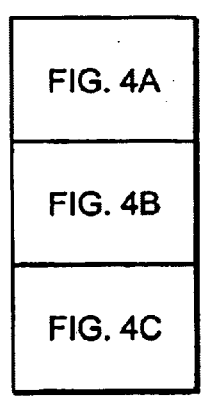
FIG. 4

| Clones | Antigen | Library | Heavy chain (framework DP-47) | | | Light chain (framework DPK9) | | | No* |
|---|---|---|---|---|---|---|---|---|---|
| | | | CDR1 | CDR2 | CDR3 | CDR1 | CDR2 | CDR3 | |
| UBIA 1-9 | Bovine ubiquitin | Primary NNK | SYAMS | IIGSEGWPTIYADSVKG | GGSMFDY | RASQSISSYLN | RASSLQS | QQSSNTPYT | 9 |
| UBIB 1,3-10 | " | SomaticNNK | AYAMT | AISGSGGSTYYADSVKG | KASSFDY | RASQSISSYLN | AASSLQS | QQSYSTPST | 9 |
| BIPA1-3,6,9 | RatBIP | PrimaryNNK | SYAMS | LISPLGKDTSYADSVKG | RAGIFDY | RASQSISSYLN | HASRLQS | QQYRLRPLT | 5 |
| BIPA4 | " | " | SYAMS | GIRRVGQATSYADSVKG | GGRLFDY | RASQSISSYLN | YASHLQS | QQYLLDPVT | 1 |
| BIPA5,7,9 | " | " | SYAMS | AINTKGMTTDYADSVKG | GSQAFDY | RASQSISSYLN | QASFLQS | QQGYNKPRT | 3 |
| BIPB1-4,6-10 | " | SomaticNNK | NYQMH | AISGSGGSTYYADSVKG | GTRRFDY | RASQSISSYLN | AASSLQS | QQSYSTPVT | 9 |
| HISA 1,2,7-8 | Bovine Histone | PrimaryNNK | SYAMS | AISPKGRRTYYADSVKG | RDKLFDY | RASQSISSYLN | EASTLQS | QQEMVPLT | 4 |
| HISA 6 | " | " | SYAMS | RITPAGRRTYYADSVKG | PSPPFDY | RASQSISSYLN | HASILQS | QQQHRPLT | 1 |
| HISA 3,9 | " | " | SYAMS | RITPAGHRTYYADSVKG | QVSRFDY | - | - | - | 2 |
| HISA 10 | " | " | SYAMS | TISPQGLRTTYADSVKG | GRPRFDY | - | - | - | 1 |
| HISA 4 | " | " | SYAMS | TISPKGRSTTYADSVKG | TNRSFDY | RASQSISSYLN | RASRLQS | QQRAKKPPT | 1 |
| HISB 1,3 | " | SomaticNNK | KYRMF | AISGSGGSTYYADSVKG | GRWPFDY | RASQSINENLS | AASSLQS | QQSYSTPHT | 2 |
| HISB 6 | " | " | RYRMH | AISGSGGSTYYADSVKG | NEPRFDY | RASQSIFMRLN | AASSLQS | QQSYSTPST | 1 |
| HISB 2 | " | " | RYRMG | AISGSGGSTYYADSVKG | GYRKFDY | RASQSISTLLN | AASSLQS | QQSYSTPLT | 1 |
| HISB 4,7,9 | " | " | RYRMG | AISGSGGSTYYADSVKG | GYRKFDY | RASQSIGPFLS | AASSLQS | QQSYSTPT | 3 |

FIG. 4A

| | | | | | | | |
|---|---|---|---|---|---|---|---|
| HISB5,8 | " | RYRMG | AISGSGGSTYYADSVKG | GYRKFDY | RASQSILRTLN | AASSLQS | QQSYSTPGT | 2 |
| NIPA2,7,10 | NIP-BSA PrimaryNNK | SYAMS | RIPARGTVTHYADSVKG | GGLRFDY | RASQSISSYLN | HASALQS | QQSYRKPTT | 3 |
| NIPA3 | " | SYAMS | GISHTGSNTRYADSVKG | RHKGFDY | RASQSISSYLN | RASTLQS | QQGYRFPAT | 1 |
| NIPA5,6,9 | " | SYAMS | RIAPEGGRTKYADSVKG | GRYWFDY | RASQSISSYLN | RASRLQS | QQSRNAPTT | 3 |
| NIPA1,8 | " | SYAMS | TISYLGEKTRYADSVKG | SRRTFDY | RASQSISSYLN | KASTLQS | QQRSRPPAT | 2 |
| NIPB1 | SomaticNNK | RYGMH | AISGSGGSTYYADSVKG | RGLGFDY | RASQSISSYLN | AASSLQS | QQSYSTPLT | 1 |
| NIPB2-4,7 | " | SYRMV | AISGSGGSTYYADSVKG | RGMAFDY | RASQSIHSRLS | HASALQS | QQSYSTPLT | 4 |
| NIPB5,6 | " | KYNMH | AISGSGGSTYYADSVKG | ARWRFDY | RASQSISSYLN | AASSLQS | QQSYSTPIT | 2 |
| NIPB8 | " | RYRMH | AISGSGGSTYYADSVKG | TPRPFDY | RASQSIQMGLS | AASSLQS | QQSYSTPNT | 1 |
| NIPB9 | " | RYRMH | AISGSGGSTYYADSVKG | TPRPFDY | RASQSISENLL | AASSLQS | QQSYSTPLT | 1 |
| 10CG1 | FITC-BSA PrimaryNNK | SYAMS | TISPYGKQTRYADSVKG | KSQHFDY | RASQSISSYLN | AASRLQS | QQRGGGPPT | 1 |
| 10CG2 | " | SYAMS | TITPRGSLTSYADSVKG | TAPPFDY | RASQSISSYLN | RASRLQS | QQSQRKPST | 1 |
| 10CG3 | " | SYAMS | GISAYGTVTYYADSVKG | RRAGFDY | RASQSISSYLN | RASRLQS | QQPRHMPQT | 1 |
| 10CG5 | " | SYAMS | SITNSGLATAYADSVKG | RSFRFDY | RASQSISSYLN | HASRLQS | QQRHTNPPT | 1 |
| 10CG6 | " | SYAMS | GITTRGQTTRYADSVKG | TYPKFDY | RASQSISSYLN | NASRLQS | QQSKLSPVT | 1 |
| 10CG7 | " | SYAMS | TIPARGHTKYADSVKG | SAKAFDY | RASQSISSYLN | QASNLQS | QQRSAGPLT | 1 |
| 10DH1 | SomaticNNK | MYRMG | AISGSGGSTYYADSVKG | RTFRFDY | RASQSIRSRLS | AASSLQS | QQSYSTPRT | 1 |
| 10DH2,3 | " | SYAMT | AISGSGGSTYYADSVKG | KTGMFDY | RASQSIRTRLR | AASSLQS | QQSYSTPRT | 2 |
| 11CG1 | Human leptin PrimaryNNK | SYAMS | AINRRGSATRYADSVKG | YLHTFDY | RASQSISSYLN | RASRLQS | QHPGLRPGT | 1 |
| 11CG2,3 | " | SYAMS | AINRRGSATRYADSVKG | YLHTFDY | RASQSISSYLN | AASALQS | QQSDLPPST | 2 |
| 11DH2 | SomaticNNK | RYRMW | AISGSGGSTYYADSVKG | RPSTFDY | RASQSIAKNLS | AASSLQS | QQSYSTPST | 1 |

FIG. 4B

| | | | | | | | * |
|---|---|---|---|---|---|---|---|
| 11DH3 | " | | RYRMW | AISGSGGSTYYADSVKG | RPSTFDY | RASQSIKQRLH | AASSLQS | QQSYSTPST | 1 |
| 12CG1,2 | Human thyroglobulin | Primary NNK | SYAMS | SIAPAGRHTYYADSVKG | NIRIFDY | RASQSISSYLN | SASRLQS | QQRAGTPVT | 2 |
| 12CG3 | " | " | SYAMS | GITMTGRTTKYADSVKG | NISMIFDY | RASQSISSYLN | QASRLQS | QQRVLRPPT | 1 |
| 12DH1,2,3 | " | Somatic NNK | RYPMS | AISGSGGSTYYADSVKG | GFYAFDY | RASQSIVRVLT | AASSLQS | QQSYSTPHT | 3 |
| 13CG1 | BSA | Primary NNK | SYAMS | TITASGPNTRYADSVKG | NHSTFDY | RASQSISSYLN | RASHLQS | QQNRTAPRT | 1 |
| 13CG2 | " | PrimaryDVT | SYAMS | TIYYAGSNTYADSVKG | GYYTFDY | RASQSISSYLN | YASNLQS | QQSDTSPIT | 1 |
| 13CG3 | " | Primary NNK | SYAMS | MIYPGGY-TKYADSVKG | NADLFDY | RASQSISSYLN | TASRLQS | QQMRRKPAT | 1 |
| 13DH1 | " | Somatic NNK | LYNMV | AISGSGGSTYYADSVKG | EWSRFDY | RASQSISKSLI | AASSLQS | QQSYSTPKT | 1 |
| 13DH2 | " | " | GYPMS | AISGSGGSTYYADSVKG | THDSFDY | RASQSIDRYLN | AASSLQS | QQSYSTPIT | 1 |
| 13DH3 | " | " | RYQMV | AISGSGGSTYYADSVKG | HLSRFDY | RASQSIKYNLA | AASSLQS | QQSYSTPRT | 1 |
| 14CG1,2,3 | Hen egg lysozyme | Primary NNK | SYAMS | EILPRGHRTAYADSVKG | SGKHFDY | RASQSISSYLN | NASTLQS | QQRKRLPET | 3 |
| 14DH2,3 | " | Somatic NNK | YYEML | AISGSGGSTYYADSVKG | PFMSFDY | RASQSIHQDLV | AASSLQS | QQSYSTPRT | 2 |
| 19CG1,3 | Mouse IgG | Primary DVT | SYAMS | SIGSSGYGTGYADSVKG | GYYSFDY | RASQSISSYLN | DASSLQS | QQSDSSPYT | 2 |
| 19DH2 | " | Somatic DVT | DYDMS | AISGSGGSTYYADSVKG | DGAGFDY | RASQSIGSSLS | AASSLQS | QQSYSTPNT | 1 |
| 20CG1 | Human IgG | Primary NNK | SYAMS | AISGLGKQTRYADSVKG | GYSRFDY | RASQSISSYLN | SASLLQS | QQLGTPPRT | 1 |
| 20DH1 | " | Somatic NNK | RYEMS | AISGSGGSTYYADSVKG | SWTLFDY | RASQSIFTNLD | AASSLQS | QQSYSTPPT | 1 |
| 20DH2 | " | " | RYEMS | AISGSGGSTYYADSVKG | SWTLFDY | RASQSIGTLLR | AASSLQS | QQSYSTPNT | 1 |

FIG. 4C

* of clone sequenced

METHODS FOR SELECTING FUNCTIONAL POLYPEPTIDES

RELATED APPLICATIONS

This application claims priority under 35 U.S.C. 119(e) to U.S. Provisional Application Serial No. 60/065,428 filed Nov. 13, 1997 and U.S. Provisional Application Serial No. 60/066,729, the entireties of which are incorporated by reference herein. The application is a Continuation-in-part of PCT application PCT/GB98/03135, filed October 20, 1998, under 35 U.S.C. §119(a)-(d) which claims priority to GB 9722131.1, filed Oct. 20, 1997, under 35 U.S.C. §365(b) and pursuant to 35 U.S.C. §119.

FIELD OF THE INVENTION

The present invention relates to methods for selecting functional members of a repertoire of polypeptides using generic and target ligands. In particular, the invention describes a method for isolating a functional subset of a repertoire of antibody polypeptides with a generic ligand.

BACKGROUND OF THE INVENTION

The antigen binding domain of an antibody comprises two separate regions: a heavy chain variable domain ($V_H$) and a light chain variable domain ($V_L$, which can be either $V_\kappa$ or $V_\lambda$). The antigen binding site itself is formed by six polypeptide loops: three from $V_H$ domain (H1, H2 and H3) and three from $V_L$ domain (L1, L2 and L3). A diverse primary repertoire of V genes that encode the $V_H$ and $V_L$ domains is produced by the combinatorial rearrangement of gene segments. The $V_H$ gene is produced by the recombination of three gene segments, $V_H$, D and $J_H$. In humans, there are approximately 51 functional $V_H$ segments (Cook and Tomlinson, 1995, Immunol. Today, 16: 237–242), 25 functional D segments (Corbett et al., 1997, J. Mol. Biol., 268: 69) and 6 functional $J_H$ segments (Ravetch et al., 1981, Cell, 27: 583–591), depending on the haplotype. The $V_H$ segment encodes the region of the polypeptide chain which forms the first and second antigen binding loops of the $V_H$ domain (H1 and H2), while the $V_H$, D and $J_H$ segments combine to form the third antigen binding loop of the $V_H$ domain (H3). The $V_L$ gene is produced by the recombination of only two gene segments, $V_L$ and $J_L$. In humans, there are approximately 40 functional $V_\kappa$ segments (Schäble and Zachau, 1993, Biol. Chem. Hoppe-Seyler, 374: 1001–1022), 31 functional $V_\lambda$ segments (Williams et al., 1996, J. Mol. Biol., 264: 220–232; Kawasaki et al., 1997, Genome Res., 7: 250–261), 5 functional $J_\kappa$ segments (Hieter et al., 1982, J. Biol. Chem., 257: 1516) and 4 functional $J_\lambda$ segments (Vasicek and Leder, 1990, J. Exp. Med., 172: 609–620), depending on the haplotype. The $V_L$ segment encodes the region of the polypeptide chain which forms the first and second antigen binding loops of the $V_L$ domain (L1 and L2), while the $V_L$ and $J_L$ segments combine to form the third antigen binding loop of the $V_L$ domain (L3). Antibodies selected from this primary repertoire are believed to be sufficiently diverse to bind almost all antigens with at least moderate affinity. High affinity antibodies are produced by "affinity maturation" of the rearranged genes, in which point mutations are generated and selected by the immune system on the basis of improved binding.

Analysis of the structures and sequences of antibodies has shown that five of the six antigen binding loops (H1, H2, L1, L2, L3) possess a limited number of main-chain conformations or canonical structures (Chothia and Lesk, 1987, J. Mol. Biol., 196: 901–917; Chothia et al., 1989, Nature, 342: 877–883). The main-chain conformations are determined by (i) the length of the antigen binding loop, and (ii) particular residues, or types of residue, at certain key position in the antigen binding loop and the antibody framework. Analysis of the loop lengths and key residues has enabled us to the predict the main-chain conformations of H1, H2, L1, L2 and L3 encoded by the majority of human antibody sequences (Chothia et al., 1992, J. Mol. Biol., 227: 799–817; Tomlinson et al., 1995, EMBO J., 14: 4628–4638; Williams et al., 1996, supra). Although the H3 region is much more diverse in terms of sequence, length and structure (due to the use of D segments), it also forms a limited number of main-chain conformations for short loop lengths which depend on the length and the presence of particular residues, or types of residue, at key positions in the loop and the antibody framework (Martin et al., 1996, J. Mol. Biol.,263: 800–815; Shirai et al., 1996, FEBS Letters, 399: 1–8).

A similar analysis of side-chain diversity in human antibody sequences has enabled the separation of the pattern of sequence diversity in the primary repertoire from that created by somatic hypermutation. The two patterns are complementary: diversity in the primary repertoire is focused at the center of the antigen binding whereas somatic hypermutation spreads diversity to regions at the periphery that are highly conserved in the primary repertoire (Tomlinson et al., 1996, J. Mol. Biol, 256: 813–817; Ignatovich et al., 1997, J. Mol. Biol., 268: 69–77). This complementarity seems to have evolved as an efficient strategy for searching sequence space, given the limited number of B cells available for selection an a given time. Thus, antibodies are first selected from the primary repertoire based on diversity at the centre of the binding site. Somatic hypermutation is then left to optimize residues at the periphery without disrupting favorable interactions established during the primary response.

The recent advent of phage-display technology (Smith, 1985, Science, 228: 1315–1317; Scott and Smith, 1990, Science, 249: 386–390; McCafferty et al., 1990, Nature, 348: 552–554) has enabled the in vitro selection of human antibodies against a wide range of target antigens from "single pot" libraries. These phage-antibody libraries can be grouped into two categories: natural libraries which use rearranged V genes harvested from human B cells (Marks et al., 1991, J. Mol. Biol., 222: 581–597; Vaughan et al., 1996, Nature Biotech., 14: 309) or synthetic libraries whereby germline V gene segments are 'rearranged' in vitro (Hoogenboom and Winter, 1992, J. Mol. Biol., 227: 381–388; Nissim et al., 1994, EMBO J., 13: 692–698; Griffiths et al., 1994, EMBO J., 13: 3245–3260; De Kruif et al., 1995, J. Mol. Biol., 248: 97) or where synthetic CDRs are incorporated into a single rearranged V gene (Barbas et al., 1992, Proc. Natl. Acad. Sci. USA, 89: 4457–4461). Although synthetic libraries help to overcome the inherent biases of the natural repertoire which can limit the effective size of phage libraries constructed from rearranged V genes, they require the use of long degenerate PCR primers which frequently introduce base-pair deletions into the assembled V genes. This high degree of randomization may also lead to the creation of antibodies which are unable to fold correctly and are also therefore non-functional. Furthermore, antibodies selected from these libraries may be poorly expressed and, in many cases, will contain framework mutations that may effect the antibodies immunogenicity when used in human therapy.

Recently, in an extension of the synthetic library approach it has been suggested (WO97/08320, Morphosys) that human antibody frameworks can be pre-optimized by synthesizing a set of 'master genes' that have consensus framework sequences and incorporate amino acid substitutions shown to improve folding and expression. Diversity in the CDRs is then incorporated using oligonucleotides. Since it is desirable to produce artificial human antibodies which will not be recognized as foreign by the human immune system, the use of consensus frameworks which, in most cases, do not correspond to any natural framework is a disadvantage of this approach. Furthermore, since it is likely that the CDR diversity will also have an effect on folding and/or expression, it would be preferable to optimize the folding and/or expression (and remove any frame-shifts or stop codons) after the V gene has been fully assembled. To this end, it would be desirable to have a selection system which could eliminate non-functional or poorly folded/ expressed members of the library before selection with the target antigen is carried out.

A further problem with the libraries of the prior art is that, because the main-chain conformation is heterogeneous, three-dimensional structural modeling is difficult because suitable high resolution crystallographic data may not be available. This is a particular problem for the H3 region, where the vast majority of antibodies derived from natural or synthetic have medium length or long loops and therefore cannot be modeled.

SUMMARY OF THE INVENTION

According to the first aspect of the present invention, there is provided a method for selecting, from a repertoire of polypeptides, a population of functional polypeptides which bind a target ligand in a first binding site and a generic ligand in a second binding site, which generic ligand is capable of binding functional members of the repertoire regardless of target ligand specificity, comprising the steps of:

a) contacting the repertoire with the generic ligand and selecting functional polypeptides bound thereto; and b) contacting the selected functional polypeptides with the target ligand and selecting a population of polypeptides which bind to the target ligand.

The invention accordingly provides a method by which a repertoire of polypeptides is preselected, according to functionality as determined by the ability to bind the generic ligand, and the subset of polypeptides obtained as a result of preselection is then employed for further rounds of selection according to the ability to bind the target ligand. Although, in a preferred embodiment, the repertoire is first selected with the generic ligand, it will be apparent to one skilled in the art that the repertoire may be contacted with the ligands in the opposite order, i.e. with the target ligand before the generic ligand.

The invention permits the person skilled in the art to remove, from a chosen repertoire of polypeptides, those polypeptides which are non-functional, for example as a result of the introduction of frame-shift mutations, stop codons, folding mutants or expression mutants which are incapable of binding to a target ligand. Such non-functional mutants are generated by the normal randomization and variation procedures employed in the construction of polypeptide repertoires. At the same time the invention permits the person skilled in the art to enrich a chosen repertoire of polypeptides for those polypeptides which are functional, well folded and highly expressed.

Preferably, two or more subsets of polypeptides are obtained from a repertoire by the method of the invention, for example, by prescreening the repertoire with two or more generic ligands, or by contacting the repertoire with the generic ligand(s) under different conditions. Advantageously, the subsets of polypeptides thus obtained are combined to form a further repertoire of polypeptides, which may be further screened by contacting with target and/or generic ligands.

Preferably, the library according to the invention comprises polypeptides of the immunoglobulin superfamily, such as antibody polypeptides or T-cell receptor polypeptides. Advantageously, the library may comprise individual immunoglobulin domains, such as the $V_H$ or $V_L$ domains of antibodies, or the $V_\beta$ or $V_\alpha$ domains of T-cell receptors. In a preferred embodiment, therefore, repertoires of, for example, $V_H$ and $V_L$ polypeptides may be individually prescreened using a generic ligand and then combined to produce a functional repertoire comprising both $V_H$ and $V_L$ polypeptides. Such a repertoire can then be screened with a target ligand in order to isolate polypeptides comprising both $V_H$ and $V_L$ domains and having the desired binding specificity.

In an advantageous embodiment, the generic ligand selected for use with immunoglobulin repertoires is a superantigen. Superantigens are able to bind to functional immunoglobulin molecules, or subsets thereof comprising particular main-chain conformations, irrespective of target ligand specificity. Alternatively, generic ligands may be selected from any ligand capable of binding to the general structure of the polypeptides which make up any given repertoire, such as antibodies themselves, metal ion matrices, organic compounds including proteins or peptides, and the like.

In a second aspect, the invention provides a library wherein the functional members have binding sites for both generic and target ligands. Libraries may be specifically designed for this purpose, for example by constructing antibody libraries having a main-chain conformation which is recognized by a given superantigen, or by constructing a library in which substantially all potentially functional members possess a structure recognizable by a antibody ligand.

In a third aspect, the invention provides a method for detecting, immobilizing, purifying or immunoprecipitating one or more members of a repertoire of polypeptides previously selected according to the invention, comprising binding the members to the generic ligand.

In a fourth aspect, the invention provides a library comprising a repertoire of polypeptides of the immunoglobulin superfamily, wherein the members of the repertoire have a known main-chain conformation.

In a fifth aspect, the invention provides a method for selecting a polypeptide having a desired generic and/or target ligand binding site from a repertoire of polypeptides, comprising the steps of:

a) expressing a library according to the preceding aspects of the invention;

b) contacting the polypeptides with generic and/or target ligands and selecting those which bind the generic and/or target ligand; and c) optionally amplifying the selected polypeptide(s) which bind the generic and/or target ligand.

d) optionally repeating steps a)-c).

Repertoires of polypeptides are advantageously both generated and maintained in the form of a nucleic acid library. Therefore, in a sixth aspect, the invention provides a nucleic acid library encoding a repertoire of such polypeptides.

As used herein, the term "repertoire" refers to a heterogeneous population of molecules, for example nucleic acid molecules which vary in nucleotide sequence or polypeptide molecules which vary in amino acid sequence. A library according to the invention will encompass a repertoire of polypeptides or nucleic acids. According to the present invention, a repertoire of polypeptides is designed to possess a binding site for a generic ligand and a binding site for a target ligand. The binding sites may overlap, or be located in the same region of the molecule, but their specificities will differ.

As used herein with regard to the generic ligand, the term "select" refers to binding of the generic ligand to its binding site on library members, to exclude non-functional library members (such as those bearing frameshift-, stop-codon- (nonsense) or substitution (missense) mutations, or any other mutations which render them unable to fold properly and/or or bind the target ligand. Similarly, when used with regard to the target ligand, the term "select" refers to binding of the generic ligand to polypeptides which possess a functional target-ligand-binding site, such that non-functional library members are lost. Together, retention of library members which bind the generic and target ligands is referred to as selection from a functional polypeptide repertoire of a subset of repertoire members.

As used herein, the term "organism" refers to all cellular life-forms, such as prokaryotes and eukaryotes, as well as non-cellular, nucleic acid-containing entities, such as bacteriophage and viruses.

As used herein, the term "functional" refers to a polypeptide which possesses either the native biological activity of the naturally-produced proteins of its type, or any specific desired activity, for example as judged by its ability to bind to ligand molecules, defined below. Examples of "functional" polypeptides include an antibody binding specifically to an antigen through its antigen-binding site, a receptor molecule (e.g. a T-cell receptor) binding its characteristic ligand and an enzyme binding to its substrate. In order for a polypeptide to be classified as functional according to the invention, it follows that it first must be properly processed and folded so as to retain its overall structural integrity, as judged by its ability to bind the generic ligand, also defined below.

For the avoidance of doubt, functionality is not equivalent to the ability to bind the target ligand. For instance, a functional anti-CEA monoclonal antibody will not be able to bind specifically to target ligands such as bacterial LPS. However, because it is capable of binding a target ligand (i.e. it would be able bind to CEA if CEA were the target ligand) it is classed as a "functional" antibody molecule and may be selected by binding to a generic ligand, as defined below. Typically, non-functional antibody molecules will be incapable of binding to any target ligand.

As used herein, the term "generic ligand" refers to a ligand that binds a substantial proportion of functional members in a given repertoire. Thus, the same generic ligand can bind many members of the repertoire regardless of their target ligand specificities (see below). In general, the presence of functional generic ligand binding site indicates that the repertoire member is expressed and folded correctly. Thus, binding of the generic ligand to its binding site provides a method for preselecting functional polypeptides from a repertoire of polypeptides.

As used herein, the term "target ligand" refers to a ligand for which a specific binding member or members of the repertoire is to be identified and/or isolated. Where the members of the repertoire are antibody molecules, the target ligand may be an antigen and where the members of the repertoire are enzymes, the target ligand may be a substrate. Binding to the target ligand is dependent upon both the member of the repertoire being functional, as described above under generic ligand, and upon the precise specificity of the binding site for the target ligand.

As used herein, the term "subset" refers to a part of a repertoire. In the terms of the present invention, it is often the case that only a subset of the repertoire is functional and therefore possesses a functional generic ligand binding site. Furthermore, it is also possible that only a fraction of the functional members of a repertoire (yet significantly more than would bind a given target ligand) will bind the generic ligand. These subsets are able to be selected according to the invention. Subsets of a library may be combined or pooled to produce novel repertoires which have been preselected according to desired criteria. Combined or pooled repertoires may be simple mixtures of the polypeptide members preselected by generic ligand binding, or may be manipulated to combine two polypeptide subsets. For example, $V_H$ and $V_L$ polypeptides may be individually prescreened, and subsequently combined at the genetic level onto single vectors such that they are expressed as combined $V_H$-$V_L$ dimers, such as scFv.

As used herein, the term "library" refers to a mixture of heterogeneous polypeptides or nucleic acids. A library is composed of members, which have a single polypeptide or nucleic acid sequence. To this extent, "library" is synonymous with "repertoire". Sequence differences between library members are responsible for the diversity present in the library. The library may take the form of a simple mixture of polypeptides or nucleic acids, or may be in the form organisms or cells, for example bacteria, viruses, animal or plant cells and the like, transformed with a library of nucleic acids. Preferably, each individual organism or cell contains only one member of the library. Advantageously, the nucleic acids are incorporated into expression vectors, in order to allow expression of the polypeptides encoded by the nucleic acids. In a preferred aspect, therefore, a library may take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of genetically diverse polypeptide variants.

As used herein, the term "immunoglobulin superfamily" refers to a family of polypeptides which retain the immunoglobulin fold characteristic of immunoglobulin (antibody) molecules, which contains two β sheets and, usually, a conserved disulfide bond. Members of the immunoglobulin superfamily are involved in many aspects of cellular and non-cellular interactions in vivo, including widespread roles in the immune system (for example, antibodies, T-cell receptor molecules and the like), involvement in cell adhesion (for example the ICAM molecules) and intracellular signaling (for example, receptor molecules, such as the PDGF receptor). The present invention is applicable to all immunoglobulin superfamily molecules, since variation therein is achieved in similar ways. Preferably, the present invention relates to immunoglobulins (antibodies).

As used herein, the term "main-chain conformation" refers to the Cα backbone trace of a structure in three-dimensions. When individual hypervariable loops of antibodies or TCR molecules are considered the main-chain conformation is synonymous with the canonical structure. As set forth in Chothia and Lesk, 1987 *J. Mol. Biol.*, 196: 901 and Chothia et al., 1989 *Nature*, 342: 877, antibodies display a limited number of canonical structures for five of their six hypervariable loops (H1, H2, L1, L2 and L3), despite considerable side-chain diversity in the loops themselves. The precise canonical structure exhibited depends on the length of the loop and the identity of certain key residues involved in its packing. The sixth loop (H3) is much more diverse in both length and sequence and therefore only exhibits canonical structures for certain short loop lengths (Martin et al., 1996 *J. Mol. Biol.*, 263: 800; Shirai et al., 1996 *FEBS Letters*, 399: 1). In the present invention, all six loops will preferably have canonical structures and hence the main-chain conformation for the entire antibody molecule will be known.

As used herein, the term "antibody" refers to an immunoglobulin that is produced by a B cell and which forms a central part of the host immune defense system in vertebrates. An "antibody polypeptide", as used herein, is a polypeptide which either is an antibody or is a part of an antibody, modified or unmodified. Thus, the term antibody polypeptide includes a heavy chain, a light chain, a heavy chain-light chain dimer, a Fab fragment, a F(ab')2 fragment, a Dab fragment, or an Fv fragment, including a single chain Fv (scFv). Methods for the construction of such antibody molecules are well known in the art.

As used herein, the term "superantigen" refers to an antigen, typically in the form of a toxin expressed in bacteria, which interacts with members of the immunoglobulin superfamily outside the conventional ligand binding sites for these molecules. Staphylococcal enterotoxins interact with T-cell receptors and have the effect of stimulating CD4+ T-cells. Superantigens for antibodies include the molecules Protein G that binds the IgG constant region (Bjorck and Kronvall, 1984, *J. Immunol*, 133: 969; Reis et al., 1984, J. Immunol., 132: 3091), Protein A that binds the IgG constant region and the $V_H$ domain (Forsgren and Sjoquist, 1966, *J. Immunol.*, 97: 822) and Protein L that binds the $V_L$ domain (Bjorck, 1988, *J. Immunol.*, 140: 1994).

As used herein, the term "detecting" refers to binding to a member polypeptide of a repertoire a labeled probe comprising a generic- and/or target ligand of the invention, and then performing a step to determine the presence or absence of label, the former of which is indicative of the presence in a sample of the member polypeptide of interest.

As used herein, the term "immobilizing" refers to indirect binding a member polypeptide of a repertoire of polypeptides to a solid or semi-solid support, via binding the target- and/or generic ligand of the invention, either of which specifically binds the polypeptide member and is, itself, linked to the support.

As used herein, the term "purifying" refers to the isolation of a polypeptide from a repertoire of polypeptides according to the invention away from polypeptides of unlike sequence. Such purifying may be accomplished, for example, via immunoprecipitation or affinity chromatography, using one or both of the target and generic ligands.

As used herein, the term "immunoprecipitating" refers to contacting a repertoire of polypeptide molecules with an antibody under conditions which permit the formation of specific antibody:antigen complexes and under which such complexes precipitate from solution, collecting the precipitate and resuspending the precipitated proteins in a buffer which permits dissociation of the antibody from the antigen. In the case of the present invention, immunoprecipitation may be performed using an a generic- and/or a target ligand which is an antibody.

BRIEF DESCRIPTION OF THE DRAWINGS

FIG. 2 presents the sequence of the scFv (DNA (SEQ ID NO. 1), corresponding amino acids (SEQ IB NO. 2)) that forms the basis of a library according to the invention. There are currently two versions of the library: a "primary" library wherein 18 positions are varied and a "somatic" library wherein 12 positions are varied. The six loop regions H1, H2, H3, L1, L2 and L3 are indicated. CDR regions as defined by Kabat (Kabat et al., 1991, Sequences of proteins of immunological interest, U.S. Department of Health and Human Services) are underlined.

FIG. 3 shows an analysis of functionality in a library according to the invention before and after selecting with the generic ligands Protein A and Protein L. Here Protein L is coated on an ELISA plate, the scFv supernatants are bound to it and detection of scFv binding is with Protein A-HRP. Therefore, only those scFv capable of binding both Protein A and Protein L give an ELISA signal.

FIGS. 4a–4e present sequences of clones selected from libraries according to the invention, after panning with bovine ubiquitin, rat BIP, bovine histone, NIP-BSA, FITC-BSA, human leptin, human thyroglobulin, BSA, hen egg lysozyme, mouse IgG and human IgG. Underlines in the sequences indicate the positions which were varied in the respective libraries.

DETAILED DESCRIPTION OF THE INVENTION

Figure 1:
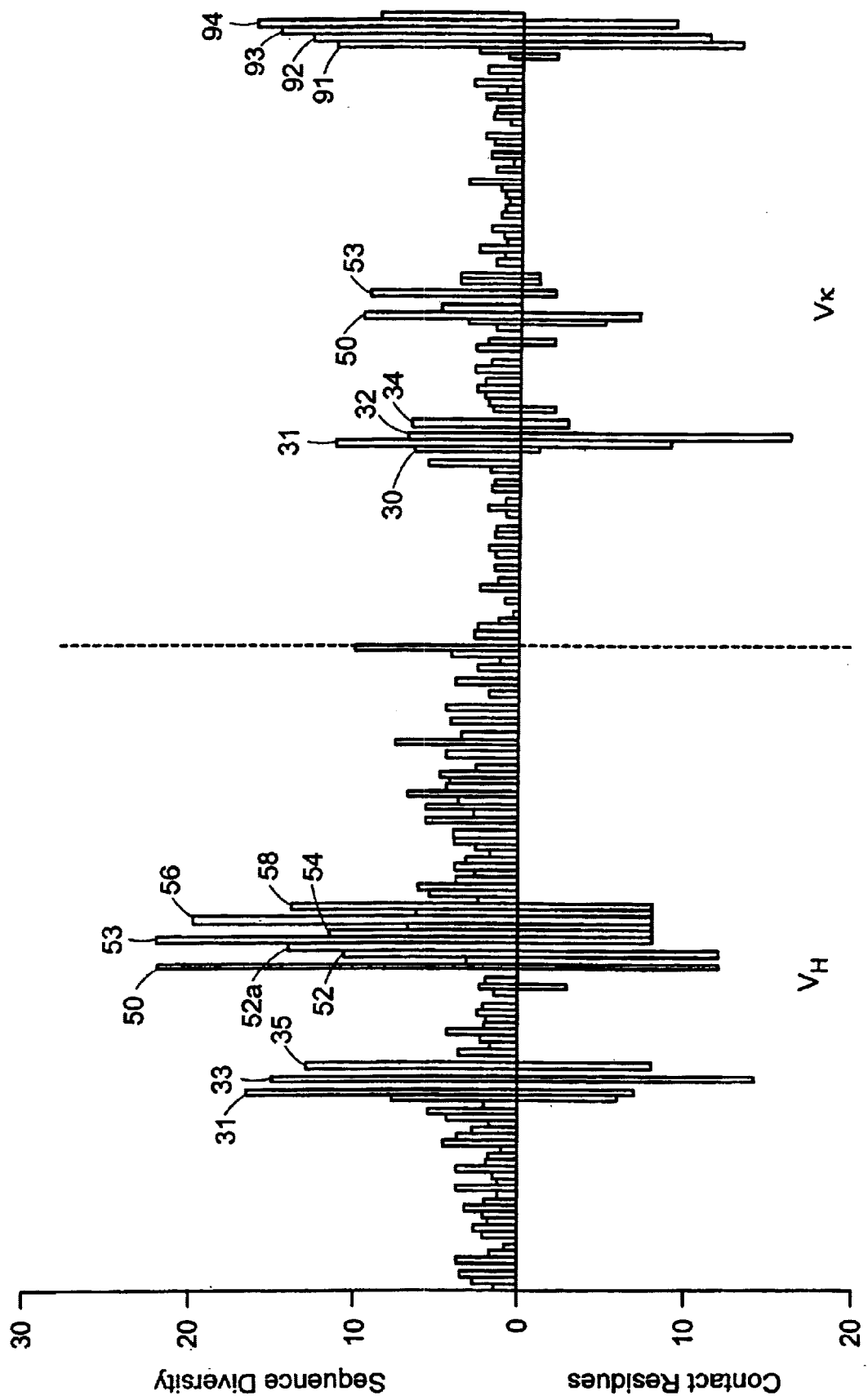
FIG. 1 depicts a bar graph indicating positions in the $V_H$ and $V_\kappa$ regions of the human antibody repertoire which exhibit extensive natural diversity and make antigen contacts (see Tomlinson et al., 1996, *J. Mol. Biol.*, 256: 813). The H3 and the end of L3 are not shown in this representation although they are also highly diverse and make antigen contacts. Although sequence diversity in the human lambda genes has been thoroughly characterized (see Ignatovich et al., 1997, *J. Mol. Biol.*, 268: 69) very little data on antigen contacts currently exists for three-dimensional lambda structures.

The present invention provides a selection system which eliminates (or significantly reduces the proportion of) non-functional or poorly folded/expressed members of a polypeptide library while enriching for functional, folded and well expressed members before a selection for specificity against a "target ligand" is carried out. A repertoire of polypeptide molecules is contacted with a "generic ligand", a protein that has affinity for a structural feature common to all functional, for example complete and/or correctly folded, proteins of the relevant class. The term "ligand" is used broadly in reference to molecules of use in the present invention. As used herein, the term "ligand" refers to an entity that will bind to or be bound by a member of the polypeptide library.

A significant number of defective proteins present in the initial repertoire fail to bind the generic ligand and are thereby eliminated. This selective removal of non-functional polypeptides from a library results in a marked reduction in its actual size, while its functional size is maintained, with a corresponding increase in its quality. Polypeptides which are retained by virtue of binding the generic ligand constitute a 'first selected pool' or 'subset' of the original repertoire. Consequently, this 'subset' is enriched for functional, well folded and well expressed members of the initial repertoire.

The polypeptides of the first selected pool or subset are subsequently contacted with at least one "target ligand", which binds to polypeptides with a given functional specificity. Such target ligands include, but are not limited to, either half of a receptor/ligand pair (e.g. a hormone or other cell-signaling molecule, such as a neurotransmitter, and its cognate receptor), either of a binding pair of cell adhesion molecules, a protein substrate that is bound by the active site of an enzyme, a protein, peptide or small organic compound against which a particular antibody is to be directed or even an antibody itself. Consequently, the use of such a library is less labor-intensive and more economical, in terms of both time and materials, than is that of a conventional library. In addition, since, compared to a repertoire which has not been selected with a generic ligand, the first selected pool will contain a much higher ratio of molecules able to bind the target ligand to those that are unable to bind the target ligand, there will be a significant reduction of background during selection with the "target ligand".

Combinatorial selection schemes are also contemplated according to the invention. Multiple selections of the same initial polypeptide repertoire can be performed in parallel or in series using different generic and/or target ligands. Thus, the repertoire can first be selected with a single generic ligand and then subsequently selected in parallel using different target ligands. The resulting subsets can then be used separately or combined, in which case the combined subset will have a range of target ligand specificities but a single generic ligand specificity. Alternatively, the repertoire can first be selected with a single target ligand and then subsequently selected in parallel using different generic ligands. The resulting subsets can then be used separately or combined, in which case the combined subset will have a range of generic ligand specificities but a single target ligand specificity. The use of more elaborate schemes are also envisaged. For example, the initial repertoire can be subjected to two rounds of selection using two different generic ligands, followed by selection with the target ligand. This produces a subset in which all members bind both generic ligands and the target ligand. Alternatively, if the selection of the initial repertoire with the two generic ligands is performed in parallel and the resulting subsets combined and then selected with the target ligand the resulting subset binds at least one of the two generic ligands and the target ligand. Combined or pooled repertoires may be simple mixtures of the subsets or may be manipulated to physically link the subsets. For example, $V_H$ and $V_L$ polypeptides may be individually selected in parallel by binding two different generic ligands, and subsequently combined at the genetic level onto single vectors such that they are expressed as combined $V_H$-$V_L$. This repertoire can then be selected against the target ligand such that the selected members able to bind both generic ligands and the target ligand.

The invention encompasses libraries of functional polypeptides selected or selectable by the methods broadly described above, as well as nucleic acid libraries encoding polypeptide molecules which may be used in a selection performed according to these methods (preferably, molecules which comprise a first binding site for a target ligand and a second binding site for a generic ligand). In addition, the invention provides methods for detecting, immobilizing, purifying or immunoprecipitating one or more members of a repertoire of functional polypeptides selected using the generic or target ligands according to the invention.

The invention is particularly applicable to the enrichment of libraries of molecules of the immunoglobulin superfamily. This is particularly true as regards the generation of populations of antibodies and T-cell receptors which are functional and have a desired specificity, as is required for use in diagnostic, therapeutic or prophylactic procedures. To this end, the invention provides antibody and T-cell receptor libraries wherein all the members have both natural frameworks and loops of known main-chain conformation, as well as strategies for useful mutagenesis of the starting sequence and the subsequent selection of functional variants so generated. Such polypeptide libraries may comprise $V_H$ or $V_\beta$ domains or, alternatively, it may comprise $V_L$ or $V_\alpha$ domains, or even both $V_H$ or $V_\beta$ and $V_L$ or $V_\alpha$ domains.

There is significant need in the art for improved libraries of antibody or T-cell receptor molecules. For example, despite progress in the creation of "single pot" phage-antibody libraries, several problems still remain. Natural libraries (Marks et al., 1991, *J. Mol. Biol.,* 222: 581; Vaughan et al., 1996, *Nature Biotech.,* 14: 309) which use rearranged V genes harvested from human B cells are highly biased due to the positive and negative selection of the B cells in vivo. This can limit the effective size of phage libraries constructed from rearranged V genes. In addition, clones derived from natural libraries invariably contain framework mutations which may effect the antibodies immunogenicity when used in human therapy. Synthetic libraries (Hoogenboom and Winter, 1992 *J. Mol. Biol.,* 227: 381; Barbas et al., 1992, *Proc. Natl. Acad. Sci. USA,* 89: 4457; Nissim et al., 1994, *EMBO J.,* 13: 692; Griffiths et al., 1994, *EMBO J.,* 13: 3245; De Kruif et al., 1995, *J. Mol. Biol.,* 248: 97) can overcome the problem of bias but they require the use of long degenerate PCR primers which frequently introduce base-pair deletions into the assembled V genes. This high degree of randomization may also lead to the creation of antibodies which are unable to fold correctly and are also therefore non-functional. In many cases it is likely that these non-functional members will outnumber the functional members in a library. Even if the frameworks can be pre-optimized for folding and/or expression (WO97/08320, Morphosys) by synthesizing a set of 'master genes' with consensus framework sequences and by incorporating amino acid substitutions shown to improve folding and expression, there remains the problem of immunogenicity since, in most cases, the consensus sequences do not correspond to any natural framework. Furthermore, since it is likely that the CDR diversity will also have an effect of folding and/or expression, it is preferable to optimize the folding and/or expression (and remove any frame-shifts or stop codons) after the V gene has been fully assembled.

A further problem with existing libraries is that because the main-chain conformation is heterogeneous, three-dimensional structural modeling is difficult because suitable high resolution crystallographic data may not be available. This is a particular problem for the H3 region, where the vast majority of antibodies derived from natural or synthetic antibody libraries have medium length or long loops and therefore cannot be modeled.

Another problem with existing libraries is the reliance on epitope tags (such as the myc, FLAG or HIS tags) for detection of expressed antibody fragments. As these are usually located at the N or C terminal ends of the antibody fragment they tend to be prone to proteolytic cleavage. Superantigens, such as Protein A and Protein L can be used to detect expressed antibody fragments by binding the folded domains themselves but since they are $V_H$ and $V_L$ family specific, only a relatively small proportion of members of any existing antibody library will bind one of these reagents and an even smaller proportion will bind to both.

To this end, it would be desirable to have a selection system which could eliminate (or at least reduce the proportion of) non-functional or poorly folded/expressed members of the library before selection against the target antigen is carried out while enriching for functional, folded and well expressed members all of which are able to bind generic ligands such as the superantigens Protein A and Protein L. In addition, it would be advantageous to construct an antibody library wherein all the members have natural frameworks and have loops with known main-chain conformations.

The invention accordingly provides a method by which a polypeptide repertoire may be selected to remove non-functional members. This results in a marked reduction in the actual library size (and a corresponding increase in the quality of the library) without reducing the functional library size. The invention also provides a method for creating new polypeptide repertoires wherein all the functional members are able to bind a given generic ligand. The same generic ligand can be used for the subsequent detection, immobilization, purification or immunoprecipitation of any one or more members of the repertoire.

Any 'naïve' or 'immune' antibody repertoire can be used with the present invention to enrich for functional members and/or to enrich for members that bind a given generic ligand or ligands. Indeed, since only a small percentage of all human germline $V_H$ segments bind Protein A with high affinity and only a small percentage of all human germline $V_L$ segments bind Protein L with high affinity preselection with these superantigens is highly advantageous. Alternatively, pre-selection with via the epitope tag enables non-functional variants to be removed from synthetic libraries. The libraries that are amenable to preselection include, but are not limited to, libraries comprised of V genes rearranged in vivo of the type described by Marks et al., 1991, *J. Mol. Biol.*, 222: 581 and Vaughan et al., 1996, *Nature Biotech.*, 14: 309, synthetic libraries whereby germline V gene segments are 'rearranged' in vitro (Hoogenboom & Winter, 1992, *J. Mol. Biol.*, 227: 381; Nissim et al., 1994 *EMBO J.*, 13: 692; Griffiths et al., 1994, EMBO J., 13: 3245; De Kruifet al., 1995, *J. Mol. Biol.*, 248: 97) or where synthetic CDRs are incorporated into a single rearranged V gene (Barbas et al., 1992, *Proc. Natl. Acad. Sci. USA*, 89: 4457) or into multiple master frameworks (WO97/08320, Morphosys).

Selection of Polypeptides According to the Invention

Once a diverse pool of polypeptides is generated, selection according to the invention is applied. Two broad selection procedures are based upon the order in which the generic and target ligands are applied; combinatorial variations on these schemes involve the use of multiple generic and/or target ligands in a given step of a selection. When a combinatorial scheme is used, the pool of polypeptide molecules may be contacted with, for example, several target ligands at once, or by each singly, in series; in the latter case, the resulting selected pools of polypeptides may be kept separate or may, themselves, be pooled. These selection schemes may be summarized as follows:

a. Selection Procedure 1:

Initial Polypeptide Selection Using the Generic Ligand

In order to remove non-functional members of the library, a generic ligand is selected, such that the generic ligand is only bound by functional molecules. For example, the generic ligand may be a metallic ion, an antibody (in the form of a monoclonal antibody or a polyclonal mixture of antibodies), half of an enzyme/ligand complex or organic material; note that ligands of any of these types are, additionally or alternatively, of use as target ligands according to the invention. Antibody production and metal affinity chromatography are discussed in detail below. Ideally, these ligands bind a site (e.g., a peptide tag or superantigen binding site) on the members of the library which is of constant structure or sequence, which structure is liable to be absent or altered in non-functional members. In the case of antibody libraries, this method is of use to select from a library only those functional members which have a binding site for a given superantigen or monoclonal antibody; such an approach is useful in selecting functional antibody polypeptides from both natural and synthetic pools thereof.

The superantigens Protein A and/or Protein L are of use in the invention as generic ligands to select antibody repertoires, since they bind correctly folded $V_H$ and $V_L$ domains (which belong to certain $V_H$ and $V_L$ families), respectively, regardless of the sequence and structure of the binding site for the target ligand. In addition, Protein A or another superantigen Protein G are of use as generic ligands to select for folding and/or expression by binding the heavy chain constant domains of antibodies. Anti-κ and anti-λ antibodies are also of use in selecting light chain constant domains. Small organic mimetics of antibodies or of other binding proteins, such as Protein A (Li et al., 1998, *Nature Biotechnology*, 16: 190), are also of use.

When this selection procedure is used, the generic ligand, by its very nature, is able to bind all functional members of the preselected repertoire; therefore, this generic ligand (or some conjugate thereof) may be used to detect, immobilize, purify or immunoprecipitate any member or population of members from the repertoire (whether selected by binding a given target ligand or not, as discussed below). Protein detection via immunoassay techniques as well as immunoprecipitation of member polypeptides of a repertoire of the invention may be performed by the techniques discussed below with regard to the testing of antibody selection ligands of use in the invention (see "Antibodies for use as ligands in polypeptide selection"). Immobilization may be performed through specific binding of a polypeptide member of a repertoire to either a generic or target ligand according to the invention which is, itself, linked to a solid or semi-solid support, such as a filter (e.g., of nitrocellulose or nylon) or a chromatographic support (including, but not limited to, a cellulose, polymer, resin or silica support); covalent attachment of the member polypeptide to the generic or target ligand may be performed using any of a number of chemical crosslinking agents known to one of skill in the art. Immobilization on a metal affinity chromatography support is described below (see "Metallic ligands as use for the selection of polypeptides"). Purification may comprise any or a combination of these techniques, in particular immunoprecipitation and chromatography by methods well known in the art.

Using this approach, selection with multiple generic ligands can be performed either one after another to create a repertoire in which members bind two or more generic ligands, separately in parallel, such that the subsets can then be combined (in this case, members of the preselected repertoire will bind at least one of the generic ligands) or separately followed by incorporation into the same polypeptide chain whereby a large functional library in which members may be able to bind all the generic ligands used during preselection. For example, subsets can be selected from one or more libraries using different generic ligands which bind heavy and light chains of antibody molecules (see below) and then combined to form a heavy/light chain library, in which the heavy and light chains are either non-covalently associated or are covalently linked, for example, by using $V_H$ and $V_L$ domains in a single-chain Fv context.

Secondary Polypeptide Selection Using the Target Ligand

Following the selection step with the generic ligand, the library is screened in order to identify members that bind to the target ligand. Since it is enriched for functional polypeptides after selection with the generic ligand, there will be an advantageous reduction in non-specific ("background") binding during selection with the target ligand. Furthermore, since selection with the generic ligand produces a the marked reduction in the actual library size (and a corresponding increase in the quality of the library) without reducing the functional library size, a smaller repertoire should elicit the same diversity of target ligand specificities and affinities as the larger starting repertoire (that contained many non-functional and poorly folded/expressed members).

One or more target ligands may be used to select polypeptides from the first selected polypeptide pool generated using the generic ligand. In the event that two or more target ligands are used to generate a number of different subsets, two or more of these subsets may be combined to form a single, more complex subset. A single generic ligand is able to bind every member of the resulting combined subset; however, a given target ligand binds only a subset of library members.

b. Selection Procedure 2:

Initial Selection of Repertoire Members with the Target Ligand

Here, selection using the target ligand is performed prior to selection using the generic ligand. Obviously, the same set of polypeptides can result from either scheme, if such a result is desired. Using this approach, selection with multiple target ligands can be performed in parallel or by mixing the target ligands for selection. If performed in parallel, the resulting subsets may, if required, be combined.

Secondary Polypeptide Selection Using the Generic Ligand

Subsequent selection of the target ligand binding subset can then be performed using one or more generic ligands. While this is not a selection for function, since members of the repertoire that are able to bind to the target ligand are by definition functional, it does enable subsets that bind to different generic ligands to be isolated. Thus, the target ligand selected population can be selected by one generic ligand or by two or more generic ligands. In this case, the generic ligands can be used one after another to create a repertoire in which all members bind the target ligand and two or more generic ligands or separately in parallel, such that different (but possibly overlapping) subsets binding the target ligand and different generic ligands are created. These can then be combined (in this case, members will bind at least one of the generic ligands).

Selection of Immunoglobulin-family Polypeptide Library Members

The members of the repertoires or libraries selected in the present invention advantageously belong to the immunoglobulin superfamily of molecules, in particular, antibody polypeptides or T-cell receptor polypeptides. For antibodies, it is envisaged that the method according to this invention may be applied to any of the existing antibody libraries known in the art (whether natural or synthetic) or to antibody libraries designed specifically to be preselected with generic ligands (see below).

Construction of Libraries of the Invention a. Selection of the Main-chain Conformation The members of the immunoglobulin superfamily all share a similar fold for their polypeptide chain. For example, although antibodies are highly diverse in terms of their primary sequence, comparison of sequences and crystallographic structures has revealed that, contrary to expectation, five of the six antigen binding loops of antibodies (H1, H2, L1, L2, L3) adopt a limited number of main-chain conformations, or canonical structures (Chothia and Lesk (1987) supra; Chothia et al (1989) supra). Analysis of loop lengths and key residues has therefore enabled prediction of the main-chain conformations of H1, H2, L1, L2 and L3 found in the majority of human antibodies (Chothia et al. (1992) supra; Tomlinson et al. (1995) supra; Williams et al. (1996) supra). Although the H3 region, is much more diverse in terms of sequence, length and structure (due to the use of D segments), it also forms a limited number of main-chain conformations for short loop lengths which depend on the length and the presence of particular residues, or types of residue, at key positions in the loop and the antibody framework (Martin et al. (1996) supra; Shirai et al. (1996) supra).

According to the present invention, libraries of antibody polypeptides are designed in which certain loop lengths and key residues have been chosen to ensure that the main-chain conformation of the members is known. Advantageously, these are real conformations of immunoglobulin superfamily molecules found in nature, to minimize the chances that they are non-functional, as discussed above. Germline V gene segments serve as one suitable basic framework for constructing antibody or T-cell receptor libraries; other sequences are also of use. Variations may occur at a low frequency, such that a small number of functional members may possess an altered main-chain conformation, which does not affect its function.

Canonical structure theory is also of use in the invention to assess the number of different main-chain conformations encoded by antibodies, to predict the main-chain conformation based on antibody sequences and to chose residues for diversification which do not affect the canonical structure. It is now known that, in the human $V_\kappa$ domain, the L1 loop can adopt one of four canonical structures and that the L2 loop has a single canonical structure and that 90% of human $V_\kappa$ domains adopt one of four or five canonical structures for the L3 loop (Tomlinson et al., 1995, supra); thus, in the $V_\kappa$ domain alone, different canonical structures can combine to create a range of different main-chain conformations. Given that the $V_\lambda$ domain encodes a different range of canonical structures for the L1, L2 and L3 loops and that $V_\kappa$ and $V_\lambda$ domains can pair with any $V_H$ domain which can encode several canonical structures for the Hi and H2 loops, the number of canonical structure combinations observed for these five loops is very large. This implies that the generation of diversity in the main-chain conformation may be essential for the production of a wide range of binding specificities. However, by constructing an antibody library based on a single known main-chain conformation it was found, contrary to expectation, that diversity in the main-chain conformation is not required to generate sufficient diversity to target substantially all antigens. Even more surprisingly, the single main-chain conformation need not be a consensus structure—a single naturally occurring conformation can be used as the basis for an entire library. Thus, in a preferred aspect, the invention provides a library in which the members encode a single known main-chain conformation. It is to be understood, however, that occasional variations may occur such that a small number of functional members may possess an alternative main-chain conformation, which may be unknown.

The single main-chain conformation that is chosen is preferably commonplace among molecules of the immunoglobulin superfamily type in question. A conformation is commonplace when a significant number of naturally occurring molecules are observed to adopt it. Accordingly, in a preferred aspect of the invention, the natural occurrence of the different main-chain conformations for each binding loop of an immunoglobulin superfamily molecule are considered separately and then a naturally occurring immunoglobulin superfamily molecule is chosen which possesses the desired combination of main-chain conformations for the different loops. If none is available, the nearest equivalent may be chosen. Since a disadvantage of immunoglobulin-family polypeptide libraries of the prior art is that many members have unnatural frameworks or contain framework mutations (see above), in the case of antibodies or T-cell receptors, it is preferable that the desired combination of main-chain conformations for the different loops is created by selecting germline gene segments which encode the desired main-chain conformations. It is more preferable, that the selected germline gene segments are frequently expressed and most preferable that they are the most frequently expressed.

In designing antibody libraries, therefore, the incidence of the different main-chain conformations for each of the six antigen binding loops may be considered separately. For H1, H2, L1, L2 and L3, a given conformation that is adopted by between 20% and 100% of the antigen binding loops of naturally occurring molecules is chosen. Typically, its observed incidence is above 35% (i.e., between 35% and 100%) and, ideally, above 50% or even above 65%. Since the vast majority of H3 loops do not have canonical structures, it is preferable to select a main-chain conformation which is commonplace among those loops which do display canonical structures. For each of the loops, the conformation which is observed most often in the natural repertoire is therefore selected. In human antibodies, the most popular canonical structures (CS) for each loop are as follows: H1—CS 1 (79% of the expressed repertoire), H2—CS 3 (46%), L1—CS 2 of $V_\kappa$ (39%), L2—CS 1 (100%), L3—CS 1 of $V_\kappa$ (36%) (calculation assumes a κ:λ ratio of 70:30; Hood et al., 1967, *Cold Spring Harbor Symp. Quant.* 48: 133). For H3 loops that have canonical structures, a CDR3 length (Kabat et al., 1991, supra) of seven residues with a salt-bridge from residue 94 to residue 101 appears to be the most common. There are at least 16 human antibody sequences in the EMBL data library with the required H3 length and key residues to form this conformation and at least two crystallographic structures in the protein data bank which can be used as a basis for antibody modelling (2cgr and 1tet). The most frequently expressed germline gene segments that this combination of canonical structures are the $V_H$ segment 3–23 (DP-47), the $J_H$ segment JH4b, the $V_\kappa$ segment 02/012 (DPK9) and the $J_\kappa$ segment $J_\kappa 1$. These segments can therefore be used in combination as a basis to construct a library with the desired single main-chain conformation.

Alternatively, instead of choosing the single main-chain conformation based on the natural occurrence of the different main-chain conformations for each of the binding loops in isolation, the 5 natural occurrence of combinations of main-chain conformations is used as the basis for choosing the single main-chain conformation. In the case of antibodies, for example, the natural occurrence of canonical structure combinations for any two, three, four, five or for all six of the antigen binding loops can be determined. Here, it is preferable that the chosen conformation is commonplace in naturally occurring antibodies and most preferable that it observed most frequently in the natural repertoire. Thus, in human antibodies, for example, when natural combinations of the five antigen binding loops, H1, H2, L1, L2 and L3, are considered, the most frequent combination of canonical structures is determined and then combined with the most popular conformation for the H3 loop, as a basis for choosing the single main-chain conformation.

b. Diversification of the Canonical Sequence

Having selected several known main-chain conformations or, preferably a single known main-chain conformation, the library of the invention is constructed by varying the binding site of the molecule in order to generate a repertoire with structural and/or functional diversity. This means that variants are generated such that they possess sufficient diversity in their structure and/or in their function so that they are capable of providing a range of activities. For example, where the polypeptides in question are cell-surface receptors, they may possess a diversity of target ligand binding specificities.

The desired diversity is typically generated by varying the selected molecule at one or more positions. The positions to be changed can be chosen at random or are preferably selected. The variation can then be achieved either by randomization, during which the resident amino acid is replaced by any amino acid or analogue thereof, natural or synthetic, producing a very large number of variants or by replacing the resident amino acid with one or more of a defined subset of amino acids, producing a more limited number of variants.

Various methods have been reported for introducing such diversity. Error-prone PCR (Hawkins et al., 1992, J. Mol. Biol., 226: 889), chemical mutagenesis (Deng et al., 1994, *J. Biol. Chem.,* 269: 9533) or bacterial mutator strains (Low et al., 1996, J. Mol. Biol., 260: 359) can be used to introduce random mutations into the genes that encode the molecule. Methods for mutating selected positions are also well known in the art and include the use of mismatched oligonucleotides or degenerate oligonucleotides, with or without the use of PCR. For example, several synthetic antibody libraries have been created by targeting mutations to the antigen binding loops. The H3 region of a human tetanus toxoid-binding Fab has been randomized to create a range of new binding specificities (Barbas et al., 1992, supra). Random or semi-random H3 and L3 regions have been appended to germline V gene segments to produce large libraries with unmutated framework regions (Hoogenboom and Winter, 1992, supra; Nissim et al., 1994, supra; Griffiths et al., 1994, supra; De Kruif et al., 1995, supra). Such diversification has been extended to include some or all of the other antigen binding loops (Crameri et al., 1996, Nature Med., 2: 100; Riechmann et al., 1995, *Bio/Nature Biotech Technology,* 13: 475; Morphosys, WO97/08320, supra).

Since loop randomization has the potential to create approximately more than 1015 structures for H3 alone and a similarly large number of variants for the other five loops, it is not feasible using current transformation technology or even by using cell free systems to produce a library representing all possible combinations. For example, in one of the largest libraries constructed to date, $6 \times 10^{10}$ different antibodies, which is only a fraction of the potential diversity for a library of this design, were generated (Griffiths et al., 1994, supra).

In addition to the removal of non-functional members and the use of a single known main-chain conformation, the present invention addresses these limitations by diversifying only those residues which are directly involved in creating or modifying the desired function of the molecule. For many molecules, the function will be to bind a target ligand and therefore diversity should be concentrated in the target ligand binding site, while avoiding changing residues which are crucial to the overall packing of the molecule or to maintaining the chosen main-chain conformation; therefore, the invention provides a library wherein the selected positions to be varied may be those that constitute the binding site for the target ligand.

Diversification of the Canonical Sequence as it Applies to Antibodies

In the case of an antibody library, the binding site for the target ligand is most often the antigen binding site. Thus, in a highly preferred aspect, the invention provides an antibody library in which only those residues in the antigen binding site are varied. These residues are extremely diverse in the human antibody repertoire and are known to make contacts in high-resolution antibody/antigen complexes. For example, in L2 it is known that positions 50 and 53 are diverse in naturally occurring antibodies and are observed to make contact with the antigen. In contrast, the conventional approach would have been to diversify all the residues in the corresponding Complementarity Determining Region (CDR1) as defined by Kabat et al. (1991, supra), some seven residues compared to the two diversified in the library according to the invention. This represents a significant improvement in terms of the functional diversity required to create a range of antigen binding specificities.

In nature, antibody diversity is the result of two processes: somatic recombination of germline V, D and J gene segments to create a naive primary repertoire (so called germline and junctional diversity) and somatic hypermutation of the resulting rearranged V genes. Analysis of human antibody sequences has shown that diversity in the primary repertoire is focused at the centre of the antigen binding site whereas somatic hypermutation spreads diversity to regions at the periphery of the antigen binding site that are highly conserved in the primary repertoire (see Tomlinson et al., 1996, supra). This complementarity has probably evolved as an efficient strategy for searching sequence space and, although apparently unique to antibodies, it can easily be applied to other polypeptide repertoires according to the invention. According to the invention, the residues which are varied are a subset of those that form the binding site for the target ligand. Different (including overlapping) subsets of residues in the target ligand binding site are diversified at different stages during selection, if desired.

In the case of an antibody repertoire, the two-step process of the invention is analogous to the maturation of antibodies in the human immune system. An initial 'naive' repertoire is created where some, but not all, of the residues in the antigen binding site are diversified. As used herein in this context, the term "naive" refers to antibody molecules that have no pre-determined target ligand. These molecules resemble those which are encoded by the immunoglobulin genes of an individual who has not undergone immune diversification, as is the case with fetal and newborn individuals, whose immune systems have not yet been challenged by a wide variety of antigenic stimuli. This repertoire is then selected against a range of antigens. If required, further diversity can then be introduced outside the region diversified in the initial repertoire. This matured repertoire can be selected for modified function, specificity or affinity.

The invention provides two different naive repertoires of antibodies in which some or all of the residues in the antigen binding site are varied. The "primary" library mimics the natural primary repertoire, with diversity restricted to residues at the centre of the antigen binding site that are diverse in the germline V gene segments (germline diversity) or diversified during the recombination process (junctional diversity). Those residues which are diversified include, but are not limited to, H50, H52, H52a, H53, H55, H56, H58, H95, H96, H97, H98, L50, L53, L91, L92, L93, L94 and L96. In the "somatic" library, diversity is restricted to residues that are diversified during the recombination process Ounctional diversity) or are highly somatically mutated). Those residues which are diversified include, but are not limited to: H31, H33, H35, H95, H96, H97, H98, L30, L31, L32, L34 and L96. The residues listed above as suitable for diversification in these libraries are known to make contacts in one or more antibody-antigen complexes. Since in both libraries, not all of the residues in the antigen binding site are varied, additional diversity is incorporated during selection by varying the remaining residues, if it is desired to do so. It shall be apparent to one skilled in the art that any subset of any of these residues (or additional residues which comprise the antigen binding site) can be used for the initial and/or subsequent diversification of the antigen binding site.

In the construction of libraries according to the invention, diversification of chosen positions is typically achieved at the nucleic acid level, by altering the coding sequence which specifies the sequence of the polypeptide such that a number of possible amino acids (all 20 or a subset thereof) can be incorporated at that position. Using the IUPAC nomenclature, the most versatile codon is NNK, which encodes all amino acids as well as the TAG stop codon. The NNK codon is preferably used in order to introduce the required diversity. Other codons which achieve the same ends are also of use, including the NNN codon, which leads to the production of the additional stop codons TGA and TAA.

A feature of side-chain diversity in the antigen binding site of human antibodies is a pronounced bias which favors certain amino acid residues. If the amino acid composition of the ten most diverse positions in each of the $V_H$, $V_\kappa$ and $V_\lambda$ regions are summed, more than 76% of the side-chain diversity comes from only seven different residues, these being, serine (24%), tyrosine (14%), asparagine (11%), glycine (9%), alanine (7%), aspartate (6%) and threonine (6%). This bias towards hydrophilic residues and small residues which can provide main-chain flexibility probably reflects the evolution of surfaces which are predisposed to binding a wide range of antigens and may help to explain the required promiscuity of antibodies in the primary repertoire.

Since it is preferable to mimic this distribution of amino acids, the invention provides a library wherein the distribution of amino acids at the positions to be varied mimics that seen in the antigen binding site of antibodies. Such bias in the substitution of amino acids that permits selection of certain polypeptides (not just antibody polypeptides) against a range of target ligands is easily applied to any polypeptide repertoire according to the invention. There are various methods for biasing the amino acid distribution at the position to be varied (including the use of tri-nucleotide mutagenesis, WO97/08320, Morphosys, supra), of which the preferred method, due to ease of synthesis, is the use of conventional degenerate codons. By comparing the amino acid profile encoded by all combinations of degenerate codons (with single, double, triple and quadruple degeneracy in equal ratios at each position) with the natural amino acid use it is possible to calculate the most representative codon. The codons (AGT)(AGC)T, (AGT)(AGC)C and (AGT)(AGC)(CT)—that is, DVT, DVC and DVY, respectively using IUPAC nomenclature—are those closest to the desired amino acid profile: they encode 22% serine and 11% tyrosine, asparagine, glycine, alanine, aspartate, threonine and cysteine. Preferably, therefore, libraries are constructed using either the DVT, DVC or DVY codon at each of the diversified positions.

As stated above, polypeptides which make up antibody libraries according to the invention may be whole antibodies or fragments thereof, such as Fab, F(ab')$_2$, Fv or scFv fragments, or separate $V_H$ or $V_L$ domains, any of which is either modified or unmodified. Of these, single-chain Fv fragments, or scFvs, are of particular use. ScFv fragments, as well as other antibody polypeptides, are reliably generated by antibody engineering methods well known in the art. The scFv is formed by connecting the $V_H$ and $V_L$ genes using an oligonucleotide that encodes an appropriately designed linker peptide, such as (Gly-Gly-Gly-Gly-Ser)$_3$ (SEQ ID NO: 180) or equivalent linker peptide(s). The linker bridges the C-terminal end of the first V region and N-terminal end of the second V region, ordered as either $V_H$-linker-$V_L$ or $V_L$-linker-$V_H$. In principle, the binding site of the scFv can faithfully reproduce the -specificity of the corresponding whole antibody and vice-versa.

Similar techniques for the construction of Fv, Fab and F(ab')$_2$ fragments, as well as chimeric antibody molecules are well known in the art. When expressing Fv fragments, precautions should be taken to ensure correct chain folding and association. For Fab and F(ab')$_2$ fragments, $V_H$ and $V_L$ polypeptides are combined with constant region segments, which may be isolated from rearranged genes, germline C genes or synthesized from antibody sequence data as for V region segments. A library according to the invention may be a $V_H$ or $V_L$ library. Thus, separate libraries comprising single $V_H$ and $V_L$ domains may be constructed and, optionally, include $C_H$ or $C_L$ domains, respectively, creating Dab molecules.

c. Library Vector Systems According to the Invention

Libraries according to the invention can be used for direct screening using the generic and/or target ligands or used in a selection protocol that involves a genetic display package.

Bacteriophage lambda expression systems may be screened directly as bacteriophage plaques or as colonies of lysogens, both as previously described (Huse et al., 1989, Science, 246: 1275; Caton and Koprowski, 1990, Proc. Natl. Acad. Sci. U.S.A., 87; Mullinax et al., 1990, Proc. Natl. Acad. Sci. U.S.A., 87: 8095; Persson et al., 1991, Proc. Natl. Acad. Sci. U.S.A., 88: 2432) and are of use in the invention. While such expression systems can be used to screening up to 10$^6$ different members of a library, they are not really suited to screening of larger numbers (greater than 10$^6$ members). Other screening systems rely, for example, on direct chemical synthesis of library members. One early method involves the synthesis of peptides on a set of pins or rods, such as described in WO84/03564. A similar method involving peptide synthesis on beads, which forms a peptide library in which each bead is an individual library member, is described in U.S. Pat. No. 4,631,211 and a related method is described in WO92/00091. A significant improvement of the bead-based methods involves tagging each bead with a unique identifier tag, such as an oligonucleotide, so as to facilitate identification of the amino acid sequence of each library member. These improved bead-based methods are described in WO93/06121.

Another chemical synthesis method involves the synthesis of arrays of peptides (or peptidomimetics) on a surface in a manner that places each distinct library member (e.g., unique peptide sequence) at a discrete, predefined location in the array. The identity of each library member is determined by its spatial location in the array. The locations in the array where binding interactions between a predetermined molecule (e.g., a receptor) and reactive library members occur is determined, thereby identifying the sequences of the reactive library members on the basis of spatial location. These methods are described in U.S. Pat. No. 5,143,854; WO90/15070 and WO92/10092; Fodor et al., 1991, Science, 251: 767; Dower and Fodor, 1991, Ann. Rep. Med. Chem., 26: 271.

Of particular use in the construction of libraries of the invention are selection display systems, which enable a nucleic acid to be linked to the polypeptide it expresses. As used herein, a selection display system is a system that permits the selection, by suitable display means, of the individual members of the library by binding the generic and/or target ligands.

Any selection display system may be used in conjunction with a library according to the invention. Selection protocols for isolating desired members of large libraries are known in the art, as typified by phage display techniques. Such systems, in which diverse peptide sequences are displayed on the surface of filamentous bacteriophage (Scott and Smith, 1990, supra), have proven useful for creating libraries of antibody fragments (and the nucleotide sequences that encoding them) for the in vitro selection and amplification of specific antibody fragments that bind a target antigen. The nucleotide sequences encoding the $V_H$ and $V_L$ regions are linked to gene fragments which encode leader signals that direct them to the periplasmic space of E. coli and as a result the resultant antibody fragments are displayed on the surface of the bacteriophage, typically as fusions to bacteriophage coat proteins (e.g., pIII or pVIII). Alternatively, antibody fragments are displayed externally on lambda phage capsids (phage bodies). An advantage of phage-based display systems is that, because they are biological systems, selected library members can be amplified simply by growing the phage containing the selected library member in bacterial cells. Furthermore, since the nucleotide sequence that encode the polypeptide library member is contained on a phage or phagemid vector, sequencing, expression and subsequent genetic manipulation is relatively straightforward.

Methods for the construction of bacteriophage antibody display libraries and lambda phage expression libraries are well known in the art (McCafferty et al., 1990, supra; Kang et al., 1991, Proc. Natl. Acad. Sci. U.S.A., 88: 4363; Clackson et al., 1991, Nature, 352: 624; Lowman et al., 1991, Biochemistry, 30: 10832; Burton et al., 1991, Proc. Natl. Acad. ci U.S.A., 88: 10134; Hoogenboom et al., 1991 Nucleic Acids Res., 19: 4133; Chang et al., 1991, J. Immunol., 147: 3610; Breitling et al., 1991, Gene, 104: 147; Marks et al., 1991, supra; Barbas et al., 1992, supra; Hawkins and Winter, 1992, J. Immunol., 22: 867; Marks et al., 1992, J. Biol. Chem., 267: 16007; Lerner et al., 1992, Science, 258: 1313, incorporated herein by reference).

One particularly advantageous approach has been the use of scFv phage-libraries (Huston et al., 1988, Proc. Natl. Acad. Sci U.S.A., 85: 5879–5883; Chaudhary et al., 1990, Proc. Natl. Acad. Sci. U.S.A., 87: 1066–1070; McCafferty et al., 1990, supra; Clackson et al., 1991, supra; Marks et al., 1991, supra; Chiswell et al., 1992, Trends Biotech., 10: 80; Marks et al., 1992, supra). Various embodiments of scFv libraries displayed on bacteriophage coat proteins have been described. Refinements of phage display approaches are also known, for example as described in WO96/06213 and WO92/01047 (Medical Research Council et al.) and WO97/08320 (Morphosys, supra), which are incorporated herein by reference.

Other systems for generating libraries of polypeptides or nucleotides involve the use of cell-free enzymatic machinery for the in vitro synthesis of the library members. In one method, RNA molecules are selected by alternate rounds of selection against a target ligand and PCR amplification (Tuerk and Gold, 1990, *Science,* 249: 505; Ellington and Szostak, 1990, *Nature,* 346: 818). A similar technique may be used to identify DNA sequences which bind a predetermined human transcription factor (Thiesen and Bach, 1990, *Nucleic Acids Res.,* 18: 3203; Beaudry and Joyce, 1992, *Science,* 257: 635; WO92/05258 and WO92/14843). In a similar way, in vitro translation can be used to synthesize polypeptides as a method for generating large libraries. These methods which generally comprise stabilized polysome complexes, are described further in WO88/08453, WO90/05785, WO90/07003, WO91/02076, WO91/05058, and WO92/02536. Alternative display systems which are not phage-based, such as those disclosed in WO95/22625 and WO95/11922 (Affymax) use the polysomes to display polypeptides for selection. These and all the foregoing documents also are incorporated herein by reference.

The invention accordingly provides a method for selecting a polypeptide having a desired generic and/or target ligand binding site from a repertoire of polypeptides, comprising the steps of:

a) expressing a library according to the preceding aspects of the invention;

b) contacting the polypeptides with the generic and/or target ligand and selecting those which bind the generic and/or target ligand; and c) optionally amplifying the selected polypeptide(s) which bind the generic and/or target ligand.

d) optionally repeating steps a)-c).

Preferably, steps a)-d) are performed using a phage display system.

Since the invention provides a library of polypeptides which have binding sites for both generic and target ligands the above selection method can be applied to a selection using either the generic ligand or the target ligand. Thus, the initial library can be selected using the generic ligand and then the target ligand or using the target ligand and then the generic ligand. The invention also provides for multiple selections using different generic ligands either in parallel or in series before or after selection with the target ligand.

Preferably, the method according to the invention further comprises the steps of subjecting the selected polypeptide(s) to additional variation (as described herein) and repeating steps a) to d).

Since the generic ligand, by its very nature, is able to bind all library members selected using the generic ligand, the method according to the invention further comprises the use of the generic ligand (or some conjugate thereof) to detect, immobilize, purify or immunoprecipitate any functional member or population of members from the library (whether selected by binding the target ligand or not).

Since the invention provides a library in which the members have a known main-chain conformation the method according to the invention further comprises the production of a three-dimensional structural model of any functional member of the library (whether selected by binding the target ligand or not). Preferably, the building of such a model involves homology modeling and/or molecular replacement. A preliminary model of the main-chain conformation can be created by comparison of the polypeptide sequence to the sequence of a known three-dimensional structure, by secondary structure prediction or by screening structural libraries. Computational software may also be used to predict the secondary structure of the polypeptide. In order to predict the conformations of the side-chains at the varied positions, a side-chain rotamer library may be employed.

In general, the nucleic acid molecules and vector constructs required for the performance of the present invention are available in the art and may be constructed and manipulated as set forth in standard laboratory manuals, such as Sambrook et al., 1989, *Molecular Cloning: A Laboratory Manual,* Cold Spring Harbor, USA.

The manipulation of nucleic acids in the present invention is typically carried out in recombinant vectors. As used herein, vector refers to a discrete element that is used to introduce heterologous DNA into cells for the expression and/or replication thereof. Methods by which to select or construct and, subsequently, use such vectors are well known to one of moderate skill in the art. Numerous vectors are publicly available, including bacterial plasmids, bacteriophage, artificial chromosomes and episomal vectors. Such vectors may be used for simple cloning and mutagenesis; alternatively, as is typical of vectors in which repertoire (or pre-repertoire) members of the invention are carried, a gene expression vector is employed. A vector of use according to the invention may be selected to accommodate a polypeptide coding sequence of a desired size, typically from 0.25 kilobase (kb) to 40 kb in length. A suitable host cell is transformed with the vector after in vitro cloning manipulations. Each vector contains various functional components, which generally include a cloning (or "polylinker") site, an origin of replication and at least one selectable marker gene. If given vector is an expression vector, it additionally possesses one or more of the following: enhancer element, promoter, transcription termination and signal sequences, each positioned in the vicinity of the cloning site, such that they are operatively linked to the gene encoding a polypeptide repertoire member according to the invention.

Both cloning and expression vectors generally contain nucleic acid sequences that enable the vector to replicate in one or more selected host cells. Typically in cloning vectors, this sequence is one that enables the vector to replicate independently of the host chromosomal DNA and includes origins of replication or autonomously replicating sequences. Such sequences are well known for a variety of bacteria, yeast and viruses. The origin of replication from the plasmid pBR322 is suitable for most Gram-negative bacteria, the 2 micron plasmid origin is suitable for yeast, and various viral origins (e.g. SV40, adenovirus) are useful for cloning vectors in mammalian cells. Generally, the origin of replication is not needed for mammalian expression vectors unless these are used in mammalian cells able to replicate high levels of DNA, such as COS cells.

Advantageously, a cloning or expression vector may contain a selection gene also referred to as selectable marker. This gene encodes a protein necessary for the survival or growth of transformed host cells grown in a selective culture medium. Host cells not transformed with the vector containing the selection gene will therefore not survive in the culture medium. Typical selection genes encode proteins that confer resistance to antibiotics and other toxins, e.g., ampicillin, neomycin, methotrexate or tetracycline, complement auxotrophic deficiencies, or supply critical nutrients not available in the growth media.

Since the replication of vectors according to the present invention is most conveniently performed in *E. coli,* an *E. coli*-selectable marker, for example, the β-lactamase gene that confers resistance to the antibiotic ampicillin, is of use. These can be obtained from *E. coli* plasmids, such as pBR322 or a pUC plasmid such as pUC 18 or pUC 19.

Expression vectors usually contain a promoter that is recognized by the host organism and is operably linked to the coding sequence of interest. Such a promoter may be inducible or constitutive. The term "operably linked" refers to ajuxtaposition wherein the components described are in a relationship permitting them to function in their intended manner. A control sequence "operably linked" to a coding sequence is ligated in such a way that expression of the coding sequence is achieved under conditions compatible with the control sequences.

Promoters suitable for use with prokaryotic hosts include, for example, the β-lactamase and lactose promoter systems, alkaline phosphatase, the tryptophan (trp) promoter system and hybrid promoters such as the tac promoter. Promoters for use in bacterial systems will also generally contain a Shine-Dalgarno sequence operably linked to the coding sequence.

In the library according to the present invention, the preferred vectors are expression vectors that enables the expression of a nucleotide sequence corresponding to a polypeptide library member. Thus, selection with the generic and/or target ligands can be performed by separate propagation and expression of a single clone expressing the polypeptide library member or by use of any selection display system. As described above, the preferred selection display system is bacteriophage display. Thus, phage or phagemid vectors may be used. The preferred vectors are phagemid vectors which have an $E.$ $coli.$ origin of replication (for double stranded replication) and also a phage origin of replication (for production of single-stranded DNA). The manipulation and expression of such vectors is well known in the art (Hoogenboom and Winter, 1992, supra; Nissim et al., 1994, supra). Briefly, the vector contains a β-lactamase gene to confer selectivity on the phagemid and a lac promoter upstream of a expression cassette that consists (N to C terminal) of a pelB leader sequence (which directs the expressed polypeptide to the periplasmic space), a multiple cloning site (for cloning the nucleotide version of the library member), optionally, one or more peptide tag (for detection), optionally, one or more TAG stop codon and the phage protein pIII. Thus, using various suppressor and non-suppressor strains of $E.$ $coli$ and with the addition of glucose, iso-propyl thio-β-D-galactoside (IPTG) or a helper phage, such as VCS M13, the vector is able to replicate as a plasmid with no expression, produce large quantities of the polypeptide library member only or produce phage, some of which contain at least one copy of the polypeptide-pIII fusion on their surface.

Construction of vectors according to the invention employs conventional ligation techniques. Isolated vectors or DNA fragments are cleaved, tailored, and religated in the form desired to generate the required vector. If desired, analysis to confirm that the correct sequences are present in the constructed vector can be performed in a known fashion. Suitable methods for constructing expression vectors, preparing in vitro transcripts, introducing DNA into host cells, and performing analyses for assessing expression and function are known to those skilled in the art. The presence of a gene sequence in a sample is detected, or its amplification and/or expression quantified by conventional methods, such as Southern or Northern analysis, Western blotting, dot blotting of DNA, RNA or protein, in situ hybridization, immunocytochemistry or sequence analysis of nucleic acid or protein molecules. Those skilled in the art will readily envisage how these methods may be modified, if desired.

Mutagenesis Using the Polymerase Chain Reaction (PCR)

Once a vector system is chosen and one or more nucleic acid sequences encoding polypeptides of interest are cloned into the library vector, one may generate diversity within the cloned molecules by undertaking mutagenesis prior to expression; alternatively, the encoded proteins may be expressed and selected, as described above, before mutagenesis and additional rounds of selection are performed. As stated above, mutagenesis of nucleic acid sequences encoding structurally optimized polypeptides, is carried out by standard molecular methods. Of particular use is the polymerase chain reaction, or PCR, (Mullis and Faloona, 1987, *Methods Enzymol.*, 155: 335, herein incorporated by reference). PCR, which uses multiple cycles of DNA replication catalyzed by a thermostable, DNA-dependent DNA polymerase to amplify the target sequence of interest, is well known in the art.

Oligonucleotide primers useful according to the invention are single-stranded DNA or RNA molecules that hybridize to a nucleic acid template to prime enzymatic synthesis of a second nucleic acid strand. The primer is complementary to a portion of a target molecule present in a pool of nucleic acid molecules used in the preparation of sets of arrays of the invention. It is contemplated that such a molecule is prepared by synthetic methods, either chemical or enzymatic. Alternatively, such a molecule or a fragment thereof is naturally occurring, and is isolated from its natural source or purchased from a commercial supplier. Mutagenic oligonucleotide primers are 15 to 100 nucleotides in length, ideally from 20 to 40 nucleotides, although oligonucleotides of different length are of use.

Typically, selective hybridization occurs when two nucleic acid sequences are substantially complementary (at least about 65% complementary over a stretch of at least 14 to 25 nucleotides, preferably at least about 75%, more preferably at least about 90% complementary). See Kanehisa, 1984, *Nucleic Acids Res.*, 12: 203, incorporated herein by reference. As a result, it is expected that a certain degree of mismatch at the priming site is tolerated. Such mismatch may be small, such as a mono-, di- or trinucleotide. Alternatively, it may comprise nucleotide loops, which we define as regions in which mismatch encompasses an uninterrupted series of four or more nucleotides.

Overall, five factors influence the efficiency and selectivity of hybridization of the primer to a second nucleic acid molecule. These factors, which are (i) primer length, (ii) the nucleotide sequence and/or composition, (iii) hybridization temperature, (iv) buffer chemistry and (v) the potential for steric hindrance in the region to which the primer is required to hybridize, are important considerations when non-random priming sequences are designed.

There is a positive correlation between primer length and both the efficiency and accuracy with which a primer will anneal to a target sequence; longer sequences have a higher melting temperature (TM) than do shorter ones, and are less likely to be repeated within a given target sequence, thereby minimizing promiscuous hybridization. Primer sequences with a high G–C content or that comprise palindromic sequences tend to self-hybridize, as do their intended target sites, since unimolecular, rather than bimolecular, hybridization kinetics are generally favored in solution; at the same time, it is important to design a primer containing sufficient numbers of G–C nucleotide pairings to bind the target sequence tightly, since each such pair is bound by three hydrogen bonds, rather than the two that are found when A and T bases pair. Hybridization temperature varies inversely with primer annealing efficiency, as does the concentration of organic solvents, e.g. formamide, that might be included in a hybridization mixture, while increases in salt concentration facilitate binding. Under stringent hybridization conditions, longer probes hybridize more efficiently than do shorter ones, which are sufficient under more permissive conditions. Stringent hybridization conditions typically include salt concentrations of less than about IM, more usually less than about 500 mM and preferably less than about 200 mM. Hybridization temperatures range from as low as 0° C. to greater than 22° C., greater than about 30° C., and (most often) in excess of about 37° C. Longer fragments may require higher hybridization temperatures for specific hybridization. As several factors affect the stringency of hybridization, the combination of parameters is more important than the absolute measure of any one alone.

Primers are designed with these considerations in mind. While estimates of the relative merits of numerous sequences may be made mentally by one of skill in the art, computer programs have been designed to assist in the evaluation of these several parameters and the optimization of primer sequences. Examples of such programs are "PrimerSelect" of the DNASTAR™ software package (DNAStar, Inc.; Madison, Wis.) and OLIGO 4.0 (National Biosciences, Inc.). Once designed, suitable oligonucleotides are prepared by a suitable method, e.g., the phosphoramidite method described by Beaucage and Caruthers, 1981, Tetrahedron Lett. 22: 1859) or the method according to Matteucci and Caruthers, 1981, J. Am. Chem. Soc., 103: 3185, both incorporated herein by reference, or by other chemical methods using either a commercial automated oligonucleotide synthesizer or VLSLIPS™ technology.

PCR is performed using template DNA (at least 1 fg; more usefully, 1–1000 ng) and at least 25 pmol of oligonucleotide primers; it may be advantageous to use a larger amount of primer when the primer pool is heavily heterogeneous, as each sequence is represented by only a small fraction of the molecules of the pool, and amounts become limiting in the later amplification cycles. A typical reaction mixture includes: 2 µl of DNA, 25 pmol of oligonucleotide primer, 2.5 µl of 10× PCR buffer 1 (Perkin-Elmer, Foster City, Calif.), 0.4 µl of 1.25 µM dNTP, 0.15 µl (or 2.5 units) of Taq DNA polymerase (Perkin Elmer, Foster City, Calif.) and deionized water to a total volume of 25 µl. Mineral oil is overlaid and the PCR is performed using a programmable thermal cycler.

The length and temperature of each step of a PCR cycle, as well as the number of cycles, is adjusted in accordance to the stringency requirements in effect. Annealing temperature and timing are determined both by the efficiency with which a primer is expected to anneal to a template and the degree of mismatch that is to be tolerated; obviously, when nucleic acid molecules are simultaneously amplified and mutagenized, mismatch is required, at least in the first round of synthesis. In attempting to amplify a population of molecules using a mixed pool of mutagenic primers, the loss, under stringent (high-temperature) annealing conditions, of potential mutant products that would only result from low melting temperatures is weighed against the promiscuous annealing of primers to sequences other than the target site. The ability to optimize the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20–40 cycles consisting of denaturation (94–99° C. for 15 seconds to 1 minute), annealing (temperature determined as discussed above; 1–2 minutes), and extension (72° C. for 1–5 minutes, depending on the length of the amplified product). Final extension is generally for 4 minutes at 72° C., and may be followed by an indefinite (0–24 hour) step at 4° C.

Structural Analysis of Repertoire Members

Since the invention provides a repertoire of polypeptides of known main-chain conformation, a three-dimensional structural model of any member of the repertoire is easily generated. Typically, the building of such a model involves homology modeling and/or molecular replacement. A preliminary model of the main-chain conformation is created by comparison of the polypeptide sequence to a similar sequence of known three-dimensional structure, by secondary structure prediction or by screening structural libraries. Molecular modeling computer software packages are commercially available, and are useful in predicting polypeptide secondary structures. In order to predict the conformations of the side-chains at the varied positions, a side-chain rotamer library may be employed.

Antibodies for Use as Ligands in Polypeptide Selection

A generic or target ligand to be used in the polypeptide selection according to the present invention may, itself, be an antibody. This is particularly true of generic ligands, which bind to structural features that are substantially conserved in functional polypeptides to be selected for inclusion in repertoires of the invention. If an appropriate antibody is not publicly available, it may be produced by phage display methodology (see above) or as follows:

Either recombinant proteins or those derived from natural sources can be used to generate antibodies using standard techniques, well known to those in the field. For example, the protein (or "immunogen") is administered to challenge a mammal such as a monkey, goat, rabbit or mouse. The resulting antibodies can be collected as polyclonal sera, or antibody-producing cells from the challenged animal can be immortalized (e.g., by fusion with an immortalizing fusion partner to produce a hybridoma), which cells then produce monoclonal antibodies.

a. Polyclonal Antibodies

The antigen protein is either used alone or conjugated to a conventional carrier in order to increases its immunogenicity, and an antiserum to the peptide-carrier conjugate is raised in an animal, as described above. Coupling of a peptide to a carrier protein and immunizations may be performed as described (Dymecki et al., 1992, J. Biol. Chem., 267: 4815). The serum is titered against protein antigen by ELISA or alternatively by dot or spot blotting (Boersma and Van Leeuwen, 1994, J. Neurosci. Methods, 51: 317). The serum is shown to react strongly with the appropriate peptides by ELISA, for example, following the procedures of Green et al., 1982, Cell, 28: 477.

b. Monoclonal Antibodies

Techniques for preparing monoclonal antibodies are well known, and monoclonal antibodies may be prepared using any candidate antigen, preferably bound to a carrier, as described by Amheiter et al., 1981, Nature, 294: 278. Monoclonal antibodies are typically obtained from hybridoma tissue cultures or from ascites fluid obtained from animals into which the hybridoma tissue was introduced. Nevertheless, monoclonal antibodies may be described as being "raised against" or "induced by" a protein.

After being raised, monoclonal antibodies are tested for function and specificity by any of a number of means. Similar procedures can also be used to test recombinant antibodies produced by phage display or other in vitro selection technologies. Monoclonal antibody-producing hybridomas (or polyclonal sera) can be screened for antibody binding to the immunogen, as well. Particularly preferred immunological tests include enzyme-linked immunoassays (ELISA), immunoblotting and immunoprecipitation (see Voller, 1978, Diagnostic Horizons, 2: 1, Microbiological Associates Quarterly Publication, Walkersville, Md.; Voller et al., 1978, *J. Clin. Pathol.*, 31: 507; U.S. Reissue Pat. No. 31,006; UK Patent 2,019,408; Butler, 1981, *Methods Enzymol.*, 73: 482; Maggio, E. (ed.), 1980, *Enzyme Immunoassay*, CRC Press, Boca Raton, Fla.) or radioimmunoassays (RIA) (Weintraub, B., *Principles of radioimmunoassays, Seventh Training Course on Radioligand Assay Techniques*, The Endocrine Society, March 1986, pp. 1–5, 46–49 and 68–78), all to detect binding of the antibody to the immunogen against which it was raised. It will be apparent to one skilled in the art that either the antibody molecule or the immunogen must be labeled to facilitate such detection. Techniques for labeling antibody molecules are well known to those skilled in the art (see Harlour and Lane, 1989, *Antibodies*, Cold Spring Harbor Laboratory, pp. 1–726).

Alternatively, other techniques can be used to detect binding to the immunogen, thereby confirming the integrity of the antibody which is to serve either as a generic antigen or a target antigen according to the invention. These include chromatographic methods such as SDS PAGE, isoelectric focusing, Western blotting, HPLC and capillary electrophoresis.

"Antibodies" are defined herein as constructions using the binding (variable) region of such antibodies, and other antibody modifications. Thus, an antibody useful in the invention may comprise whole antibodies, antibody fragments, polyfunctional antibody aggregates, or in general any substance comprising one or more specific binding sites from an antibody. The antibody fragments may be fragments such as Fv, Fab and F(ab')$_2$ fragments or any derivatives thereof, such as a single chain Fv fragments. The antibodies or antibody fragments may be non-recombinant, recombinant or humanized. The antibody may be of any immunoglobulin isotype, e.g., IgG, IgM, and so forth. In addition, aggregates, polymers, derivatives and conjugates of immunoglobulins or their fragments can be used where appropriate.

Metallic Ions as Ligands for the Selection of Polypeptides

As stated above, ligands other than antibodies are of use in the selection of polypeptides according to the invention. One such category of ligand is that of metallic ions. Immobilized metal affinity chromatography (IMAC; Hubert and Porath, 1980, *J. Chromatography*, 98: 247–255) takes advantage of the metal-binding properties of histidine and cysteine amino acid residues, as well as others that may bind metals, on the exposed surfaces of numerous proteins. It employs a resin, typically agarose, comprising a bidentate metal chelator (e.g. iminodiacetic acid, IDA, a dicarboxylic acid group) to which is complexed metallic ions; in order to generate a metallic-ion-bearing resin according to the invention, agarose/IDA is mixed with a metal salt (for example, $CuCl_2.2H_2O$), from which the IDA chelates the divalent cations. One commercially-available agarose/IDA preparation is "CHELATING SEPHAROSE 6B" (Pharmacia Fine Chemicals; Piscataway, N.J.). Metallic ion that are of use include, but are not limited to, the divalent cations $Ni^{2+}$, $Cu^{2+}$, $Zn^{2+}$ and $Co^{2+}$. A pool of polypeptide molecules is prepared in a binding buffer which consists essentially of salt (typically, NaCl or KCl) at a 0.1- to 1.0M concentration and a weak ligand (such as Tris or ammonia), the latter of which has affinity for the metallic ions of the resin, but to a lesser degree than does a polypeptide to be selected according to the invention. Useful concentrations of the weak ligand range from 0.01- to 0.1M in the binding buffer.

The polypeptide pool is contacted with the resin under conditions which permit polypeptides having metal-binding domains (see below) to bind; after impurities are washed away, the selected polypeptides are eluted with a buffer in which the weak ligand is present in a higher concentration than in the binding buffer, specifically, at a concentration sufficient for the weak ligand to displace the selected polypeptides, despite its lower binding affinity for the metallic ions. Useful concentrations of the weak ligand in the elution buffer are 10- to 50-fold higher than in the binding buffer, typically from 0.1 to 0.3 M; note that the concentration of salt in the elution buffer equals that in the binding buffer. According to the methods of the present invention, the metallic ions of the resin typically serve as the generic ligand; however, it is contemplated that they may also be used as the target ligand.

IMAC is carried out using a standard chromatography apparatus (columns, through which buffer is drawn by gravity, pulled by a vacuum or driven by pressure); alternatively, a large-batch procedure is employed, in which the metal-bearing resin is mixed, in slurry form, with the polypeptide pool from which members of a repertoire of the invention are to be selected.

Partial purification of a serum T4 protein by IMAC has been described (Staples et al., U.S. Pat. No. 5,169,936); however, the broad spectrum of proteins comprising surface-exposed metal-binding domains also encompasses other soluble T4 proteins, human serum proteins (e.g. IgG, haptoglobin, hemopexin, Gc-globulin, C1q, C3, C4), human desmoplasmin, *Dolichos biflorus* lectin, zinc-inhibited Tyr (P) phosphatases, phenolase, carboxypeptidase isoenzymes, Cu,Zn superoxide dismutases (including those of humans and all other eukaryotes), nucleoside diphosphatase, leukocyte interferon, lactoferrin, human plasma $\alpha_2$-SH glycoprotein, $_2\alpha$-macroglobulin, $_1\alpha$-antitrypsin, plasminogen activator, gastrointestinal polypeptides, pepsin, human and bovine serum albumin, granule proteins from granulocytes, lysozymes, non-histone proteins, human fibrinogen, human serum transferrin, human lymphotoxin, calmodulin, protein A, avidin, myoglobins, somatomedins, human growth hormone, transforming growth factors, platelet-derived growth factor, $\alpha$-human atrial natriuretic polypeptide, cardiodilatin and others. In addition, extracellular domain sequences of membrane-bound proteins may be purified using IMAC. Note that repertoires comprising any of the above proteins or metal-binding variants thereof may be produced according to the methods of the invention.

Following elution, selected polypeptides are removed from the metal binding buffer and placed in a buffer appropriate to their next use. If the metallic ion has been used to generate a first selected polypeptide pool according to the invention, the moleucles of that pool are placed into a buffer that is optimized for binding with the second ligand to be used in selection of the members of the functional polypeptide repertoire. If the metal is, instead, used in the second selection step, the polypeptides of the repertoire are transferred to a buffer suitable either to storage (e.g. a 0.5% glycine buffer) or the use for which they are intended. Such buffers include, but are not limited to: water, organic solvents, mixtures of water and water-miscible organic solvents, physiological salt buffers and protein/nucleic acid or protein/protein binding buffers. Alternatively, the polypeptide molecules may be dehydrated (i.e. by lyophilization) or immobilized on a solid or semi-solid support, such as a nitrocellulose or nylon filtration membrane or a gel matrix (i.e. of agarose or polyacrylamide) or crosslinked to a chromatography resin.

Polypeptide molecules may be removed from the elution buffer by any of a number of methods known in the art. The polypeptide eluate may be dialyzed against water or another solution of choice; if the polypeptides are to be lyophilized, water to which has been added protease inhibitors (e.g. pepstatin, aprotinin, leupeptin, or others) is used. Alternatively, the sample may be subjected to ammonium sulfate precipitation, which is well known in the art, prior to resuspension in the medium of choice.

Use of Polypeptides Selected According to the Invention

As alluded to above, the molecules selected according to the invention are of use in diagnostic, prophylactic and therapeutic procedures. For example, enzyme variants generated and selected by these methods may be assayed for activity, either in vitro or in vivo using techniques well known in the art, by which they are incubated with candidate substrate molecules and the conversion of substrate to product is analyzed. Selected cell-surface receptors or adhesion molecules might be expressed in cultured cells which are then tested for their ability to respond to biochemical stimuli or for their affinity with other cell types that express cell-surface molecules to which the undiversified adhesion molecule would be expected to bind, respectively.

Antibody polypeptides selected according to the invention are of use diagnostically in Western analysis and in situ protein detection by standard immunohistochemical procedures; for use in these applications, the antibodies of a selected repertoire may be labeled in accordance with techniques known to the art. In addition, such antibody polypeptides may be used preparatively in affinity chromatography procedures, when complexed to a chromatographic support, such as a resin. All such techniques are well known to one of skill in the art.

Therapeutic and prophylactic uses of proteins prepared according to the invention involve the administration of polypeptides selected according to the invention to a recipient mammal, such as a human. Of particular use in this regard are antibodies, receptors (including, but not limited to, T-cell receptors) and, in the case in which an antibody or receptor was used as either a generic or target ligand, proteins which bind to them.

Substantially pure antibodies or binding proteins thereof of at least 90 to 95% homogeneity are preferred for administration to a mammal, and 98 to 99% or more homogeneity is most preferred for pharmaceutical uses, especially when the mammal is a human. Once purified, partially or to homogeneity as desired, the selected polypeptides may be used diagnostically or therapeutically (including extracorporeally) or in developing and performing assay procedures, immunofluorescent stainings and the like (Lefkovite and Pernis, (1979 and 1981) *Immunological Methods*, Volumes I and II, Academic Press, NY).

The selected antibodies or binding proteins thereof of the present invention will typically find use in preventing, suppressing or treating inflammatory states, allergic hypersensitivity, cancer, bacterial or viral infection, and autoimmune disorders (which include, but are not limited to, Type I diabetes, multiple sclerosis, rheumatoid arthritis, systemic lupus erythematosus, Crohn's disease and myasthenia gravis).

In the instant application, the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the antibodies or binding proteins thereof in protecting against or treating the disease are available. Methods for the testing of systemic lupus erythematosus (SLE) in susceptible mice are known in the art (Knight et al., 1978, 1. Exp. Med., 147: 1653; Reinersten et al., 1978, *New Eng. J. Med.*, 299: 515). Myasthenia Gravis (MG) is tested in SJL/J female mice by inducing the disease with soluble AchR protein from another species (Lindstrom et al., 1988, *Adv. Immunol.*, 42: 233–284). Arthritis is induced in a susceptible strain of mice by injection of Type II collagen (Stuart et al., 1984, *Ann. Rev. Immunol.*, 42: 233–284). A model by which adjuvant arthritis is induced in susceptible rats by injection of mycobacterial heat shock protein has been described (Van Eden et al., 1988, *Nature*, 331: 171–173). Thyroiditis is induced in mice by administration of thyroglobulin as described (Maron et al., 1980, *J. Fxp. Med.*, 152: 1115–1120). Insulin dependent diabetes mellitus (IDDM) occurs naturally or can be induced in certain strains of mice such as those described by Kanasawa et al. (1984, *Diabetologia*, 27: 113). EAE in mouse and rat serves as a model for MS in human. In this model, the demyelinating disease is induced by administration of myelin basic protein (see Paterson, 1986, *Textbook of Immunopathology*, Mischer et al., eds., Grune and Stratton, N.Y., pp. 179–213; McFarlin et al., 1973, *Science*, 179: 478–480: and Satoh et al., 1987, *J. Immunol.*, 138: 179–184).

The selected antibodies, receptors (including, but not limited to T-cell receptors) or binding proteins thereof of the present invention may also be used in combination with other antibodies, particularly monoclonal antibodies (MAbs) reactive with other markers on human cells responsible for the diseases. For example, suitable T-cell markers can include those grouped into the so-called "Clusters of Differentiation," as named by the First International Leukocyte Differentiation Workshop (Bernhard et al., 1984, *Leukocyte Typing*, Springer Verlag, N.Y.).

Generally, the present selected antibodies, receptors or binding proteins will be utilized in purified form together with pharmacologically appropriate carriers. Typically, these carriers include aqueous or alcoholic/aqueous solutions, emulsions or suspensions, any including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack, 1982, *Remington's Pharmaceutical Sciences*, 16th Edition).

The selected polypeptides of the present invention may be used as separately administered compositions or in conjunction with other agents. These can include various immunotherapeutic drugs, such as cylcosporine, methotrexate, adriamycin or cisplatinum, and immunotoxins. Pharmaceutical compositions can include "cocktails" of various cytotoxic or other agents in conjunction with the selected antibodies, receptors or binding proteins thereof of the present invention, or even combinations of selected polypeptides according to the present invention having different specificities, such as polypeptides selected using different target ligands, whether or not they are pooled prior to administration.

The route of administration of pharmaceutical compositions according to the invention may be any of those commonly known to those of ordinary skill in the art. For therapy, including without limitation immunotherapy, the selected antibodies, receptors or binding proteins thereof of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. The dosage and frequency of administration will depend on the age, sex and condition of the patient, concurrent administration of other drugs, counterindications and other parameters to be taken into account by the clinician.

The selected polypeptides of this invention can be lyophilized for storage and reconstituted in a suitable carrier prior to use. This technique has been shown to be effective with conventional immunoglobulins and art-known lyophilization and reconstitution techniques can be employed. It will be appreciated by those skilled in the art that lyophilization and reconstitution can lead to varying degrees of antibody activity loss (e.g. with conventional immunoglobulins, IgM antibodies tend to have greater activity loss than IgG antibodies) and that use levels may have to be adjusted upward to compensate.

The compositions containing the present selected polypeptides or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected antibody, receptor (e.g. a T-cell receptor) or binding protein thereof per kilogram of body weight, with doses of 0.05 to 2.0 mg/kg/dose being more commonly used. For prophylactic applications, compositions containing the present selected polypeptides or cocktails thereof may also be administered in similar or slightly lower dosages.

A composition containing a selected polypeptide according to the present invention may be utilized in prophylactic and therapeutic settings to aid in the alteration, inactivation, killing or removal of a select target cell population in a mammal. In addition, the selected repertoires of polypeptides described herein may be used extracorporeally or in vitro selectively to kill, deplete or otherwise effectively remove a target cell population from a heterogenous collection of cells. Blood from a mammal may be combined extracorporeally with the selected antibodies, cell-surface receptors or binding proteins thereof whereby the undesired cells are killed or otherwise removed from the blood for return to the mammal in accordance with standard techniques.

Selection of repertoires of polypeptides according to the methods described above is presented in the following non-limiting examples.

EXAMPLE 1

Antibody Library Design

A. Main-chain Conformation

For five of the six antigen binding loops of human antibodies (L1, L2, L3, H1 and H2) there are a limited number of main-chain conformations, or canonical structures (Chothia, 1992, supra; Tomlinson et al., 1995b, supra; Williams et al., 1996, supra). The most popular main-chain conformation for each of these loops is used to provide a single known main-chain conformation according to the invention. These are: H1—CS 1 (79% of the expressed repertoire), H2—CS 3 (46%), L1—CS 2 of V, (39%), L2—CS 1 (100%), L3—CS 1 of $V_\kappa$ (36%). The H3 loop forms a limited number of main-chain conformations for short loop lengths (Martin et al., 1996, *J. Mol. Biol.,* 263: 800; Shirai et al., 1996, *FEBS Letters,* 399: 1). Thus, where the H3 has a CDR3 length (as defined by Kabat et al., 1991, supra) of seven residues and has a lysine or arginine residue at position H94 and an aspartate residue at position H101 a salt-bridge is formed between these two residues and in most cases a single main-chain conformation is likely to be produced. There are at least 16 human antibody sequences in the EMBL data library with the required H3 length and key residues to form this conformation and at least two crystallographic structures in the protein data bank which can be used as a basis for antibody modeling (2cgr and 1tet).

In this case, the most frequently expressed germline gene segments which encode the desired loop lengths and key residues to produce the required combinations of canonical structures are the $V_H$ segment 3–23 (DP-47), the $J_H$ segment JH4b, the $V_\kappa$ segment O2/O12 (DPK9) and the $J_\kappa$ segment $J_\kappa 1$. These segments can therefore be used in combination as a basis to construct a library with the desired single main-chain conformation. The $V_\kappa$ segment O2/O12 (DPK9) is member of the $V_\kappa 1$ family and therefore will bind the superantigen Protein L. The $V_H$ segment 3–23 (DP-47) is a member of the $V_H 3$ family and therefore should bind the superantigen Protein A, which can then be used as a generic ligand.

B. Selection of Positions for Variation

Analysis of human $V_H$ and $V_\kappa$ sequences indicates that the most diverse positions in the mature repertoire are those that make the most contacts with antigens (see Tomlinson et al., 1996, *J. Mol. Biol.,* 256: 813; FIG. 1). These positions form the functional antigen binding site and are therefore selected for side-chain diversification (FIG. 2). H54 is a key residue and points away from the antigen binding site in the chosen H2 canonical structure 3 (the diversity seen at this position is due to canonical structures 1, 2 and 4 where H54 points into the binding site). In this case H55 (which points into the binding site) is diversified instead. The diversity at these positions is created either by germline or junctional diversity in the primary repertoire or by somatic hypermutation (Tomlinson et al., 1996, supra; FIG. 1). Two different subsets of residues in the antigen binding site were therefore varied to create two different library formats. In the "primary" library the residues selected for variation are from H2, H3, L2 and L3 (diversity in these loops is mainly the result of germline or junctional diversity). The positions varied in this library are: H50, H52, H52a, H53, H55, H56, H58, H95, H96, H97, H98, L50, L53, L91, L92, L93, L94 and L96 (18 residues in total, FIG. 2). In the "somatic" library the residues selected for variation are from H1, H3, L1 and the end of L3 (diversity here is mainly the result of somatic hypermutation or junctional diversity). The positions varied in this library are: H31, H33, H35, H95, H96, H97, H98, L30, L31, L32, L34 and L96 (12 residues in total, FIG. 2).

C. Selection of Amino Acid Use at the Positions to be Varied

Side-chain diversity is introduced into the "primary" and "somatic" libraries by incorporating either the codon NNK (which encodes all 20 amino acids, including the TAG stop codon, but not the TGA and TAA stop codons) or the codon DVT (which encodes 22% serine and 11% tyrosine, asparagine, glycine, alanine, aspartate, threonine and cysteine and using single, double, triple and quadruple degeneracy in equal ratios at each position, most closely mimics the distribution of amino acid residues for in the antigen binding sites of natural human antibodies).

EXAMPLE 2

Library Construction and Selection with the Generic Ligands

The "primary" and "somatic" libraries were assembled by PCR using the oligonucleotides listed in Table 1 and the germline V gene segments DPK9 (Cox et al., 1994, *Eur. J. Immunol.*, 24: 827) and DP-47 (Tomlinson et al., 1992, *J. Mol. Biol.*, 227: 7768). Briefly, first round of amplification was performed using pairs of 5' (back) primers in conjunction with NNK or DVT 3' (forward) primers together with the corresponding germline V gene segment as template (see Table 1). This produces eight separate DNA fragments for each of the NNK and DVT libraries. A second round of amplification was then performed using the 5' (back) primers and the 3' (forward) primers shown in Table 1 together with two of the purified fragments from the first round of amplification. This produces four separate fragments for each of the NNK and DVT libraries (a "primary" $V_H$ fragment, 5A; a "primary" $V_\kappa$ fragment, 6A; a "somatic" $V_H$ fragment, 5B; and a "somatic" $K_\kappa$ fragment, 6B).

Each of these fragments was cut and then ligated into pCLEANVH (for the $V_H$ fragments) or pCLEANVK (for the $V_\kappa$ fragments) which contain dummy $V_H$ and $V_\kappa$ domains, respectively in a version of pHEN1 which does not contain any TAG codons or peptide tags (Hoogenboom and Winter, 1992, supra). The ligations were then electroporated into the non-suppressor *E. coli.* strain HB2151. Phage from each of these libraries was produced and separately selected using immunotubes coated with 10 μg/ml of the generic ligands Protein A and Protein L for the $V_H$ and $V_\kappa$ braries, respectively. DNA from *E. coli.* infected with selected phage was then prepared and cut so that the dummy $V_\kappa$ inserts were replaced by the corresponding $V_\kappa$ libraries. Electroporation of these libraries results in the following insert library sizes: $9.21 \times 10^8$ ("primary" NNK), $5.57 \times 10^8$ ("primary" DVT), $1.00 \times 10^9$ ("somatic" NNK) and $2.38 \times 10^8$ ("somatic" DVT). As a control for pre-selection four additional libraries were created but without selection with the generic ligands Protein A and Protein L: insert library sizes for these libraries were $1.29 \times 10^9$ ("primary" NNK), $2.40 \times 10^8$ ("primary" DVT), $1.16 \times 10^9$ ("somatic" NNK) and $2.17 \times 10^8$ ("somatic" DVT).

To verify the success of the pre-selection step, DNA from the selected and unselected "primary" NNK libraries was cloned into a pUC based expression vector and electroporated into HB2151. 96 clones were picked at random from each recloned library and induced for expression of soluble scFv fragments. Production of functional scFv is assayed by ELISA using Protein L to capture the scFv and then Protein A-HRP conjugate to detect binding. Only scFv which express functional $V_H$ and $V_\kappa$ domains (no frame-shifts, stop codons, folding or expression mutations) will give a signal using this assay. The number of functional antibodies in each library (ELISA signals above background) was 5% with the unselected "primary" NNK library and 75% with the selected version of the same (FIG. 3). Sequencing of clones which were negative in the assay confirmed the presence of frame-shifts, stop codons, PCR mutations at critical framework residues and amino acids in the antigen binding site which must prevent folding and/or expression.

EXAMPLE 3

Library Selection Against Target Ligands

The "primary" and "somatic" NNK libraries (without pre-selection) were separately selected using five antigens (bovine ubiquitin, rat BIP, bovine histone, NIP-BSA and hen egg lysozyme) coated on immunotubes at various concentrations. After 2–4 rounds of selection, highly specific antibodies were obtained to all antigens except hen egg lysozyme. Clones were selected at random for sequencing demonstrating a range of antibodies to each antigen (FIG. 4).

In the second phase, phage from the pre-selected NNK and DVT libraries were mixed 1:1 to create a single "primary" library and a single "somatic" library. These libraries were then separately selected using seven antigens (FITC-BSA, human leptin, human thyroglobulin, BSA, hen egg lysozyme, mouse IgG and human IgG) coated on immunotubes at various concentrations. After 2–4 rounds of selection, highly specific antibodies were obtained to all the antigens, including hen egg lysozyme which failed to produce positives in the previous phase of selection using the libraries that had not been pre-selected using the generic ligands. Clones were selected at random for sequencing, demonstrating a range of different antibodies to each antigen (FIG. 4).

EXAMPLE 4

Effect of Pre-selection on scFv Expression and Production of Phage Bearing scFv

To further verify the outcome of the pre-selection, DNA from the unselected and pre-selected "primary" DVT libraries is cloned into a pUC based expression vector and electroporated into HB2151, yielding $10^5$ clones in both cases. 96 clones are picked at random from each recloned library and induced for expression of soluble scFv fragments. Production of functional scFv is again assayed using Protein L to capture the scFv followed by the use of Protein A-HRP to detect bound scFv. The percentage of functional antibodies in each library is 35.4% (unselected) and 84.4% (pre-selected) indicating a 2.4 fold increase in the number of functional members as a result of pre-selection with Protein A and Protein L (the increase is less pronounced than with the equivalent NNK library since the DVT codon does not encode the TAG stop codon. In the unselected NNK library, the presence of a TAG stop codon in a non-suppressor strain such as HB2151 will lead to termination and hence prevent functional scFv expression. Pre-selection of the NNK library removes clones containing TAG stop codons to produce a library in which a high proportion of members express soluble scFv.)

Figure 5A:
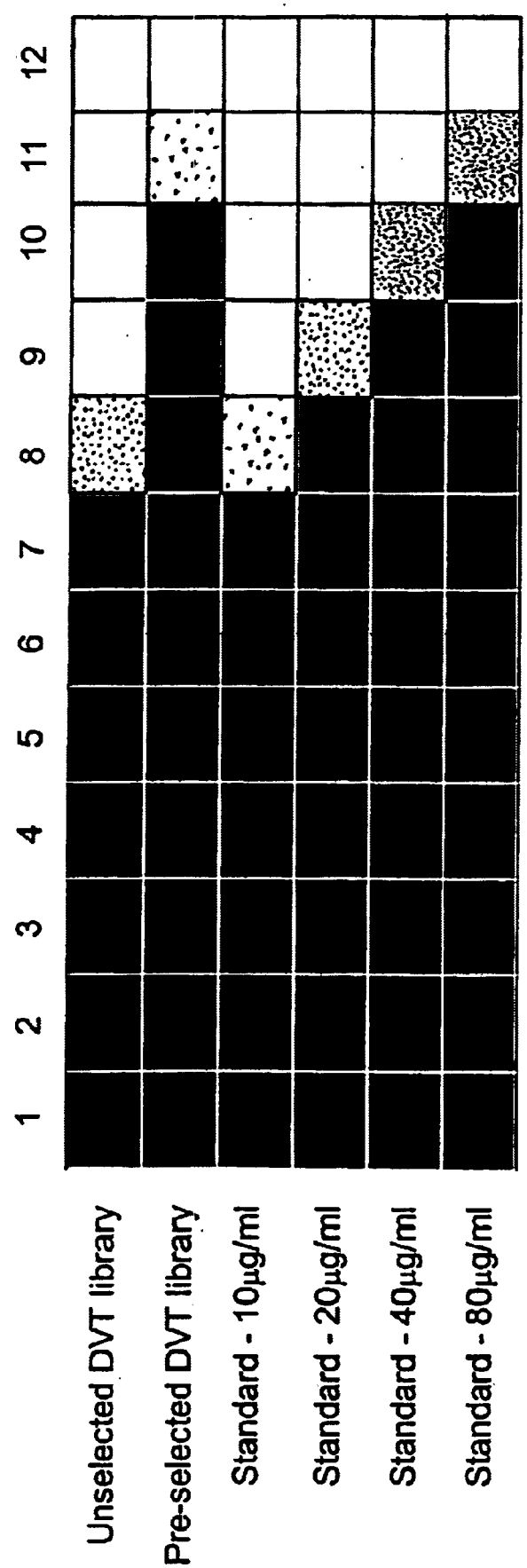
FIG. 5A presents a comparison of scFv concentration produced by the unselected and preselected "primary" DVT libraries in host cells.
Figure 5B:
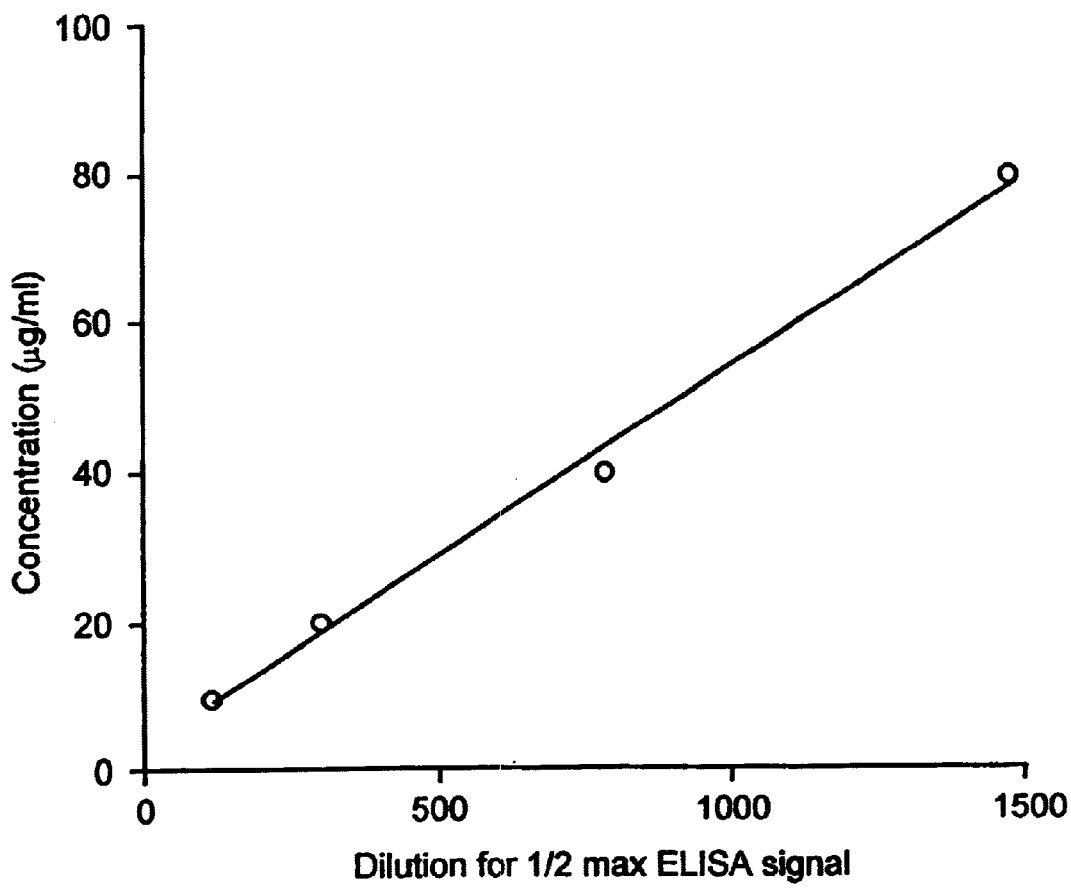
FIG. 5B shows a standard curve of ELISA as determined from known standards.

In order to assess the effect to pre-selection of the "primary" DVT library on total scFv expression, the recloned unselected and pre-selected libraries (each containing $10^5$ clones in a pUC based expression vector) are induced for polyclonal expression of scFv fragments. The concentration of expressed scFv in the supernatant is then determined by incubating two fold dilutions (columns 1–12 in FIG. 5A) of the supernatants on Protein L coated ELISA plate, followed by detection with Protein A-HRP, ScFvs of known concentration are assayed in parallel to quantify the levels of scFv expression in the unselected and pre-selected DVT libraries. These are used to plot a standard curve (FIG. 5B) and from this the expression levels of the unselected and pre-selected "primary" DVT libraries are calculated as 12.9 μg/ml and 67.1 μg/ml respectively i.e., a 5.2 fold increase in expression due to pre-selection with Protein A and Protein L.

Figure 6:
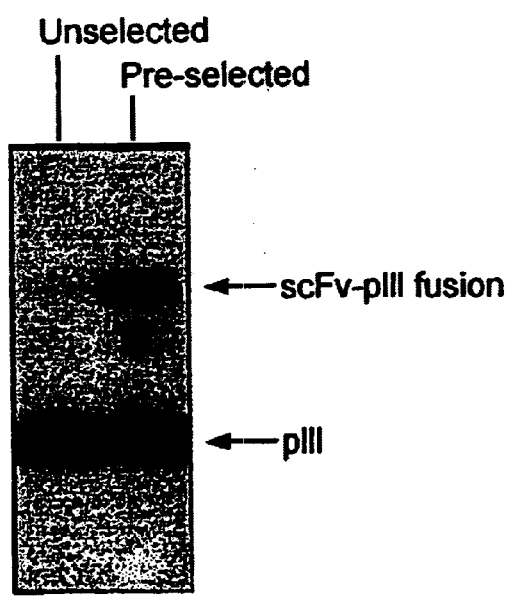
FIG. 6 presents a Western blot of phage from preselected and unselected DVT "primary" libraries, probed with an anti-phage pIII antibody in order to determine the percentage of phage bearing scFv.

To assess the amount of phage bearing scFv, the unselected and pre-selected "primary" DVT libraries are grown and polyclonal phage is produced. Equal volumes of phage from the two libraries are run under denaturing conditions on a 4–12% Bis-Tris NuPAGE Gel with MES running buffer. The resulting gel is western blotted, probed using an anti-pIII antibody and exposed to X-ray film (FIG. 6). The lower band in each case corresponds to pIII protein alone, while the higher band contains the pIII-scFv fusion protein. Quantitation of the band intensities using the software package NIH image indicates that pre-selection results in an 11.8 fold increase in the amount of fusion protein present in the phage. Indeed, 43% of the total pIII in the pre-selected phage exists as pIII-scFv fusion, suggesting that most phage particles will have at least one scFv displayed on the surface.

Hence, not only does pre-selection using generic ligands enable enrichment of functional members from a repertoire but it also leads to preferential selection of those members which are well expressed and (if required) are able to elicit a high level of display on the surface of phage without being cleaved by bacterial proteases.

TABLE 1

PCR Primers for the Assembly of the "Primary" and "Somatic" Antibody Libraries

Template

1st round of amplification:

| | | | | |
|---|---|---|---|---|
| 1A | DP-47 | 5' (back) primer | (SEQ ID NO:181) | GAGGTGCAGCTGTTGGAGTC |
| | | DVT 3' (forward) primer | (SEQ ID NO:182) | GCCCTTCACGGAGTCTGCGTAMNNTGTMNNMNNACCMNNMNNMNN-AATMNNTGAGACCCACTCCAGCCC |
| | | NNK 3' (forward) primer | (SEQ ID NO:183) | TABHTGAGACCCACTCCAGCCCGCCCTTCACGGAGTCTGCGTAAB-HTGTABHABHACCABHABHABHAA |
| 2A | DP-47 | 5' (back) primer | (SEQ ID NO:184) | CGCAGACTCCGTGAAGGGC |
| | | DVT 3' (forward) primer | (SEQ ID NO:185) | TCCCTGGCCCCAGTAGTCAAAMNNMNNMNNMNNTTTCGCACAGTA-ATATACGG |
| | | NNK 3' (forward) primer | (SEQ ID NO:186) | TCCCTGGCCCCAGTAGTCAAAABHABHABHABHTTTCGCACAGTA-ATATACGG |
| 3A | DPK9 | 5' (back) primer | (SEQ ID NO:187) | GACATCCAGATGACCCAGTC |
| | | DVT 3' (forward) primer | (SEQ ID NO:188) | ATGGGACCCCACTTTGCAAMNNGGATGCMNNATAGATCAGGAG-CTTAGGGG |
| | | NNK 3' (forward) primer | (SEQ ID NO:189) | ATGGGACCCCACTTTGCAAABHGGATGCABHATAGATCAGGAG-CTTAGGGG |
| 4A | DPK95 | 5' (back) primer | (SEQ ID NO:190) | TTGCAAAGTGGGGTCCCAT |
| | | DVT 3' (forward) primer | (SEQ ID NO:191) | CTTGGTCCCTTGGCCGAACGTMNNAGGMNNMNNMNNMNNCTGT-TGACAGTAGTAAGTTGC |
| | | NNK 3' (forward) primer | (SEQ ID NO:192) | CTTGGTCCCTTGGCCGAACGTABHAGGABHABHABHABHCTGT-TGACAGTAGTAAGTTGC |
| 1B | DP-475 | 5' (back) primer | (SEQ ID NO:193) | GAGGTGCAGCTGTTGGAGTC |
| | | DVT 3' (forward) primer | (SEQ ID NO:194) | CTGGAGCCTGGCGGACCCAMNNCATMNNATAMNNGCTAAAGGT-GAATCCAGAG |
| | | NNK 3' (forward) primer | (SEQ ID NO:195) | CTGGAGCCTGGCGGACCCAABHCATABHATAABHGCTAAAGGT-GAATCCAGAG |
| 2B | DP-475 | 5' (back) primer | (SEQ ID NO:196) | TGGGTCCGCCAGGCTCCAG |
| | | DVT 3' (forward) primer | (SEQ ID NO:197) | TCCCTGGCCCCAGTAGTCAAAMNNMNNMNNMNNTTTCGCACAG-TAATATACGG |
| | | NNK 3' (forward) primer | (SEQ ID NO:198) | TCCCTGGCCCCAGTAGTCAAAABHABHABHABHTTTCGCACAG-TAATATACGG |
| 3B | DPK95 | 5' (back) primer | (SEQ ID NO:199) | GACATCCAGATGACCCAGTC |
| | | DVT 3' (forward) primer | (SEQ ID NO:200) | CTGGTTTCTGCTGATACCAMNNTAAMNNMNNMNNAATGCTCTG-ACTTGCCCGG |
| | | NNK 3' (forward) primer | (SEQ ID NO:201) | CTGGTTTCTGCTGATACCAABHTAAABHABHABHAATGCTCTG-ACTTGCCCGG |
| 4B | DPK95 | 5' (back) primer | (SEQ ID NO:202) | TGGTATCAGCAGAAACCAGGG |
| | | DVT 3' (forward) primer | (SEQ ID NO:203) | CTTGGTCCCTTGGCCGAACGTMNNAGGGGTACTGTAACTCTGT-TGACAGTAGTAAGTTGC |
| | | NNK 3' (forward) primer | (SEQ ID NO:204) | CTTGGTCCCTTGGCCGAACGTABHAGGGGTACTGTAACTCTGT-TGACAGTAGTAAGTTGC |

2nd round of amplification:

| | | | | |
|---|---|---|---|---|
| 5A | 1A/2A | 5'(back) primer | (SEQ ID NO:205) | GTCCTCGCAACTGCGGCCCAGCCGGCCATGGCCGAGGTGCAGCT-GTTGGAGTC |
| | | 3'(forward) primer | (SEQ ID NO:206) | GAACCGCCTCCACCGCTCGAGACGGTGACCAGGGTTCCCTGGCCCCAG-TAGTCAAA |
| 6A | 3A/4A | 5'(back) primer | (SEQ ID NO:207) | AGCGGTGGAGGCGGTTCAGGCGGAGGTGGCAGCGGCGGTGGCGGG-TCGACGGACATCCAGATGACCCAGTC |
| | | 3'(forward) primer | (SEQ ID NO:208) | GAGTCATTCTCGACTTGCGGCCGCCCGTTTGATTTCCACCTTGG-TCCCTTGGCCGAACG |
| 5B | 1B/2B | 5'(back) primer | (SEQ ID NO:209) | GTCCTCGCAACTGCGGCCCAGCCGGCCATGGCCGAGG-TGCAGCTGTTGGAGTC |
| | | 3'(forward) primer | (SEQ ID NO:210) | GAACCGCCTCCACCGCTCGAGACGGTGACCAGGGTTCCCT-GGCCCCAGTAGTCAAA |
| 6B | 3B/4B | 5'(back) primer | (SEQ ID NO:211) | AGCGGTGGAGGCGGTTCAGGCGGAGGTGGCAGCGGCGGTGGCGGGTCGAC-GGACATCCAGATGACCCAGTC |
| | | 3'(forward) primer | (SEQ ID NO:212) | GAGTCATTCTCGACTTGCGGCCGCCCGTTTGATTTCCACCTTGG-TCCCTTGGCCGAACG |

EXAMPLE 5

In the above examples, a general procedure for performing the dual-tiered polypeptide selection of the present invention, in which an antibody was used as the generic ligand, was exemplified. As stated above, other ligands are also of use in the invention, either as generic or target ligands. Here, immobilized metal affinity chromatography (IMAC; Hubert and Porath, 1980, supra; see also Staples et al., U.S. Pat. No. 5,169,936) is employed as the first step in the selection of variants of a growth factor (e.g. human growth hormone, transforming growth factor or platelet-derived growth factor, all described above as possessing surface metal-binding domains) for inclusion in a repertoire of the invention as follows:

A polypeptide sequence is designed based upon the structure of a given naturally-occurring, functional growth factor molecule, and a nucleic acid molecule encoding this sequence is synthesized and mutagenized at sites of interest to create a heterogeneous pool of variants of the coding sequence and, consequently, its expressed product; these steps are accomplished by any methods known in the art, as described above. The sequence is then transcribed and translated in an appropriate expression system, and the resulting pool of polypeptide molecules is placed in a binding buffer that contains 0.020M Tris.Cl, pH 7.5, and 0.15 M NaCl.

Prior to use, one volume of Chelating Sepharose 6B™ is washed with several column volumes of water. The washed gel is then suspended in 4 volumes of 0.05M $CuCl_2.2H_2O$ for at least 30 minutes. The gel is again washed with several volumes of water to remove uncomplexed $Cu^{2+}$ and then equilibrated by washing in several volumes of 0.02M Tris.HCl buffer, pH 7.5, containing 0.15M NaCl.

The volume of equilibrated resin in the column is calculated such that polypeptide is loaded onto it in a ratio of 10 mg protein/ml gel, and the flow rate is adjusted to 6 column volumes per hour. The column is both loaded and run at 4° C. After loading is complete, the column is washed in binding buffer until the $A_{280}$ of the wash fractions measured in an ultraviolet spectrophotometer falls to baseline levels. Polypeptide molecules which are specifically bound to metallic ions on the column are then eluted by washing in 0.2M M Tris.Cl, pH 7.5, and 0.15M NaCl. This first selected pool is then dialyzed against a buffer (e.g. a physiological or sub-physiological salt buffer, such as phosphate-buffered saline) suitable for binding with a target ligand. Note that in vivo, the native growth factor binds its receptor in physiological salt; however, if it is the receptor-binding site of the molecules of the pool that is mutagenized, a lower salt concentration is used, since recovery of as full a range of variants as possible requires binding conditions of reduced stringency.

The target ligand comprises a cellular receptor for the growth factor in question. As receptors are normally membrane-anchored, it is necessary to provide as the target ligand either the extracellular domain of the receptor in cell-free form, whether the polypeptide molecules are recombinant or are cleaved from naturally-produced receptor molecules, or the membrane fraction of a lysate derived from cells which produce the receptor at a high level, such as transfected cells which contain efficiently-driven gene expression constructs that encode it. If the isolated extracellular domain of a given receptor is known to fold in such a manner as permits specific interactions with its corresponding growth factor, it is used. These target ligand molecules are immobilized on a solid support, such as a chromatography resin, and contacted with the first selected pool of polypeptides obtained in the metal-binding step. As before, the molecules are loaded onto the column and then washed; following the wash step, a substantially pure preparation of growth factor molecules is eluted from the target ligand molecules using a high-salt elution buffer (e.g. 0.5 to 1.0 M salt) to provide a repertoire of functional growth factor polypeptides according to the invention.

Other Embodiments

Other embodiments will be evident to those of skill in the art. It should be understood that the foregoing description is provided for clarity only and is merely exemplary. The spirit and scope of the present invention are not limited to the above examples, but are encompassed by the following claims.

What is claimed is:

1. A method for selecting a functional polypeptide from a repertoire of polypeptides comprising functional and non-functional polypeptides, said functional polypeptides being those which bind to a target ligand at a first binding site and to the same generic ligand at a second binding site, said generic ligand having affinity for a structural feature common to all functional members of the repertoire, said non-functional polypeptides being unable to bind to a target or generic ligand, the method comprising the steps of:
   a) contacting the repertoire with the generic ligand and selecting polypeptides bound thereto, thereby obtaining a first selected pool of polypeptides enriched for said functional polypeptides and comprising a reduced proportion of non-functional polypeptides; and
   b) contacting the first selected pool of polypeptides with a target ligand and selecting a population of polypeptides which bind to the target ligand;
   wherein said contacting steps (a) and (b) select polypeptides that bind target ligand at said first binding site and generic ligand at said second binding site.

2. The method according to claim 1, wherein the repertoire of polypeptides is contacted with a target ligand and then with the generic ligand.

3. The method according to claim 1, wherein two or more pools are selected using two or more generic ligands.

4. The method according to claim 3 wherein two or more first selected pools are pooled after selection to produce a second selected pool of polypeptides enriched for functional polypeptides.

5. The method according to claim 1, wherein two or more repertoires of polypeptides are contacted with generic ligands and first selected pools of polypeptides obtained from each repertoire are pooled to form a second selected pool of polypeptides.

6. The method according to claim 1, wherein the polypeptides of the repertoire belong to immunoglobulin superfamily.

7. The method according to claim 6, wherein the polypeptides comprise antibody or T-cell receptor polypeptides.

8. The method according to claim 7, wherein the polypeptides comprise $V_H$ or $V_\beta$ domains.

9. The method according to claim 7, wherein the polypeptides comprise $V_L$ or $V_\alpha$ domains.

10. The method according to claim 1, wherein a repertoire of polypeptides comprising $V_H$ or $V_\beta$ domains and a repertoire of polypeptides comprising $V_L$ or $V_\alpha$ domains are contacted with generic ligands and the first selected pools of polypeptides obtained for each repertoire are pooled to form a second selected pool of polypeptides.

11. The method according to claim 1, wherein the generic ligand is selected from the group consisting of a matrix of metallic ions, an organic compound, a protein, a peptide, a monoclonal antibody, a polyclonal antibody population, and a superantigen.

12. A method for detecting one or more members of a repertoire of polypeptides previously selected according to claim 1, comprising binding said one or more members to the generic ligand and detecting bound ligand.

13. The method according to claim 1, wherein said non-functional polypeptides comprises polypeptides selected from the group consisting of: improperly folded polypeptides, polypeptides comprising missense mutations, and polypeptides comprising frameshift mutations.

14. The method according to claim 4, wherein said first selected pools of polypeptides obtained from each repertoire are each contacted with different target ligands prior to being pooled to form said second selected set of pooled polypeptides.

15. The method according to claim 4, wherein sequences encoding said second selected pool of polypeptides are combined at the genetic level in a vector which encodes a polypeptide having binding sites for two generic ligands.

16. The method according to claim 14, wherein sequences encoding said second selected pool of polypeptides are combined at the genetic level in a vector which encodes a polypeptide having binding sites for two generic ligands and two target ligands.

17. The method according to claim 11, wherein the superantigen is Protein A or Protein L.

18. The method according to claim 5, wherein said first selected pools of polypeptides obtained from each repertoire are each contacted with different target ligands prior to being pooled to form said second selected set of pooled polypeptides.

19. The method according to claim 10, wherein said first selected pools of polypeptides obtained from each repertoire are each contacted with different target ligands prior to being pooled to form said second selected set of pooled polypeptides.

20. The method according to claim 5, wherein sequences encoding said second selected set of pooled polypeptides are combined at the genetic level in a vector which encodes a polypeptide having binding sites for two generic ligands.

21. The method according to claim 10, wherein sequences encoding said second selected set of pooled polypeptides are combined at the genetic level in a vector which encodes a polypeptide having binding sites for two generic ligands.

* * * * *

SEQUENCE LISTING

```
<160> NUMBER OF SEQ ID NOS: 212

<210> SEQ ID NO 1
<211> LENGTH: 720
<212> TYPE: DNA
<213> ORGANISM: Homo sapiens

<400> SEQUENCE: 1
gaggtgcagc tgttggagtc tgggggaggc ttggtacagc ctgggggtc cctgagactc      60 tcctgtgcag cctctggatt caccttagc agctatgcca tgagctgggt ccgccaggct    120
ccagggaagg ggctggagtg ggtctcagct attagtggta gtggtggtag cacatactac    180
gcagactccg tgaagggccg gttcaccatc tccagagaca attccaagaa cacgctgtat    240
ctgcaaatga acagcctgag agccgaggac acggccgtat attactgtgc gaaaagttat    300
ggtgcttttg actactgggg ccagggaacc ctggtcaccg tctcgagcgg tggaggcggt    360
tcaggcggag gtggcagcgg cggtggcggg tcgacggaca tccagatgac ccagtctcca    420
```

```
tcctccctgt ctgcatctgt aggagacaga gtcaccatca cttgccgggc aagtcagagc      480
attagcagct atttaaattg gtatcagcag aaaccaggga aagcccctaa gctcctgatc      540
tatgctgcat ccagtttgca aagtggggtc ccatcaaggt tcagtggcag tggatctggg      600
acagatttca ctctcaccat cagcagtctg caacctgaag attttgcaac ttactactgt      660
caacagagtt acagtacccc taatacgttc ggccaaggga ccaaggtgga aatcaaacgg      720
```

<210> SEQ ID NO 2
<211> LENGTH: 240
<212> TYPE: PRT
<213> ORGANISM: Homo sapiens

<400> SEQUENCE: 2

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ala Ala Ser Ser Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ser Tyr
    210                 215                 220

Ser Thr Pro Asn Thr Phe Gly Gln Gly Thr Lys Val Glu Ile Lys Arg
225                 230                 235                 240
```

<210> SEQ ID NO 3
<211> LENGTH: 5
<212> TYPE: PRT
<213> ORGANISM: Homo sapiens

<400> SEQUENCE: 3

```
Ser Tyr Ala Met Ser
 1               5
```

<210> SEQ ID NO 4
<211> LENGTH: 17
<212> TYPE: PRT

-continued

```
<213> ORGANISM: Homo sapiens

<400> SEQUENCE: 4

Ile Ile Gly Ser Glu Gly Trp Pro Thr Ile Tyr Ala Asp Ser Val Lys
 1               5                  10                  15
Gly

<210> SEQ ID NO 5
<211> LENGTH: 7
<212> TYPE: PRT
<213> ORGANISM: Homo sapiens

<400> SEQUENCE: 5

Gly Gly Ser Met Phe Asp Tyr
 1               5

<210> SEQ ID NO 6
<211> LENGTH: 11
<212> TYPE: PRT
<213> ORGANISM: Homo sapiens

<400> SEQUENCE: 6

Arg Ala Ser Gln Ser Ile Ser Ser Tyr Leu Asn
 1               5                  10

<210> SEQ ID NO 7
<211> LENGTH: 7
<212> TYPE: PRT
<213> ORGANISM: Homo sapiens

<400> SEQUENCE: 7

Arg Ala Ser Ser Leu Gln Ser
 1               5

<210> SEQ ID NO 8
<211> LENGTH: 9
<212> TYPE: PRT
<213> ORGANISM: Homo sapiens

<400> SEQUENCE: 8

Gln Gln Ser Ser Asn Thr Pro Tyr Thr
 1               5

<210> SEQ ID NO 9
<211> LENGTH: 5
<212> TYPE: PRT
<213> ORGANISM: Homo sapiens

<400> SEQUENCE: 9

Ala Tyr Ala Met Thr
 1               5

<210> SEQ ID NO 10
<211> LENGTH: 17
<212> TYPE: PRT
<213> ORGANISM: Homo sapiens

<400> SEQUENCE: 10

Ala Ile Ser Gly Ser Gly Gly Ser Thr Tyr Tyr Ala Asp Ser Val Lys
 1               5                  10                  15
Gly

<210> SEQ ID NO 11
```

```
<211> LENGTH: 7
<212> TYPE: PRT
<213> ORGANISM: Homo sapiens

<400> SEQUENCE: 11

Lys Ala Ser Ser Phe Asp Tyr
  1               5

<210> SEQ ID NO 12
<211> LENGTH: 7
<212> TYPE: PRT
<213> ORGANISM: Homo sapiens

<400> SEQUENCE: 12

Ala Ala Ser Ser Leu Gln Ser
  1               5

<210> SEQ ID NO 13
<211> LENGTH: 9
<212> TYPE: PRT
<213> ORGANISM: Homo sapiens

<400> SEQUENCE: 13

Gln Gln Ser Tyr Ser Thr Pro Ser Thr
  1               5

<210> SEQ ID NO 14
<211> LENGTH: 17
<212> TYPE: PRT
<213> ORGANISM: Homo sapiens

<400> SEQUENCE: 14

Leu Ile Ser Pro Leu Gly Lys Asp Thr Ser Tyr Ala Asp Ser Val Lys
  1               5                  10                  15

Gly

<210> SEQ ID NO 15
<211> LENGTH: 7
<212> TYPE: PRT
<213> ORGANISM: Homo sapiens

<400> SEQUENCE: 15

Arg Ala Gly Ile Phe Asp Tyr
  1               5

<210> SEQ ID NO 16
<211> LENGTH: 7
<212> TYPE: PRT
<213> ORGANISM: Homo sapiens

<400> SEQUENCE: 16

His Ala Ser Arg Leu Gln Ser
  1               5

<210> SEQ ID NO 17
<211> LENGTH: 9
<212> TYPE: PRT
<213> ORGANISM: Homo sapiens

<400> SEQUENCE: 17

Gln Gln Tyr Arg Leu Arg Pro Leu Thr
  1               5

<210> SEQ ID NO 18
```

```
<211> LENGTH: 17
<212> TYPE: PRT
<213> ORGANISM: Homo sapiens

<400> SEQUENCE: 18

Gly Ile Arg Arg Val Gly Gln Ala Thr Ser Tyr Ala Asp Ser Val Lys
 1               5                  10                  15

Gly

<210> SEQ ID NO 19
<211> LENGTH: 7
<212> TYPE: PRT
<213> ORGANISM: Homo sapiens

<400> SEQUENCE: 19

Gly Gly Arg Leu Phe Asp Tyr
 1               5

<210> SEQ ID NO 20
<211> LENGTH: 7
<212> TYPE: PRT
<213> ORGANISM: Homo sapiens

<400> SEQUENCE: 20

Tyr Ala Ser His Leu Gln Ser
 1               5

<210> SEQ ID NO 21
<211> LENGTH: 9
<212> TYPE: PRT
<213> ORGANISM: Homo sapiens

<400> SEQUENCE: 21

Gln Gln Tyr Arg Leu Arg Pro Leu Thr
 1               5

<210> SEQ ID NO 22
<211> LENGTH: 17
<212> TYPE: PRT
<213> ORGANISM: Homo sapiens

<400> SEQUENCE: 22

Ala Ile Asn Thr Lys Gly Met Thr Thr Asp Tyr Ala Asp Ser Val Lys
 1               5                  10                  15

Gly

<210> SEQ ID NO 23
<211> LENGTH: 7
<212> TYPE: PRT
<213> ORGANISM: Homo sapiens

<400> SEQUENCE: 23

Gly Ser Gln Ala Phe Asp Tyr
 1               5

<210> SEQ ID NO 24
<211> LENGTH: 7
<212> TYPE: PRT
<213> ORGANISM: Homo sapiens

<400> SEQUENCE: 24

Gln Ala Ser Phe Leu Gln Ser
 1               5
```

```
<210> SEQ ID NO 25
<211> LENGTH: 9
<212> TYPE: PRT
<213> ORGANISM: Homo sapiens

<400> SEQUENCE: 25

Gln Gln Gly Tyr Asn Lys Pro Arg Thr
  1               5

<210> SEQ ID NO 26
<211> LENGTH: 5
<212> TYPE: PRT
<213> ORGANISM: Homo sapiens

<400> SEQUENCE: 26

Asn Tyr Gln Met His
  1               5

<210> SEQ ID NO 27
<211> LENGTH: 7
<212> TYPE: PRT
<213> ORGANISM: Homo sapiens

<400> SEQUENCE: 27

Gly Thr Arg Arg Phe Asp Tyr
  1               5

<210> SEQ ID NO 28
<211> LENGTH: 9
<212> TYPE: PRT
<213> ORGANISM: Homo sapiens

<400> SEQUENCE: 28

Gln Gln Ser Tyr Ser Thr Pro Val Thr
  1               5

<210> SEQ ID NO 29
<211> LENGTH: 17
<212> TYPE: PRT
<213> ORGANISM: Homo sapiens

<400> SEQUENCE: 29

Ala Ile Ser Pro Lys Gly Arg Arg Thr Tyr Tyr Ala Asp Ser Val Lys
  1               5                  10                  15

Gly

<210> SEQ ID NO 30
<211> LENGTH: 7
<212> TYPE: PRT
<213> ORGANISM: Homo sapiens

<400> SEQUENCE: 30

Arg Asp Lys Leu Phe Asp Tyr
  1               5

<210> SEQ ID NO 31
<211> LENGTH: 7
<212> TYPE: PRT
<213> ORGANISM: Homo sapiens

<400> SEQUENCE: 31

Glu Ala Ser Thr Leu Gln Ser
  1               5
```

<210> SEQ ID NO 32
<211> LENGTH: 9
<212> TYPE: PRT
<213> ORGANISM: Homo sapiens

<400> SEQUENCE: 32

Gln Gln Glu Lys Met Val Pro Leu Thr
 1               5

<210> SEQ ID NO 33
<211> LENGTH: 17
<212> TYPE: PRT
<213> ORGANISM: Homo sapiens

<400> SEQUENCE: 33

Arg Ile Thr Pro Ala Gly Arg Thr Thr Tyr Ala Asp Ser Val Lys
 1               5                  10                  15

Gly

<210> SEQ ID NO 34
<211> LENGTH: 7
<212> TYPE: PRT
<213> ORGANISM: Homo sapiens

<400> SEQUENCE: 34

Pro Ser Pro Pro Phe Asp Tyr
 1               5

<210> SEQ ID NO 35
<211> LENGTH: 7
<212> TYPE: PRT
<213> ORGANISM: Homo sapiens

<400> SEQUENCE: 35

His Ala Ser Ile Leu Gln Ser
 1               5

<210> SEQ ID NO 36
<211> LENGTH: 9
<212> TYPE: PRT
<213> ORGANISM: Homo sapiens

<400> SEQUENCE: 36

Gln Gln Gly Gln His Arg Pro Leu Thr
 1               5

<210> SEQ ID NO 37
<211> LENGTH: 17
<212> TYPE: PRT
<213> ORGANISM: Homo sapiens

<400> SEQUENCE: 37

Arg Ile Thr Pro Ala Gly His Arg Thr Tyr Tyr Ala Asp Ser Val Lys
 1               5                  10                  15

Gly

<210> SEQ ID NO 38
<211> LENGTH: 7
<212> TYPE: PRT
<213> ORGANISM: Homo sapiens

<400> SEQUENCE: 38

Gln Val Ser Arg Phe Asp Tyr
 1               5

<210> SEQ ID NO 39
<211> LENGTH: 17
<212> TYPE: PRT
<213> ORGANISM: Homo sapiens

<400> SEQUENCE: 39

Thr Ile Ser Pro Gln Gly Leu Arg Thr Thr Tyr Ala Asp Ser Val Lys
 1               5                   10                  15
Gly

<210> SEQ ID NO 40
<211> LENGTH: 7
<212> TYPE: PRT
<213> ORGANISM: Homo sapiens

<400> SEQUENCE: 40

Gly Arg Pro Arg Phe Asp Tyr
 1               5

<210> SEQ ID NO 41
<211> LENGTH: 17
<212> TYPE: PRT
<213> ORGANISM: Homo sapiens

<400> SEQUENCE: 41

Thr Ile Ser Pro Gln Gly Leu Arg Thr Thr Tyr Ala Asp Ser Val Lys
 1               5                   10                  15
Gly

<210> SEQ ID NO 42
<211> LENGTH: 7
<212> TYPE: PRT
<213> ORGANISM: Homo sapiens

<400> SEQUENCE: 42

Thr Asn Arg Ser Phe Asp Tyr
 1               5

<210> SEQ ID NO 43
<211> LENGTH: 7
<212> TYPE: PRT
<213> ORGANISM: Homo sapiens

<400> SEQUENCE: 43

Arg Ala Ser Arg Leu Gln Ser
 1               5

<210> SEQ ID NO 44
<211> LENGTH: 9
<212> TYPE: PRT
<213> ORGANISM: Homo sapiens

<400> SEQUENCE: 44

Gln Gln Arg Ala Lys Lys Pro Pro Thr
 1               5

<210> SEQ ID NO 45
<211> LENGTH: 5
<212> TYPE: PRT
<213> ORGANISM: Homo sapiens

<400> SEQUENCE: 45

Lys Tyr Arg Met Phe
 1               5

<210> SEQ ID NO 46
<211> LENGTH: 7
<212> TYPE: PRT
<213> ORGANISM: Homo sapiens

<400> SEQUENCE: 46

Gly Arg Trp Pro Phe Asp Tyr
 1               5

<210> SEQ ID NO 47
<211> LENGTH: 11
<212> TYPE: PRT
<213> ORGANISM: Homo sapiens

<400> SEQUENCE: 47

Arg Ala Ser Gln Ser Ile Asn Glu Asn Leu Ser
 1               5                  10

<210> SEQ ID NO 48
<211> LENGTH: 9
<212> TYPE: PRT
<213> ORGANISM: Homo sapiens

<400> SEQUENCE: 48

Gln Gln Ser Tyr Ser Thr Pro His Thr
 1               5

<210> SEQ ID NO 49
<211> LENGTH: 5
<212> TYPE: PRT
<213> ORGANISM: Homo sapiens

<400> SEQUENCE: 49

Arg Tyr Arg Met His
 1               5

<210> SEQ ID NO 50
<211> LENGTH: 7
<212> TYPE: PRT
<213> ORGANISM: Homo sapiens

<400> SEQUENCE: 50

Asn Glu Pro Arg Phe Asp Tyr
 1               5

<210> SEQ ID NO 51
<211> LENGTH: 11
<212> TYPE: PRT
<213> ORGANISM: Homo sapiens

<400> SEQUENCE: 51

Arg Ala Ser Gln Ser Ile Phe Met Arg Leu Asn
 1               5                  10

<210> SEQ ID NO 52
<211> LENGTH: 5
<212> TYPE: PRT
<213> ORGANISM: Homo sapiens

<400> SEQUENCE: 52

Arg Tyr Arg Met Gly

```
                   1               5

<210> SEQ ID NO 53
<211> LENGTH: 7
<212> TYPE: PRT
<213> ORGANISM: Homo sapiens

<400> SEQUENCE: 53

Gly Tyr Arg Lys Phe Asp Tyr
 1               5

<210> SEQ ID NO 54
<211> LENGTH: 11
<212> TYPE: PRT
<213> ORGANISM: Homo sapiens

<400> SEQUENCE: 54

Arg Ala Ser Gln Ser Ile Ser Thr Leu Leu Asn
 1               5                  10

<210> SEQ ID NO 55
<211> LENGTH: 9
<212> TYPE: PRT
<213> ORGANISM: Homo sapiens

<400> SEQUENCE: 55

Gln Gln Ser Tyr Ser Thr Pro Leu Thr
 1               5

<210> SEQ ID NO 56
<211> LENGTH: 11
<212> TYPE: PRT
<213> ORGANISM: Homo sapiens

<400> SEQUENCE: 56

Arg Ala Ser Gln Ser Ile Gly Pro Phe Leu Ser
 1               5                  10

<210> SEQ ID NO 57
<211> LENGTH: 9
<212> TYPE: PRT
<213> ORGANISM: Homo sapiens

<400> SEQUENCE: 57

Gln Gln Ser Tyr Ser Thr Pro Pro Thr
 1               5

<210> SEQ ID NO 58
<211> LENGTH: 11
<212> TYPE: PRT
<213> ORGANISM: Homo sapiens

<400> SEQUENCE: 58

Arg Ala Ser Gln Ser Ile Leu Arg Thr Leu Asn
 1               5                  10

<210> SEQ ID NO 59
<211> LENGTH: 9
<212> TYPE: PRT
<213> ORGANISM: Homo sapiens

<400> SEQUENCE: 59

Gln Gln Ser Tyr Ser Thr Pro Gly Thr
 1               5
```

<210> SEQ ID NO 60
<211> LENGTH: 17
<212> TYPE: PRT
<213> ORGANISM: Homo sapiens

<400> SEQUENCE: 60

Arg Ile Pro Ala Arg Gly Thr Val Thr His Tyr Ala Asp Ser Val Lys
 1               5                  10                  15
Gly

<210> SEQ ID NO 61
<211> LENGTH: 7
<212> TYPE: PRT
<213> ORGANISM: Homo sapiens

<400> SEQUENCE: 61

Gly Gly Leu Arg Phe Asp Tyr
 1               5

<210> SEQ ID NO 62
<211> LENGTH: 7
<212> TYPE: PRT
<213> ORGANISM: Homo sapiens

<400> SEQUENCE: 62

His Ala Ser Ala Leu Gln Ser
 1               5

<210> SEQ ID NO 63
<211> LENGTH: 9
<212> TYPE: PRT
<213> ORGANISM: Homo sapiens

<400> SEQUENCE: 63

Gln Gln Ser Tyr Arg Lys Pro Thr Thr
 1               5

<210> SEQ ID NO 64
<211> LENGTH: 17
<212> TYPE: PRT
<213> ORGANISM: Homo sapiens

<400> SEQUENCE: 64

Gly Ile Ser His Thr Gly Ser Asn Thr Arg Tyr Ala Asp Ser Val Lys
 1               5                  10                  15
Gly

<210> SEQ ID NO 65
<211> LENGTH: 7
<212> TYPE: PRT
<213> ORGANISM: Homo sapiens

<400> SEQUENCE: 65

Arg His Lys Gly Phe Asp Tyr
 1               5

<210> SEQ ID NO 66
<211> LENGTH: 7
<212> TYPE: PRT
<213> ORGANISM: Homo sapiens

<400> SEQUENCE: 66

Arg Ala Ser Thr Leu Gln Ser

<210> SEQ ID NO 67
<211> LENGTH: 9
<212> TYPE: PRT
<213> ORGANISM: Homo sapiens

<400> SEQUENCE: 67

Gln Gln Gly Tyr Arg Phe Pro Ala Thr
 1               5

<210> SEQ ID NO 68
<211> LENGTH: 17
<212> TYPE: PRT
<213> ORGANISM: Homo sapiens

<400> SEQUENCE: 68

Arg Ile Ala Pro Glu Gly Gly Arg Thr Lys Tyr Ala Asp Ser Val Lys
 1               5                  10                  15

Gly

<210> SEQ ID NO 69
<211> LENGTH: 7
<212> TYPE: PRT
<213> ORGANISM: Homo sapiens

<400> SEQUENCE: 69

Gly Arg Tyr Trp Phe Asp Tyr
 1               5

<210> SEQ ID NO 70
<211> LENGTH: 9
<212> TYPE: PRT
<213> ORGANISM: Homo sapiens

<400> SEQUENCE: 70

Gln Gln Ser Arg Asn Ala Pro Thr Thr
 1               5

<210> SEQ ID NO 71
<211> LENGTH: 17
<212> TYPE: PRT
<213> ORGANISM: Homo sapiens

<400> SEQUENCE: 71

Thr Ile Ser Tyr Leu Gly Glu Lys Thr Arg Tyr Ala Asp Ser Val Lys
 1               5                  10                  15

Gly

<210> SEQ ID NO 72
<211> LENGTH: 7
<212> TYPE: PRT
<213> ORGANISM: Homo sapiens

<400> SEQUENCE: 72

Ser Arg Arg Thr Phe Asp Tyr
 1               5

<210> SEQ ID NO 73
<211> LENGTH: 7
<212> TYPE: PRT
<213> ORGANISM: Homo sapiens

<400> SEQUENCE: 73

Lys Ala Ser Thr Leu Gln Ser
  1               5

<210> SEQ ID NO 74
<211> LENGTH: 9
<212> TYPE: PRT
<213> ORGANISM: Homo sapiens

<400> SEQUENCE: 74

Gln Gln Arg Ser Arg Pro Pro Ala Thr
  1               5

<210> SEQ ID NO 75
<211> LENGTH: 5
<212> TYPE: PRT
<213> ORGANISM: Homo sapiens

<400> SEQUENCE: 75

Arg Tyr Gly Met His
  1               5

<210> SEQ ID NO 76
<211> LENGTH: 7
<212> TYPE: PRT
<213> ORGANISM: Homo sapiens

<400> SEQUENCE: 76

Arg Gly Leu Gly Phe Asp Tyr
  1               5

<210> SEQ ID NO 77
<211> LENGTH: 5
<212> TYPE: PRT
<213> ORGANISM: Homo sapiens

<400> SEQUENCE: 77

Ser Tyr Arg Met Val
  1               5

<210> SEQ ID NO 78
<211> LENGTH: 7
<212> TYPE: PRT
<213> ORGANISM: Homo sapiens

<400> SEQUENCE: 78

Arg Gly Met Ala Phe Asp Tyr
  1               5

<210> SEQ ID NO 79
<211> LENGTH: 5
<212> TYPE: PRT
<213> ORGANISM: Homo sapiens

<400> SEQUENCE: 79

Lys Tyr Asn Met His
  1               5

<210> SEQ ID NO 80
<211> LENGTH: 7
<212> TYPE: PRT
<213> ORGANISM: Homo sapiens

<400> SEQUENCE: 80

Ala Arg Trp Arg Phe Asp Tyr

```
                    1               5

<210> SEQ ID NO 81
<211> LENGTH: 9
<212> TYPE: PRT
<213> ORGANISM: Homo sapiens

<400> SEQUENCE: 81

Gln Gln Ser Tyr Ser Thr Pro Ile Thr
  1               5

<210> SEQ ID NO 82
<211> LENGTH: 7
<212> TYPE: PRT
<213> ORGANISM: Homo sapiens

<400> SEQUENCE: 82

Thr Pro Arg Pro Phe Asp Tyr
  1               5

<210> SEQ ID NO 83
<211> LENGTH: 11
<212> TYPE: PRT
<213> ORGANISM: Homo sapiens

<400> SEQUENCE: 83

Arg Ala Ser Gln Ser Ile Gln Met Gly Leu Ser
  1               5                  10

<210> SEQ ID NO 84
<211> LENGTH: 9
<212> TYPE: PRT
<213> ORGANISM: Homo sapiens

<400> SEQUENCE: 84

Gln Gln Ser Tyr Ser Thr Pro Asn Thr
  1               5

<210> SEQ ID NO 85
<211> LENGTH: 11
<212> TYPE: PRT
<213> ORGANISM: Homo sapiens

<400> SEQUENCE: 85

Arg Ala Ser Gln Ser Ile Ser Glu Asn Leu Leu
  1               5                  10

<210> SEQ ID NO 86
<211> LENGTH: 17
<212> TYPE: PRT
<213> ORGANISM: Homo sapiens

<400> SEQUENCE: 86

Thr Ile Ser Pro Tyr Gly Lys Gln Thr Arg Tyr Ala Asp Ser Val Lys
  1               5                  10                  15
Gly

<210> SEQ ID NO 87
<211> LENGTH: 7
<212> TYPE: PRT
<213> ORGANISM: Homo sapiens

<400> SEQUENCE: 87

Lys Ser Gln His Phe Asp Tyr
```

-continued

<210> SEQ ID NO 88
<211> LENGTH: 7
<212> TYPE: PRT
<213> ORGANISM: Homo sapiens

<400> SEQUENCE: 88

Ala Ala Ser Arg Leu Gln Ser
 1               5

<210> SEQ ID NO 89
<211> LENGTH: 9
<212> TYPE: PRT
<213> ORGANISM: Homo sapiens

<400> SEQUENCE: 89

Gln Gln Arg Gly Gly Gly Pro Pro Thr
 1               5

<210> SEQ ID NO 90
<211> LENGTH: 17
<212> TYPE: PRT
<213> ORGANISM: Homo sapiens

<400> SEQUENCE: 90

Thr Ile Thr Pro Arg Gly Ser Leu Thr Ser Tyr Ala Asp Ser Val Lys
 1               5                  10                  15
Gly

<210> SEQ ID NO 91
<211> LENGTH: 7
<212> TYPE: PRT
<213> ORGANISM: Homo sapiens

<400> SEQUENCE: 91

Thr Ala Pro Pro Phe Asp Tyr
 1               5

<210> SEQ ID NO 92
<211> LENGTH: 9
<212> TYPE: PRT
<213> ORGANISM: Homo sapiens

<400> SEQUENCE: 92

Gln Gln Ser Gln Arg Lys Pro Ser Thr
 1               5

<210> SEQ ID NO 93
<211> LENGTH: 17
<212> TYPE: PRT
<213> ORGANISM: Homo sapiens

<400> SEQUENCE: 93

Gly Ile Ser Ala Tyr Gly Thr Val Thr Tyr Tyr Ala Asp Ser Val Lys
 1               5                  10                  15
Gly

<210> SEQ ID NO 94
<211> LENGTH: 7
<212> TYPE: PRT
<213> ORGANISM: Homo sapiens

<400> SEQUENCE: 94

Arg Arg Ala Gly Phe Asp Tyr
 1               5

<210> SEQ ID NO 95
<211> LENGTH: 9
<212> TYPE: PRT
<213> ORGANISM: Homo sapiens

<400> SEQUENCE: 95

Gln Gln Pro Arg His Met Pro Gln Thr
 1               5

<210> SEQ ID NO 96
<211> LENGTH: 17
<212> TYPE: PRT
<213> ORGANISM: Homo sapiens

<400> SEQUENCE: 96

Ser Ile Thr Asn Ser Gly Leu Ala Thr Ala Tyr Ala Asp Ser Val Lys
 1               5                  10                  15
Gly

<210> SEQ ID NO 97
<211> LENGTH: 7
<212> TYPE: PRT
<213> ORGANISM: Homo sapiens

<400> SEQUENCE: 97

Arg Ser Phe Arg Phe Asp Tyr
 1               5

<210> SEQ ID NO 98
<211> LENGTH: 9
<212> TYPE: PRT
<213> ORGANISM: Homo sapiens

<400> SEQUENCE: 98

Gln Gln Arg His Thr Asn Pro Pro Thr
 1               5

<210> SEQ ID NO 99
<211> LENGTH: 17
<212> TYPE: PRT
<213> ORGANISM: Homo sapiens

<400> SEQUENCE: 99

Gly Ile Thr Thr Arg Gly Gln Thr Thr Arg Tyr Ala Asp Ser Val Lys
 1               5                  10                  15
Gly

<210> SEQ ID NO 100
<211> LENGTH: 7
<212> TYPE: PRT
<213> ORGANISM: Homo sapiens

<400> SEQUENCE: 100

Thr Tyr Pro Lys Phe Asp Tyr
 1               5

<210> SEQ ID NO 101
<211> LENGTH: 7
<212> TYPE: PRT
<213> ORGANISM: Homo sapiens

<400> SEQUENCE: 101

Asn Ala Ser Arg Leu Gln Ser
 1               5

<210> SEQ ID NO 102
<211> LENGTH: 9
<212> TYPE: PRT
<213> ORGANISM: Homo sapiens

<400> SEQUENCE: 102

Gln Gln Ser Lys Leu Ser Pro Val Thr
 1               5

<210> SEQ ID NO 103
<211> LENGTH: 17
<212> TYPE: PRT
<213> ORGANISM: Homo sapiens

<400> SEQUENCE: 103

Thr Ile Pro Ala Arg Gly Gly His Thr Lys Tyr Ala Asp Ser Val Lys
 1               5                  10                  15

Gly

<210> SEQ ID NO 104
<211> LENGTH: 7
<212> TYPE: PRT
<213> ORGANISM: Homo sapiens

<400> SEQUENCE: 104

Ser Ala Lys Ala Phe Asp Tyr
 1               5

<210> SEQ ID NO 105
<211> LENGTH: 11
<212> TYPE: PRT
<213> ORGANISM: Homo sapiens

<400> SEQUENCE: 105

Arg Ala Ser Arg Ser Ile Ser Ser Tyr Leu Asn
 1               5                  10

<210> SEQ ID NO 106
<211> LENGTH: 7
<212> TYPE: PRT
<213> ORGANISM: Homo sapiens

<400> SEQUENCE: 106

Gln Ala Ser Asn Leu Gln Ser
 1               5

<210> SEQ ID NO 107
<211> LENGTH: 9
<212> TYPE: PRT
<213> ORGANISM: Homo sapiens

<400> SEQUENCE: 107

Gln Gln Arg Ser Ala Gly Pro Leu Thr
 1               5

<210> SEQ ID NO 108
<211> LENGTH: 5
<212> TYPE: PRT
<213> ORGANISM: Homo sapiens -continued

```
<400> SEQUENCE: 108

Met Tyr Arg Met Gly
 1               5

<210> SEQ ID NO 109
<211> LENGTH: 7
<212> TYPE: PRT
<213> ORGANISM: Homo sapiens

<400> SEQUENCE: 109

Arg Thr Phe Arg Phe Asp Tyr
 1               5

<210> SEQ ID NO 110
<211> LENGTH: 11
<212> TYPE: PRT
<213> ORGANISM: Homo sapiens

<400> SEQUENCE: 110

Arg Ala Ser Gln Ser Ile Arg Ser Arg Leu Ser
 1               5                  10

<210> SEQ ID NO 111
<211> LENGTH: 9
<212> TYPE: PRT
<213> ORGANISM: Homo sapiens

<400> SEQUENCE: 111

Gln Gln Ser Tyr Ser Thr Pro Arg Thr
 1               5

<210> SEQ ID NO 112
<211> LENGTH: 5
<212> TYPE: PRT
<213> ORGANISM: Homo sapiens

<400> SEQUENCE: 112

Ser Tyr Ala Met Thr
 1               5

<210> SEQ ID NO 113
<211> LENGTH: 7
<212> TYPE: PRT
<213> ORGANISM: Homo sapiens

<400> SEQUENCE: 113

Lys Thr Gly Met Phe Asp Tyr
 1               5

<210> SEQ ID NO 114
<211> LENGTH: 11
<212> TYPE: PRT
<213> ORGANISM: Homo sapiens

<400> SEQUENCE: 114

Arg Ala Ser Gln Ser Ile Arg Thr Arg Leu Arg
 1               5                  10

<210> SEQ ID NO 115
<211> LENGTH: 17
<212> TYPE: PRT
<213> ORGANISM: Homo sapiens

<400> SEQUENCE: 115
```

Ala Ile Asn Arg Arg Gly Ser Ala Thr Arg Tyr Ala Asp Ser Val Lys
 1               5                  10                  15
Gly

<210> SEQ ID NO 116
<211> LENGTH: 7
<212> TYPE: PRT
<213> ORGANISM: Homo sapiens

<400> SEQUENCE: 116

Tyr Leu His Thr Phe Asp Tyr
 1               5

<210> SEQ ID NO 117
<211> LENGTH: 9
<212> TYPE: PRT
<213> ORGANISM: Homo sapiens

<400> SEQUENCE: 117

Gln His Pro Gly Leu Arg Pro Gly Thr
 1               5

<210> SEQ ID NO 118
<211> LENGTH: 7
<212> TYPE: PRT
<213> ORGANISM: Homo sapiens

<400> SEQUENCE: 118

Ala Ala Ser Ala Leu Gln Ser
 1               5

<210> SEQ ID NO 119
<211> LENGTH: 9
<212> TYPE: PRT
<213> ORGANISM: Homo sapiens

<400> SEQUENCE: 119

Gln Gln Ser Asp Leu Pro Pro Ser Thr
 1               5

<210> SEQ ID NO 120
<211> LENGTH: 5
<212> TYPE: PRT
<213> ORGANISM: Homo sapiens

<400> SEQUENCE: 120

Arg Tyr Arg Met Trp
 1               5

<210> SEQ ID NO 121
<211> LENGTH: 7
<212> TYPE: PRT
<213> ORGANISM: Homo sapiens

<400> SEQUENCE: 121

Arg Pro Ser Thr Phe Asp Tyr
 1               5

<210> SEQ ID NO 122
<211> LENGTH: 11
<212> TYPE: PRT
<213> ORGANISM: Homo sapiens

<400> SEQUENCE: 122

Arg Ala Ser Gln Ser Ile Ala Lys Asn Leu Ser
1               5                   10

<210> SEQ ID NO 123
<211> LENGTH: 11
<212> TYPE: PRT
<213> ORGANISM: Homo sapiens

<400> SEQUENCE: 123

Arg Ala Ser Gln Ser Ile Lys Gln Arg Leu His
1               5                   10

<210> SEQ ID NO 124
<211> LENGTH: 17
<212> TYPE: PRT
<213> ORGANISM: Homo sapiens

<400> SEQUENCE: 124

Ser Ile Ala Pro Ala Gly Arg His Thr Tyr Tyr Ala Asp Ser Val Lys
1               5                   10                  15

Gly

<210> SEQ ID NO 125
<211> LENGTH: 7
<212> TYPE: PRT
<213> ORGANISM: Homo sapiens

<400> SEQUENCE: 125

Asn Ile Arg Ile Phe Asp Tyr
1               5

<210> SEQ ID NO 126
<211> LENGTH: 7
<212> TYPE: PRT
<213> ORGANISM: Homo sapiens

<400> SEQUENCE: 126

Ser Ala Ser Arg Leu Gln Ser
1               5

<210> SEQ ID NO 127
<211> LENGTH: 9
<212> TYPE: PRT
<213> ORGANISM: Homo sapiens

<400> SEQUENCE: 127

Gln Gln Arg Ala Gly Thr Pro Val Thr
1               5

<210> SEQ ID NO 128
<211> LENGTH: 17
<212> TYPE: PRT
<213> ORGANISM: Homo sapiens

<400> SEQUENCE: 128

Gly Ile Thr Met Thr Gly Arg Thr Thr Lys Tyr Ala Asp Ser Val Lys
1               5                   10                  15

Gly

<210> SEQ ID NO 129
<211> LENGTH: 7
<212> TYPE: PRT
<213> ORGANISM: Homo sapiens

```
<400> SEQUENCE: 129

Asn Ser Met Ile Phe Asp Tyr
 1               5

<210> SEQ ID NO 130
<211> LENGTH: 7
<212> TYPE: PRT
<213> ORGANISM: Homo sapiens

<400> SEQUENCE: 130

Gln Ala Ser Arg Leu Gln Ser
 1               5

<210> SEQ ID NO 131
<211> LENGTH: 9
<212> TYPE: PRT
<213> ORGANISM: Homo sapiens

<400> SEQUENCE: 131

Gln Gln Arg Val Leu Arg Pro Pro Thr
 1               5

<210> SEQ ID NO 132
<211> LENGTH: 5
<212> TYPE: PRT
<213> ORGANISM: Homo sapiens

<400> SEQUENCE: 132

Arg Tyr Pro Met Ser
 1               5

<210> SEQ ID NO 133
<211> LENGTH: 7
<212> TYPE: PRT
<213> ORGANISM: Homo sapiens

<400> SEQUENCE: 133

Gly Phe Tyr Ala Phe Asp Tyr
 1               5

<210> SEQ ID NO 134
<211> LENGTH: 11
<212> TYPE: PRT
<213> ORGANISM: Homo sapiens

<400> SEQUENCE: 134

Arg Ala Ser Gln Ser Ile Val Arg Val Leu Thr
 1               5                  10

<210> SEQ ID NO 135
<211> LENGTH: 17
<212> TYPE: PRT
<213> ORGANISM: Homo sapiens

<400> SEQUENCE: 135

Thr Ile Thr Ala Ser Gly Pro Asn Thr Arg Tyr Ala Asp Ser Val Lys
 1               5                  10                  15

Gly

<210> SEQ ID NO 136
<211> LENGTH: 7
<212> TYPE: PRT
<213> ORGANISM: Homo sapiens
```

```
<400> SEQUENCE: 136

Asn His Ser Thr Phe Asp Tyr
  1               5

<210> SEQ ID NO 137
<211> LENGTH: 7
<212> TYPE: PRT
<213> ORGANISM: Homo sapiens

<400> SEQUENCE: 137

Arg Ala Ser His Leu Gln Ser
  1               5

<210> SEQ ID NO 138
<211> LENGTH: 9
<212> TYPE: PRT
<213> ORGANISM: Homo sapiens

<400> SEQUENCE: 138

Gln Gln Asn Arg Thr Ala Pro Arg Thr
  1               5

<210> SEQ ID NO 139
<211> LENGTH: 17
<212> TYPE: PRT
<213> ORGANISM: Homo sapiens

<400> SEQUENCE: 139

Thr Ile Tyr Tyr Ala Gly Ser Asn Thr Tyr Tyr Ala Asp Ser Val Lys
  1               5                  10                  15

Gly

<210> SEQ ID NO 140
<211> LENGTH: 7
<212> TYPE: PRT
<213> ORGANISM: Homo sapiens

<400> SEQUENCE: 140

Gly Tyr Tyr Thr Phe Asp Tyr
  1               5

<210> SEQ ID NO 141
<211> LENGTH: 7
<212> TYPE: PRT
<213> ORGANISM: Homo sapiens

<400> SEQUENCE: 141

Tyr Ala Ser Asn Leu Gln Ser
  1               5

<210> SEQ ID NO 142
<211> LENGTH: 9
<212> TYPE: PRT
<213> ORGANISM: Homo sapiens

<400> SEQUENCE: 142

Gln Gln Ser Asp Thr Ser Pro Thr Thr
  1               5

<210> SEQ ID NO 143
<211> LENGTH: 16
<212> TYPE: PRT
<213> ORGANISM: Homo sapiens
```

```
<400> SEQUENCE: 143

Met Ile Tyr Pro Gly Gly Tyr Thr Lys Tyr Ala Asp Ser Val Lys Gly
 1               5                  10                  15

<210> SEQ ID NO 144
<211> LENGTH: 7
<212> TYPE: PRT
<213> ORGANISM: Homo sapiens

<400> SEQUENCE: 144

Asn Ala Asp Leu Phe Asp Tyr
 1               5

<210> SEQ ID NO 145
<211> LENGTH: 7
<212> TYPE: PRT
<213> ORGANISM: Homo sapiens

<400> SEQUENCE: 145

Thr Ala Ser Arg Leu Gln Ser
 1               5

<210> SEQ ID NO 146
<211> LENGTH: 9
<212> TYPE: PRT
<213> ORGANISM: Homo sapiens

<400> SEQUENCE: 146

Gln Gln Met Arg Arg Lys Pro Ala Thr
 1               5

<210> SEQ ID NO 147
<211> LENGTH: 5
<212> TYPE: PRT
<213> ORGANISM: Homo sapiens

<400> SEQUENCE: 147

Leu Tyr Asn Met Val
 1               5

<210> SEQ ID NO 148
<211> LENGTH: 7
<212> TYPE: PRT
<213> ORGANISM: Homo sapiens

<400> SEQUENCE: 148

Glu Trp Ser Arg Phe Asp Tyr
 1               5

<210> SEQ ID NO 149
<211> LENGTH: 11
<212> TYPE: PRT
<213> ORGANISM: Homo sapiens

<400> SEQUENCE: 149

Arg Ala Ser Gln Ser Ile Ser Lys Ser Leu Ile
 1               5                  10

<210> SEQ ID NO 150
<211> LENGTH: 9
<212> TYPE: PRT
<213> ORGANISM: Homo sapiens

<400> SEQUENCE: 150
```

Gln Gln Ser Tyr Ser Thr Pro Lys Thr
1               5

<210> SEQ ID NO 151
<211> LENGTH: 5
<212> TYPE: PRT
<213> ORGANISM: Homo sapiens

<400> SEQUENCE: 151

Gly Tyr Tyr Met Ser
1               5

<210> SEQ ID NO 152
<211> LENGTH: 7
<212> TYPE: PRT
<213> ORGANISM: Homo sapiens

<400> SEQUENCE: 152

Thr His Asp Ser Phe Asp Tyr
1               5

<210> SEQ ID NO 153
<211> LENGTH: 11
<212> TYPE: PRT
<213> ORGANISM: Homo sapiens

<400> SEQUENCE: 153

Arg Ala Ser Gln Ser Ile Asp Arg Tyr Leu Asn
1               5                   10

<210> SEQ ID NO 154
<211> LENGTH: 5
<212> TYPE: PRT
<213> ORGANISM: Homo sapiens

<400> SEQUENCE: 154

Arg Tyr Gln Met Val
1               5

<210> SEQ ID NO 155
<211> LENGTH: 7
<212> TYPE: PRT
<213> ORGANISM: Homo sapiens

<400> SEQUENCE: 155

His Leu Ser Arg Phe Asp Tyr
1               5

<210> SEQ ID NO 156
<211> LENGTH: 11
<212> TYPE: PRT
<213> ORGANISM: Homo sapiens

<400> SEQUENCE: 156

Arg Ala Ser Gln Ser Ile Lys Tyr Asn Leu Ala
1               5                   10

<210> SEQ ID NO 157
<211> LENGTH: 17
<212> TYPE: PRT
<213> ORGANISM: Homo sapiens

<400> SEQUENCE: 157

Glu Ile Leu Pro Arg Gly His Arg Thr Ala Tyr Ala Asp Ser Val Lys

```
                1               5              10              15
Gly

<210> SEQ ID NO 158
<211> LENGTH: 7
<212> TYPE: PRT
<213> ORGANISM: Homo sapiens

<400> SEQUENCE: 158

Ser Gly Lys His Phe Asp Tyr
  1               5

<210> SEQ ID NO 159
<211> LENGTH: 7
<212> TYPE: PRT
<213> ORGANISM: Homo sapiens

<400> SEQUENCE: 159

Asn Ala Ser Thr Leu Gln Ser
  1               5

<210> SEQ ID NO 160
<211> LENGTH: 9
<212> TYPE: PRT
<213> ORGANISM: Homo sapiens

<400> SEQUENCE: 160

Gln Gln Arg Lys Arg Leu Pro Glu Thr
  1               5

<210> SEQ ID NO 161
<211> LENGTH: 5
<212> TYPE: PRT
<213> ORGANISM: Homo sapiens

<400> SEQUENCE: 161

Tyr Tyr Glu Met Leu
  1               5

<210> SEQ ID NO 162
<211> LENGTH: 7
<212> TYPE: PRT
<213> ORGANISM: Homo sapiens

<400> SEQUENCE: 162

Pro Phe Met Ser Phe Asp Tyr
  1               5

<210> SEQ ID NO 163
<211> LENGTH: 11
<212> TYPE: PRT
<213> ORGANISM: Homo sapiens

<400> SEQUENCE: 163

Arg Ala Ser Gln Ser Ile His Gln Asp Leu Val
  1               5                  10

<210> SEQ ID NO 164
<211> LENGTH: 17
<212> TYPE: PRT
<213> ORGANISM: Homo sapiens

<400> SEQUENCE: 164

Ser Ile Gly Ser Ser Gly Tyr Gly Thr Gly Tyr Ala Asp Ser Val Lys
```

```
                1               5              10              15
Gly

<210> SEQ ID NO 165
<211> LENGTH: 7
<212> TYPE: PRT
<213> ORGANISM: Homo sapiens

<400> SEQUENCE: 165

Gly Tyr Tyr Ser Phe Asp Tyr
 1               5

<210> SEQ ID NO 166
<211> LENGTH: 7
<212> TYPE: PRT
<213> ORGANISM: Homo sapiens

<400> SEQUENCE: 166

Asp Ala Ser Ser Leu Gln Ser
 1               5

<210> SEQ ID NO 167
<211> LENGTH: 9
<212> TYPE: PRT
<213> ORGANISM: Homo sapiens

<400> SEQUENCE: 167

Gln Gln Ser Asp Ser Ser Pro Tyr Thr
 1               5

<210> SEQ ID NO 168
<211> LENGTH: 5
<212> TYPE: PRT
<213> ORGANISM: Homo sapiens

<400> SEQUENCE: 168

Asp Tyr Asp Met Ser
 1               5

<210> SEQ ID NO 169
<211> LENGTH: 7
<212> TYPE: PRT
<213> ORGANISM: Homo sapiens

<400> SEQUENCE: 169

Asp Gly Ala Gly Phe Asp Tyr
 1               5

<210> SEQ ID NO 170
<211> LENGTH: 11
<212> TYPE: PRT
<213> ORGANISM: Homo sapiens

<400> SEQUENCE: 170

Arg Ala Ser Gln Ser Ile Gly Ser Ser Leu Ser
 1               5                  10

<210> SEQ ID NO 171
<211> LENGTH: 17
<212> TYPE: PRT
<213> ORGANISM: Homo sapiens

<400> SEQUENCE: 171

Ala Ile Ser Gly Leu Gly Lys Gln Thr Arg Tyr Ala Asp Ser Val Lys
```

```
             1               5                  10                 15
Gly

<210> SEQ ID NO 172
<211> LENGTH: 7
<212> TYPE: PRT
<213> ORGANISM: Homo sapiens

<400> SEQUENCE: 172

Gly Tyr Ser Arg Phe Asp Tyr
  1               5

<210> SEQ ID NO 173
<211> LENGTH: 7
<212> TYPE: PRT
<213> ORGANISM: Homo sapiens

<400> SEQUENCE: 173

Ser Ala Ser Leu Leu Gln Ser
  1               5

<210> SEQ ID NO 174
<211> LENGTH: 9
<212> TYPE: PRT
<213> ORGANISM: Homo sapiens

<400> SEQUENCE: 174

Gln Gln Leu Gly Thr Pro Pro Arg Thr
  1               5

<210> SEQ ID NO 175
<211> LENGTH: 5
<212> TYPE: PRT
<213> ORGANISM: Homo sapiens

<400> SEQUENCE: 175

Arg Tyr Glu Met Ser
  1               5

<210> SEQ ID NO 176
<211> LENGTH: 7
<212> TYPE: PRT
<213> ORGANISM: Homo sapiens

<400> SEQUENCE: 176

Ser Trp Thr Leu Phe Asp Tyr
  1               5

<210> SEQ ID NO 177
<211> LENGTH: 11
<212> TYPE: PRT
<213> ORGANISM: Homo sapiens

<400> SEQUENCE: 177

Arg Ala Ser Gln Ser Ile Phe Thr Asn Leu Asp
  1               5                  10

<210> SEQ ID NO 178
<211> LENGTH: 11
<212> TYPE: PRT
<213> ORGANISM: Homo sapiens

<400> SEQUENCE: 178

Arg Ala Ser Gln Ser Ile Gly Thr Leu Leu Arg
```

```
<210> SEQ ID NO 179
<211> LENGTH: 11
<212> TYPE: PRT
<213> ORGANISM: Homo sapiens

<400> SEQUENCE: 179

Arg Ala Ser Gln Ser Ile His Ser Arg Leu Ser
 1               5                  10

<210> SEQ ID NO 180
<211> LENGTH: 5
<212> TYPE: PRT
<213> ORGANISM: Homo sapiens
<220> FEATURE:
<223> OTHER INFORMATION: Description of Artificial Sequence:Linker
      peptide for connecting variable domains.

<400> SEQUENCE: 180

Gly Gly Gly Gly Ser
 1               5

<210> SEQ ID NO 181
<211> LENGTH: 20
<212> TYPE: DNA
<213> ORGANISM: Homo sapiens

<400> SEQUENCE: 181
gaggtgcagc tgttggagtc                                          20

<210> SEQ ID NO 182
<211> LENGTH: 69
<212> TYPE: DNA
<213> ORGANISM: Homo sapiens
<220> FEATURE:
<221> NAME/KEY: V_segment
<222> LOCATION: (23)..(51)
<223> OTHER INFORMATION: N at positions 23, 24, 29, 30, 32, 33, 38,
      39, 41, 42, 44, 45, 50 and 51 can be any nucleotide for
      PCR priming of variant sequences.

<400> SEQUENCE: 182
gcccttcacg gagtctgcgt amnntgtmnn mnnaccmnnm nnmnnaatmn ntgagaccca      60
ctccagccc                                                             69

<210> SEQ ID NO 183
<211> LENGTH: 69
<212> TYPE: DNA
<213> ORGANISM: Homo sapiens

<400> SEQUENCE: 183
tabhtgagac ccactccagc ccgcccttca cggagtctgc gtaabhtgta bhabhaccab      60 habhabhaa                                                             69

<210> SEQ ID NO 184
<211> LENGTH: 19
<212> TYPE: DNA
<213> ORGANISM: Homo sapiens

<400> SEQUENCE: 184
cgcagactcc gtgaagggc                                           19

<210> SEQ ID NO 185
```

<211> LENGTH: 53
<212> TYPE: DNA
<213> ORGANISM: Homo sapiens
<220> FEATURE:
<221> NAME/KEY: V_segment
<222> LOCATION: (23)..(33)
<223> OTHER INFORMATION: N at positions 23, 24, 26, 27, 29, 30, 32 and
      33 can be any nucleotide to allow PCR priming of
      variant sequences.

<400> SEQUENCE: 185
tccctggccc cagtagtcaa amnmnnmnn mnntttcgca cagtaatata cgg         53

<210> SEQ ID NO 186
<211> LENGTH: 53
<212> TYPE: DNA
<213> ORGANISM: Homo sapiens

<400> SEQUENCE: 186
tccctggccc cagtagtcaa aabhabhabh abhtttcgca cagtaatata cgg         53

<210> SEQ ID NO 187
<211> LENGTH: 20
<212> TYPE: DNA
<213> ORGANISM: Homo sapiens

<400> SEQUENCE: 187
gacatccaga tgacccagtc                                             20

<210> SEQ ID NO 188
<211> LENGTH: 51
<212> TYPE: DNA
<213> ORGANISM: Homo sapiens
<220> FEATURE:
<221> NAME/KEY: V_segment
<222> LOCATION: (21)..(31)
<223> OTHER INFORMATION: N at positions 21, 22, 30 and 31 can be any
      nucleotide, allowing for PCR priming of variant
      sequences.

<400> SEQUENCE: 188
atgggacccc actttgcaam nnggatgcmn natagatcag gagcttaggg g           51

<210> SEQ ID NO 189
<211> LENGTH: 51
<212> TYPE: DNA
<213> ORGANISM: Homo sapiens

<400> SEQUENCE: 189
atgggacccc actttgcaaa bhggatgcab hatagatcag gagcttaggg g           51

<210> SEQ ID NO 190
<211> LENGTH: 19
<212> TYPE: DNA
<213> ORGANISM: Homo sapiens

<400> SEQUENCE: 190
ttgcaaagtg gggtcccat                                              19

<210> SEQ ID NO 191
<211> LENGTH: 60
<212> TYPE: DNA
<213> ORGANISM: Homo sapiens
<220> FEATURE:
<221> NAME/KEY: V_segment
<222> LOCATION: (23)..(39)
<223> OTHER INFORMATION: N at positions 23, 24, 29, 30, 32, 33, 35, 36, 38 and 39 can be any nucleotide, allowing for PCR
       priming of variant sequences.

<400> SEQUENCE: 191
cttggtccct tggccgaacg tmnnaggmnn mnnmnnmnnc tgttgacagt agtaagttgc    60

<210> SEQ ID NO 192
<211> LENGTH: 60
<212> TYPE: DNA
<213> ORGANISM: Homo sapiens

<400> SEQUENCE: 192
cttggtccct tggccgaacg tabhaggabh abhabhabhc tgttgacagt agtaagttgc    60

<210> SEQ ID NO 193
<211> LENGTH: 20
<212> TYPE: DNA
<213> ORGANISM: Homo sapiens

<400> SEQUENCE: 193
gaggtgcagc tgttggagtc                                                20

<210> SEQ ID NO 194
<211> LENGTH: 53
<212> TYPE: DNA
<213> ORGANISM: Homo sapiens
<220> FEATURE:
<221> NAME/KEY: V_segment
<222> LOCATION: (21)..(34)
<223> OTHER INFORMATION: N at positions 21, 22, 27, 28, 33 and 34 can be
       any nucleotide, allowing for PCR priming of
       variant sequences.

<400> SEQUENCE: 194
ctggagcctg gcggacccam nncatmnnat amnngctaaa ggtgaatcca gag           53

<210> SEQ ID NO 195
<211> LENGTH: 53
<212> TYPE: DNA
<213> ORGANISM: Homo sapiens

<400> SEQUENCE: 195
ctggagcctg gcggacccaa bhcatabhat aabhgctaaa ggtgaatcca gag           53

<210> SEQ ID NO 196
<211> LENGTH: 19
<212> TYPE: DNA
<213> ORGANISM: Homo sapiens

<400> SEQUENCE: 196
tgggtccgcc aggctccag                                                 19

<210> SEQ ID NO 197
<211> LENGTH: 53
<212> TYPE: DNA
<213> ORGANISM: Homo sapiens
<220> FEATURE:
<221> NAME/KEY: V_segment
<222> LOCATION: (23)..(33)
<223> OTHER INFORMATION: N at positions 23, 24, 26, 27, 29, 30, 32 and
       33 can be any nucleotide, allowing for PCR priming of
       variant sequences.

<400> SEQUENCE: 197
tccctggccc cagtagtcaa amnnmnnmnn mnntttcgca cagtaatata cgg           53

<210> SEQ ID NO 198
<211> LENGTH: 53
<212> TYPE: DNA
<213> ORGANISM: Homo sapiens

<400> SEQUENCE: 198
tccctggccc cagtagtcaa aabhabhabh abhtttcgca cagtaatata cgg         53

<210> SEQ ID NO 199
<211> LENGTH: 20
<212> TYPE: DNA
<213> ORGANISM: Homo sapiens

<400> SEQUENCE: 199
gacatccaga tgacccagtc                                              20

<210> SEQ ID NO 200
<211> LENGTH: 53
<212> TYPE: DNA
<213> ORGANISM: Homo sapiens
<220> FEATURE:
<221> NAME/KEY: V_segment
<222> LOCATION: (21)..(34)
<223> OTHER INFORMATION: N at positions 21, 22, 27, 28, 30, 31, 33 and
      34 can be any nucleotide, allowing for PCR priming of
      variant sequences.

<400> SEQUENCE: 200
ctggtttctg ctgataccam nntaamnnmn nmnnaatgct ctgacttgcc cgg         53

<210> SEQ ID NO 201
<211> LENGTH: 53
<212> TYPE: DNA
<213> ORGANISM: Homo sapiens

<400> SEQUENCE: 201
ctggtttctg ctgataccaa bhtaaabhab habhaatgct ctgacttgcc cgg         53

<210> SEQ ID NO 202
<211> LENGTH: 21
<212> TYPE: DNA
<213> ORGANISM: Homo sapiens

<400> SEQUENCE: 202
tggtatcagc agaaaccagg g                                            21

<210> SEQ ID NO 203
<211> LENGTH: 60
<212> TYPE: DNA
<213> ORGANISM: Homo sapiens
<220> FEATURE:
<221> NAME/KEY: V_segment
<222> LOCATION: (23)..(24)
<223> OTHER INFORMATION: N at positions 23 and 24 can be any nucleotide,
      allowing for PCR priming of variant sequences.

<400> SEQUENCE: 203
cttggtccct tggccgaacg tmnnaggggt actgtaactc tgttgacagt agtaagttgc  60

<210> SEQ ID NO 204
<211> LENGTH: 60
<212> TYPE: DNA
<213> ORGANISM: Homo sapiens

<400> SEQUENCE: 204

```
cttggtccct tggccgaacg tabhagggt actgtaactc tgttgacagt agtaagttgc    60
```

<210> SEQ ID NO 205
<211> LENGTH: 53
<212> TYPE: DNA
<213> ORGANISM: Homo sapiens

<400> SEQUENCE: 205

```
gtcctcgcaa ctgcggccca gccggccatg gccgaggtgc agctgttgga gtc    53
```

<210> SEQ ID NO 206
<211> LENGTH: 56
<212> TYPE: DNA
<213> ORGANISM: Homo sapiens

<400> SEQUENCE: 206

```
gaaccgcctc caccgctcga gacggtgacc agggttccct ggcccagta gtcaaa    56
```

<210> SEQ ID NO 207
<211> LENGTH: 71
<212> TYPE: DNA
<213> ORGANISM: Homo sapiens

<400> SEQUENCE: 207

```
agcggtggag gcggttcagg cggaggtggc agcggcggtg gcgggtcgac ggacatccag    60
atgacccagt c                                                         71
```

<210> SEQ ID NO 208
<211> LENGTH: 59
<212> TYPE: DNA
<213> ORGANISM: Homo sapiens

<400> SEQUENCE: 208

```
gagtcattct cgacttgcgg ccgcccgttt gatttccacc ttggtccctt ggccgaacg    59
```

<210> SEQ ID NO 209
<211> LENGTH: 53
<212> TYPE: DNA
<213> ORGANISM: Homo sapiens

<400> SEQUENCE: 209

```
gtcctcgcaa ctgcggccca gccggccatg gccgaggtgc agctgttgga gtc    53
```

<210> SEQ ID NO 210
<211> LENGTH: 56
<212> TYPE: DNA
<213> ORGANISM: Homo sapiens

<400> SEQUENCE: 210

```
gaaccgcctc caccgctcga gacggtgacc agggttccct ggcccagta gtcaaa    56
```

<210> SEQ ID NO 211
<211> LENGTH: 71
<212> TYPE: DNA
<213> ORGANISM: Homo sapiens

<400> SEQUENCE: 211

```
agcggtggag gcggttcagg cggaggtggc agcggcggtg gcgggtcgac ggacatccag    60
atgacccagt c                                                         71
```

<210> SEQ ID NO 212
<211> LENGTH: 59

-continued

```
<212> TYPE: DNA
<213> ORGANISM: Homo sapiens

<400> SEQUENCE: 212
gagtcattct cgacttgcgg ccgcccgttt gatttccacc ttggtccctt ggccgaacg      59
```